(12) United States Patent
Su et al.

(10) Patent No.: US 9,217,015 B2
(45) Date of Patent: Dec. 22, 2015

(54) CYCLOSPORIN DERIVATIVES FOR THE TREATMENT AND PREVENTION OF A VIRAL INFECTION

(75) Inventors: Zhuang Su, Andover, MA (US); Zhennian Huang, Newton, MA (US); Zhengyu Long, Bolton, MA (US); Suizhou Yang, Dracut, MA (US)

(73) Assignee: S&T Global Inc., Woburn, MA (US)

( * ) Notice: Subject to any disclaimer, the term of this patent is extended or adjusted under 35 U.S.C. 154(b) by 69 days.

(21) Appl. No.: 13/810,589

(22) PCT Filed: Jul. 18, 2011

(86) PCT No.: PCT/US2011/044362
§ 371 (c)(1),
(2), (4) Date: Jul. 30, 2013

(87) PCT Pub. No.: WO2012/009715
PCT Pub. Date: Jan. 19, 2012

(65) Prior Publication Data
US 2013/0303438 A1 Nov. 14, 2013

Related U.S. Application Data

(60) Provisional application No. 61/364,942, filed on Jul. 16, 2010.

(51) Int. Cl.
| | | |
|---|---|---|
| A61K 38/12 | (2006.01) |
| A61K 39/29 | (2006.01) |
| C07K 14/16 | (2006.01) |
| C07K 7/64 | (2006.01) |
| A61K 38/13 | (2006.01) |

(52) U.S. Cl.
CPC .............. *C07K 7/645* (2013.01); *A61K 38/13* (2013.01)

(58) Field of Classification Search
None
See application file for complete search history.

(56) References Cited

U.S. PATENT DOCUMENTS

| | | | |
|---|---|---|---|
| 3,869,448 | A | 3/1975 | Earley et al. |
| 4,108,985 | A | 8/1978 | Ruegger et al. |
| 4,703,033 | A | 10/1987 | Seebach |
| 5,767,069 | A | 6/1998 | Ko et al. |
| 5,965,527 | A * | 10/1999 | Barriere et al. ............ 514/2.4 |
| 5,981,479 | A | 11/1999 | Ko et al. |
| 5,994,299 | A | 11/1999 | Barriere et al. |
| 6,583,265 | B1 | 6/2003 | Ellmerer-Muller et al. |
| 6,927,208 | B1 | 8/2005 | Wenger et al. |
| 7,439,227 | B2 | 10/2008 | Scalfaro et al. |
| 7,511,013 | B2 | 3/2009 | Molino et al. |
| 7,696,166 | B2 | 4/2010 | Molino |
| 7,718,767 | B2 | 5/2010 | Fliri et al. |
| 2006/0069015 | A1 | 3/2006 | Molino et al. |
| 2006/0160727 | A1* | 7/2006 | Fliri et al. ............ 514/11 |
| 2010/0167996 | A1 | 7/2010 | Fliri et al. |
| 2010/0173836 | A1 | 7/2010 | Li et al. |
| 2010/0173837 | A1 | 7/2010 | Hopkins |
| 2010/0196316 | A1 | 8/2010 | Or et al. |

FOREIGN PATENT DOCUMENTS

| | | |
|---|---|---|
| CN | 101068829 A | 11/2007 |
| WO | WO-0001715 A1 | 1/2000 |
| WO | WO-2006/038088 A1 | 4/2006 |
| WO | WO-2006/038119 A1 | 4/2006 |
| WO | WO-2008143996 A1 | 11/2008 |
| WO | WO-2012009715 A2 | 1/2012 |
| WO | WO-2012021796 A2 | 2/2012 |
| WO | WO-2012075494 A1 | 6/2012 |

OTHER PUBLICATIONS

Evers, 2003, Bioorganic & Medicinal Chemistry Letters, 13, 4415-4419.*
Berge, S.M. et al., "Pharmaceutical Salts," Journal of Pharmaceutical Sciences, vol. 66, No. 1, pp. 1-19 (Jan. 1977).
Bouchard, M.J. et al., "Activation and Inhibition of Cellular Calcium and Tyrosine Kinase Signaling Pathways Identify Targets of the HBx Protein Involved in Hepatitis B Virus Replication," Journal of Virology, vol. 77, No. 14, pp. 7713-7719, 8 pages (Jul. 2003).
Castro, A.P.V. et al., "Redistribution of Cyclophilin A to Viral Factories during Vaccinia Virus Infection and Its Incorporation into Mature Particles," Journal of Virology, vol. 77, No. 16, pp. 9052-9068, 18 pages (Aug. 2003).
Chen, Z. et al., "Function of HAb18G/CD147 in Invasion of Host Cells by Severe Acute Respiratory Syndrome Coronavirus," The Journal of Infectious Diseases, vol. 191, Issue 5, pp. 755-760 (Mar. 1, 2005).
Chokshi, S. et al., "1104: Characterization of Antiviral Activities of Cyclophilin Inhibitors DEB025 (Alisporivir) and NIM811 on Hepatitis B Virus (HBV) Replication and HBSAG Secretion In Vitro," 07a: Viral Hepatitis B&D: Experimental, Journal of Hepatology, vol. 54, pp. S437-S438 (2011).

(Continued)

*Primary Examiner* — Satyanarayana R Gudibande
(74) *Attorney, Agent, or Firm* — Wilmer Cutler Pickering Hale and Dorr LLP

(57) ABSTRACT

The present invention relates to a compound of the formula (I): or pharmaceutically acceptable salt thereof, wherein the symbols are as defined in the specification; a pharmaceutical composition comprising the same, a method for treating or preventing a viral infection using the same.

(I)

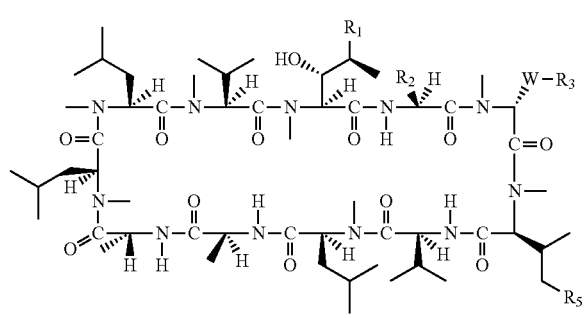

7 Claims, No Drawings

(56) References Cited

OTHER PUBLICATIONS

First Office Action issued by the Patent Office of the People's Republic of China for Application No. 201180035147.9 mailed on Feb. 20, 2014 (16 pages total).
Fliri, H. et al., "Cyclosporins. Structure-activity relationships," Ann N.Y. Acad. Sci., vol. 696, pp. 47-53 (Nov. 1993).
Franke, E.A. et al., "Specific incorporation of cyclophilin A into HIV-1 virions," Nature, vol. 372, pp. 359-362 (Nov. 24, 1994).
Hopkins, S. et al., "SCY-635, a Novel Nonimmunosuppressive Analog of Cyclosporine That Exhibits Potent Inhibition of Hepatitis C Virus RNA Replication In Vitro," Antimicrobial Agents and Chemotherapy, vol. 54, No. 2, pp. 660-672 (Feb. 2010).
Hopkins, S. et al., "SCYNEXIS's SCY-635 Demonstrates Impressive Barrier to Resistance in HCV Treatment," The 45th Annual Meeting of the European Association for the Study of the Liver, Vienna, Austria, 2 pages (Apr. 15, 2010).
Inoue, K. et al., "Combined interferon α2b and cyclosporin A in the treatment of chronic hepatitis C: controlled trial," Journal of Gastroenterology, vol. 38, No. 6, pp. 567-572 (Jun. 2003).
Inoue, K. et al., "IFN combined cyclosporin A therapy," Nippon Rinsho, vol. 59, No. 7, pp. 1326-1330 (Jul. 2001).
International Search Report and Written Opinion issued by the International Searching Authority for Application No. PCT/US11/44362 mailed on Feb. 2, 2012 (10 pages).
Klatzmann, D. et al., "Functional inhibition by cyclosporin A of the lymphocyte receptor for the AIDS virus (HIV)," C.R. Acad. Sci. III, vol. 303, No. 9, pp. 343-348 (1986) (abstract included).
Krieger, N. et al., "Enhancement of Hepatitis C Virus RNA Replication by Cell Culture-Adaptive Mutations," Journal of Virology, vol. 75, No. 10, pp. 4614-4624, 12 pages (May 2001).
Kuhnt, M. et al., "Microbial biotransformation products of cyclosporin A," The Journal of Antibiotics, vol. 49, No. 8, pp. 781-787 (1996).
Lill, J. et al., "Cyclosporine-Drug Interactions and the Influence of Patient Age," Am. J. Health-Syst. Pharm., vol. 57, pp. 1579-1584 (Sep. 1, 2000).
Liu, X. et al., "Cyclophilin A interacts with influenza A virus M1 protein and impairs the early stage of the viral replication," Cellular Microbiology, vol. 11, No. 5, pp. 730-741 (Feb. 6, 2009).
Luban, Jeremy, "Absconding with the Chaperone: Essential Cyclophilin-Gag Interaction in HIV-1 Virions," Cell, vol. 87, pp. 1157-1159 (Dec. 27, 1996).
Luban,J. et al., "Human immunodeficiency virus type 1 Gag protein binds to cyclophilins A and B," Cell, vol. 73, Issue 6, pp. p1067-p1078 (Jun. 18, 1993).
No Author Listed, "Sandoz Axes Cyclosporine Research," GMHC Treatment Issues, vol. 9, No. 12, pp. 6-7 (Dec. 1995).
Papageorgiou, C. et al., "Calcineurin has a very tight-binding pocket for the side chain of residue 4 of cyclosporin," Bioorganic & Medicinal Chemistry Letters, vol. 4, No. 2, pp. 267-272 (Jan. 1994).
Papageorgiou, C. et al., "Improved Binding Affinity for Cyclophilin A by a Cyclosporin Derivative Singly Modified at Its effector Domain," Journal of Medicinal Chemistry, vol. 37, No. 22, pp. 3674-3676 (1994).
Pietschmann, T. et al., "Persistent and Transient Replication of Full-Length Hepatitis C Virus Genomes in Cell Culture," Journal of Virology, vol. 76, No. 8, pp. 4008-4021, 15 pages (Apr. 2002).
Rosenwirth, B. et al., "Inhibition of human immunodeficiency virus type 1 replication by SDZ NIM 811, a nonummunosuppressive cyclosporine analog," Antimicrobial Agents and Chemotherapy, vol. 38, No. 8, pp. 1763-1772, 11 pages (Aug. 1994).
Seebach, D. et al., "Modification of Cyclosporin A (CS): Generation of an enolate at the sarcosine residue and reactions with electrophiles," Helvetica Chimica Acta, vol. 76, Issue 4, pp. 1564-1590 (Jun. 30, 1993).
Tang, Hengli, "Cyclophilin Inhibitors as a Novel HCV Therapy," Viruses, vol. 2, No. 8, pp. 1621-1634 (Aug. 5, 2010).
Tian, X. et al., "Hepatitis B Virus (HBV) Surface Antigen Interacts with and Promotes Cyclophilin A Secretion: Possible Link to Pathogenesis of HBV Infection," Journal of Virology, vol. 84, No. 7, pp. 3373-3381, 10 pages (Apr. 2010).
Wainberg, M.A. et al., "The effect of cyclosporine A on infection of susceptible cells by human immunodeficiency virus type 1," Blood, vol. 72, No. 6, pp. 1904-1910, 8 pages (Dec. 1988).
Watashi, K. et al., "Chemical genetics approach to hepatitis C virus replication: cyclophilin as a target for anti-hepatitis C virus strategy," Reviews in Medical Virology, vol. 17, Issue 4, pp. 245-252 (Jul./Aug. 2007).
Watashi, K. et al., "Cyclosporin A Suppresses Replication of Hepatitis C Virus Genome in Cultured Hepatocytes," Hepatology, vol. 38, No. 5, pp. 1282-1288 (2003).
Zenke, G. et al., "Molecular mechanisms of Immunosuppression by Cyclosporins," Annals of the New York Academy of Sciences, vol. 685, pp. 330-335 (Jun. 1993).
International Search Report and Written Opinion issued by the U.S. Patent and Trademark Office as International Searching Authority for International Application No. PCT/US11/047571 mailed Feb. 29, 2012 (13 pgs.).
Extended European Search Report issued by the European Patent Office for European Patent Application No. 11845460.2 dated Apr. 30, 2014 (11 pgs.).
International Search Report and Written Opinion issued by the U.S. Patent and Trademark Office as International Searching Authority for International Application No. PCT/US11/063295 mailed Apr. 23, 2012 (10 pgs.).
International Search Report and Written Opinion issued by the U.S. Patent and Trademark Office as International Searching Authority for International Application No. PCT/US12/51572 mailed Oct. 16, 2012 (11 pgs.).
International Search Report and Written Opinion issued by the U.S. Patent and Trademark Office as the International Searching Authority for International Application No. PCT/US14/030491 mailed on Nov. 5, 2014 (10 pages).
Thali, et al., "Functional association of cyclophilin A with HIV-1 virions," Nature, vol. 372(6504), pp. 363-365 (Nov. 24, 1994).

* cited by examiner

CYCLOSPORIN DERIVATIVES FOR THE TREATMENT AND PREVENTION OF A VIRAL INFECTION

CROSS REFERENCE TO RELATED APPLICATIONS

This application claims the benefit of U.S. Provisional Application No. 61/364,942, filed Jul. 16, 2010, the entire contents of which are hereby incorporated by reference herein.

FIELD OF INVENTION

The invention relates to novel cyclosporine derivatives, their pharmaceutical compositions comprising the same, and methods for treating or preventing a viral infection using the same.

BACKGROUND OF THE INVENTION

Naturally occurring cyclosporins are poly-N-methyl, cyclic undecapeptides, isolated from fungi. Cyclosporin A has an immunosuppressive activity and has been used for almost 40 years to prevent rejection in kidney, heart and liver transplant recipients. It has anti-inflammatory property and is useful for treating rheumatoid arthritis, severe psoriasis, Behget's uveitis and dry eye disease. In addition, it is useful for treating severe ulcerative colitis, Crohn's disease, alopecia areata, aplastic anemia, HSV-1 stromal keratitis, systemic lupus erythematosus, and severe lupus nephritis.

The anti-HIV activity of cyclosporin A was discovered (Klatzmann D. et al., 1986, C R Acad. Sci. III, 303(9):343-8; Wainberg M. A., et al., 1988, Blood, 72, 1904-10; Luban, J. et al., 1993, Cell, 73, 1067-1078; each of which is incorporated herein by reference). Its non-immunosuppressive derivative, NIM-811 was reported to have potent anti HIV activity, due to its ability to inhibit cyclophilin A (Franke, E. K., et al., 1994, Nature, 372, 359-362; Thali, M., et al., 1994, Nature, 372, 363-365; Gamble T. R., et al., 1996, Cell, 87, 1157-1159; Rosenwirth B., et al., 1994, Antimicrob. Agents Chemother., 38, 1763-1772; each of which is incorporated herein by reference).

Cyclosporin A and its non-immunosuppressive derivatives, as such as NIM-811 (N-MeIle-4-Cyclosporin), Debio-025, and SCY-635, inhibit cyclophilin A and B, which interact with HCV protein NS5B and stimulate its RNA-binding activity. As a result, these compounds have an effective anti-HCV activity (Watashi, K., et al., 2007, Rev. Med. Virol., 17:245-252.37; Inoue K., et al., 2001, Nippon Rinsho., 59, 1326-30; Inoue K., et al., 2003, J. Gastroenterol., 38, 567-72; Watashi K., et al., 2003, Hepatology, 38, 1282-8; each of which is incorporated herein by reference). Currently, NIM-811, Debio-025, and SCY-635 are undergoing clinical trials for treating HCV.

NIM-811 and Debio-025 have a chemical structure similar to cyclosporine A, and have poor pharmacokinetic profile and poor oral absorption. In addition, they are metabolized by P450 for inducing drug interactions (Lill J. et al., 2000, Am J Health-Syst Pharm 57, 1579; incorporated herein by reference).

SCY-635 has an improved pharmacokinetic profile and low blood serum binding. In addition, it is less metabolized by P450 and has low potential for drug-drug interactions (Hopkins S. et al., 2010, Antimicrob. Agents Chemother., 54, 660; incorporated herein by reference). However, SCY-635 is not chemically stable according to testing results in our laboratory. SCY-635 is easily converted to its diastereoisomer by epimerization, which is expected to have poor binding activity with cyclophilin, and therefore has poor anti-viral activity.

Cyclosporin A and its non-immunosuppressive derivatives were also found to possess anti-HBV activity through the inhibition of cyclophilins (Chokshi S. et al., 2011, Abstract 190 (Poster Presentations), 46th Annual Meeting of the European Association for the Study of the Liver (EASL 2011), Berlin, March 30-April 3; Tian, X. C. et al., 2010, J. Virol., 84, 3373-3381; Xia W. L., et al., 2004, Hepatobiliary Pancreat Dis Int., 4, 18-22; Michael J. et al., 2003, J. Virol., 77, 7713-7719; each of which is incorporated herein by reference).

Furthermore, Cyclophilin were reported to regulate life cycles and pathogenesis of several viruses, including influenza A virus, severe acute respiratory syndrome coronavirus, and vaccinia virus (Castro, A. P. et al., 2003, J. Virol., 77, 9052-9068; Chen, Z., L. et al., 2005, J. Infect. Dis. 191, 755-760; Liu, X., L. et al., 2009, Cell Microbiol., 11, 730-741; each of which is incorporated herein by reference). Cyclosporin A and its non-immunosuppressive derivative also possess such anti viral-activities.

N-MeVal-4-Cyclosporin (SDZ 220-384), another non-immunosuppressive cyclosporine derivative, has similar chemical structure and similar biological activity compared to NIM-811 (Fliri et al., 1993, Ann. N Y Acad. Sci. 696, 47-53; Zenke et al., 1993, Ann N Y Acad Sci. 23; 685:330-5).

Hepatitis C virus (HCV) is a small (55-65 nm in size), enveloped, positive sense single strand RNA virus in the family Flaviviridae. HCV has a high rate of replication and has an exceptionally high mutation rate. Most people infected with HCV (about 80%) develop chronic, persistent infection. More than 4 million Americans have been infected with HCV and more than 200 million people are estimated to be infected chronically worldwide. About 35,000 new cases of hepatitis C are estimated to occur in the United States each year. HCV infection is responsible for about 50% of all chronic liver disease, 30% of all liver transplants, and 30% of all cirrhosis, end-stage liver disease, and liver cancer in the U.S. The peg-interferon and ribavirin combination is the standard treatment for chronic hepatitis C but has low efficacy against HCV infection. Recently, the FDA has approved Vertex's Incivek (telaprevir) and Merck's Victrelis (boceprevir) as an add-on to the current interferon/ribavirin therapy for treating HCV. Both drugs are HCV protease inhibitors and target virus to prevent its replication. However, due to the fast mutation of HCV, drug resistance can be developed in a short period of time for the new drugs. There exists a need for an effective therapeutic for HCV treatment.

Hepatitis B virus (HBV) is a 42 nm partially double stranded DNA virus, composed of a 27 nm nucleocapsid core (HBcAg), surrounded by an outer lipoprotein envelope containing the surface antigen (HBsAg). About a quarter of the world's population, more than 2 billion people, have been infected with the hepatitis B virus. This includes 350 million chronic carriers of the virus. The disease has caused epidemics in parts of Asia and Africa, and it is endemic in China. Chronic hepatitis B will cause liver cirrhosis and liver cancer—a fatal disease with very poor response to current chemotherapy. Although the infection is preventable by vaccination and HBV load and replication can be reduced by current antiviral drugs lamivudine (Epivir), adefovir (Hepsera), tenofovir (Viread), telbivudine (Tyzeka) and entecavir (Baraclude) and the two immune system modulators interferon alpha-2a and PEGylated interferon alpha-2a (Pegasys), none of the available drugs can clear the infection. There remains a need for an effective therapeutic for treating or preventing HBV infection.

The non-immunosuppressive Cyclosporins derivatives bind to cyclophilin, a family of host proteins that catalyze cis-tans peptidyl-prolyl isomerization in protein folding, which is crucial for the processing, maturation of the viral proteins for viral replication. It is also different to current anti-HIV and anti-HCV drugs, the advantages of targeting host cofactors—cyclophilins by cyclosporine derivatives is the presumed higher genetic barrier to development of resistance (Rosenwirth B., et al., 1994, Antimicrob. Agents Chemother., 38, 1763-1772; Tang H. L. et al., 2010, Viruses, 2, 1621-1634; Hopkins S. et al., 2010, Oral Presentation, Scynexis's SCY-635 Demonstrates Impressive Barrier to Resistance in HCV Treatment, the 45th Annual Meeting of the European Association for the Study of the Liver (EASL 2010), Vienna, Austria, April 14-18; each of which is incorporated herein by reference). Cyclosporine derivatives affect a new target-cyclophilin, and therefore represent a new mechanism of action against HCV.

Cyclophilins are a family of enzymes that assist in the folding and transportation of other proteins synthesized within a cell. Protein folding or misfolding plays a important role in the pathophysiology of a number of serious diseases, such as viral diseases (HIV, HBV, HCV, and herpes simplex virus), central nervous system disorders (mitochondrial protection for stroke, traumatic brain and spinal cord injury, Alzheimer, Parkinson's Disease, and Huntington's Diseases), cancer, cardiovascular diseases (reperfusion injury, heart attack, chronic heart failure), inflammation (respiratory inflammation, asthma, ulcerative colitis, rheumatoid arthritis, dry eye disease), muscular dystrophy, Atopic Dermatitis, Cancer, anti fungal and anti-parasitic treatment, and hair growth. Cyclosporin derivatives target cyclophilin and can play crucial role for treatment of such many diseases.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

SUMMARY OF THE INVENTION

In one aspect, the present invention provides a method for treating or preventing hepatitis C virus infection or hepatitis B virus infection in a mammalian species in need thereof, the method comprising administering to the mammalian species a therapeutically effective amount of a compound of the formula (I):

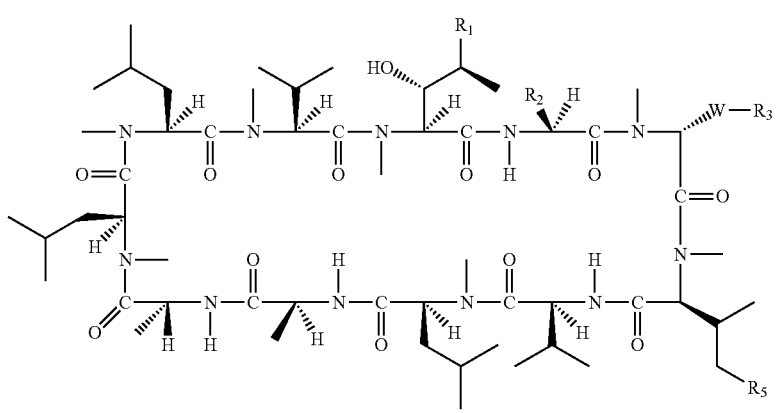

(I)

or pharmaceutically acceptable salt thereof, wherein the symbols have the following meanings and are, for each occurrence, independently selected:

$R_1$ is n-butyl or (E)-but-2-enyl;
$R_2$ is ethyl, 1-hydroxyethyl, isopropyl or n-propyl;
W is O, or S;
$R_3$ is alkyl or substituted alkyl, alkenyl or substituted alkenyl, alkynyl or substituted alkynyl, cycloalkyl or substituted cycloalkyl, or cycloalkenyl or substituted cycloalkenyl; and
$R_5$ is hydrogen or methyl.

In another aspect, the present invention provides a compound of formula (Ia):

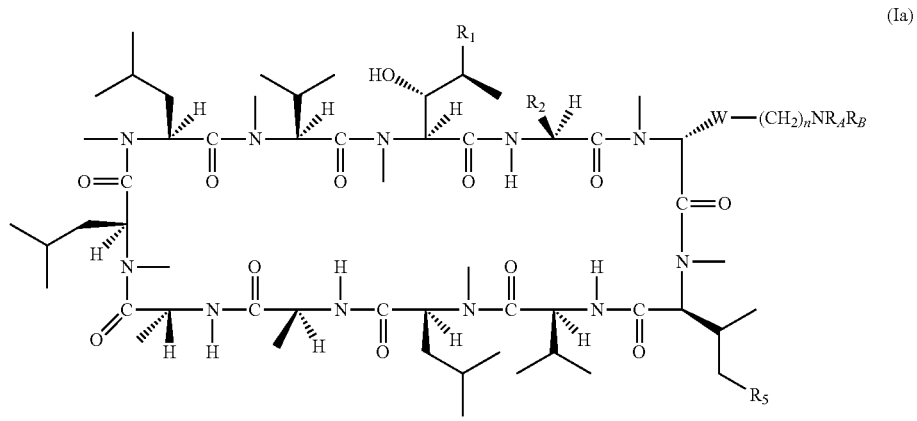

(Ia)

or pharmaceutically acceptable salt thereof, wherein the symbols have the following meanings and are, for each occurrence, independently selected:

$R_1$ is n-butyl or (E)-but-2-enyl;
$R_2$ is ethyl, 1-hydroxyethyl, isobutyl or n-butyl;
W is O or S;
n is an integer of 3, 4, 5 or 6;
each occurrence of $R_A$ and $R_B$ is independently hydrogen; $(C_1-C_4)$alkyl, optionally substituted by one or more groups $R_D$ which may be the same or different, in which each occurrence of $R_D$ is independently halogen, hydroxy, $O(C_1-C_4)$alkyl, $C(=O)(C_1-C_4)$alkyl, $C(=O)O(C_1-C_4)$alkyl; or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from $(C_1-C_4)$alkyl, phenyl and benzyl.

In yet another aspect, the present invention provides a pharmaceutical composition comprising at least one compound as described herein and a pharmaceutically-acceptable carrier.

In a further aspect, the present invention provides a method for treating or preventing a viral infection in a mammalian species in need thereof, the method comprising administering to the mammalian species a therapeutically effective amount of at least one compound as described herein.

In another aspect, the present invention provides a method for treating or preventing hepatitis C virus or hepatitis B virus infection in a mammalian species in need thereof, the method comprising administering to the mammalian species a therapeutically effective amount of at least one compound as described herein.

DETAILED DESCRIPTION OF THE INVENTION

Definitions

The following are definitions of terms used in the present specification. The initial definition provided for a group or term herein applies to that group or term throughout the present specification individually or as part of another group, unless otherwise indicated.

The terms "alkyl" and "alk" refers to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. The term "$(C_1-C_4)$alkyl" refers to a straight or branched chain alkane (hydrocarbon) radical containing from 1 to 4 carbon atoms, such as methyl, ethyl, propyl, isopropyl, n-butyl, t-butyl, and isobutyl. The term "$(C_1-C_6)$alkyl" refers to a straight or branched chain alkane (hydrocarbon) radical containing from 1 to 6 carbon atoms, such as n-hexyl, 2-methylpentyl, 3-methylpentyl, 4-methylpentyl, 2,3-dimethylbutyl, 2,2-dimethylbutyl, in addition to those exemplified for "$(C_1-C_4)$alkyl." "Substituted alkyl" refers to an alkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. In the aforementioned exemplary substitutents, groups such as alkyl, cycloalkyl, alkenyl, alkynyl, cycloalkenyl, heterocycle and aryl can themselves be optionally substituted.

The term "alkenyl" refers to a straight or branched chain hydrocarbon radical containing from 2 to 12 carbon atoms and at least one carbon-carbon double bond. Exemplary such groups include ethenyl or allyl. The term "$C_2-C_6$ alkenyl" refers to a straight or branched chain hydrocarbon radical containing from 2 to 6 carbon atoms and at least one carbon-carbon double bond, such as ethylenyl, propenyl, 2-propenyl, (E)-but-2-enyl, (Z)-but-2-enyl, 2-methy(E)-but-2-enyl, 2-methy(Z)-but-2-enyl, 2,3-dimethyl-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. "Substituted alkenyl" refers to an alkenyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted.

The term "alkynyl" refers to a straight or branched chain hydrocarbon radical containing from 2 to 12 carbon atoms and at least one carbon to carbon triple bond. Exemplary such groups include ethynyl. The term "$C_2-C_6$ alkynyl" refers to a straight or branched chain hydrocarbon radical containing from 2 to 6 carbon atoms and at least one carbon-carbon triple bond, such as ethynyl, prop-1-ynyl, prop-2-ynyl, but-1-ynyl, but-2-ynyl, pent-1-ynyl, pent-2-ynyl, hex-1-ynyl, hex-2-ynyl, hex-3-ynyl. "Substituted alkynyl" refers to an alkynyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and R together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted.

The term "cycloalkyl" refers to a fully saturated cyclic hydrocarbon group containing from 1 to 4 rings and 3 to 8 carbons per ring. "$C_3$-$C_7$ cycloalkyl" refers to cyclopropyl, cyclobutyl, cyclopentyl, cyclohexyl, or cycloheptyl. "Substituted cycloalkyl" refers to a cycloalkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and R together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted. Exemplary substituents also include spiro-attached or fused cylic substitutents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc. "Substituted cycloalkenyl" refers to a cycloalkenyl group substituted with one more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and R together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted. Exemplary substituents also include spiro-attached or fused cylic substitutents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "aryl" refers to cyclic, aromatic hydrocarbon groups that have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1 to 3 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and R together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted. Exemplary substituents also include fused cylic groups, especially fused cycloalkyl, fused cycloalkenyl, fused heterocycle, or fused aryl, where the aforementioned cycloalkyl, cycloalkenyl, heterocycle and aryl substituents can themselves be optionally substituted.

The terms "heterocycle" and "heterocyclic" refer to fully saturated, or partially or fully unsaturated, including aromatic (i.e., "heteroaryl") cyclic groups (for example, 4 to 7 membered monocyclic, 7 to 11 membered bicyclic, or 8 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, benzo[d][1,3]dioxolyl, 2,3-dihydrobenzo[b][1,4]dioxinyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

"Substituted heterocycle" and "substituted heterocyclic" (such as "substituted heteroaryl") refer to heterocycle or heterocyclic groups substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and R together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted. Exemplary substituents also include spiro-attached or fused cylic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "alkylamino" refers to a group having the structure —NHR', wherein R' is hydrogen, alkyl or substituted alkyl, cycloalkyl or substituted cycloalkyl, as defined herein. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "dialkylamino" refers to a group having the structure —NRR', wherein R and R' are each independently alkyl or substituted alkyl, cycloalkyl or substituted cycloalkyl, cycloalkenyl or substituted cyclolalkenyl, aryl or substituted aryl, heterocylyl or substituted heterocyclyl, as defined herein. R and R' may be the same or different in an dialkyamino moiety. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

The terms "halogen" or "halo" refer to chlorine, bromine, fluorine or iodine.

Unless otherwise indicated, any heteroatom with unsatisfied valences is assumed to have hydrogen atoms sufficient to satisfy the valences.

The compounds of the present invention may form salts which are also within the scope of this invention. Reference to a compound of the present invention is understood to include reference to salts thereof, unless otherwise indicated. The term "salt(s)", as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the present invention may be formed, for example, by reacting a compound I with an amount of acid or base, such as an equivalent amount, in a medium such as one in which the salt precipitates or in an aqueous medium followed by lyophilization.

The compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of formula I which contain an acidic moiety, such but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Prodrugs and solvates of the compounds of the invention are also contemplated herein. The term "prodrug" as employed herein denotes a compound that, upon administration to a subject, undergoes chemical conversion by metabolic or chemical processes to yield a compound of the formula I, or a salt and/or solvate thereof. Solvates of the compounds of formula I include, for example, hydrates.

Compounds of the formula I, and salts or solvates thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the International Union of Pure and Applied Chemistry (IUPAC) 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

Compounds of the present invention are, subsequent to their preparation, preferably isolated and purified to obtain a composition containing an amount by weight equal to or greater than 90%, for example, equal to greater than 95%, equal to or greater than 99% formula I compound ("substantially pure" compound I), which is then used or formulated as described herein. Such "substantially pure" compounds of the present invention are also contemplated herein as part of the present invention.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclic rings.

Throughout the specifications, groups and substituents thereof may be chosen to provide stable moieties and compounds.

Definitions of specific functional groups and chemical terms are described in more detail below. For purposes of this invention, the chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

Compounds

Cyclosporin and its derivatives are potent inhibitors of viruses such as HIV, HBV and HCV. When an R-configuration substitute is introduced on the Sarcosine at the position 3 of cyclosporin, a high antiviral activity is obtained, which correlates into a high cyclophilin binding activity.

In one aspect, the present invention provides a method for treating or preventing hepatitis C virus infection or hepatitis B virus infection in a mammalian species in need thereof, the method comprising administering to the mammalian species a therapeutically effective amount of a compound of the formula (I):

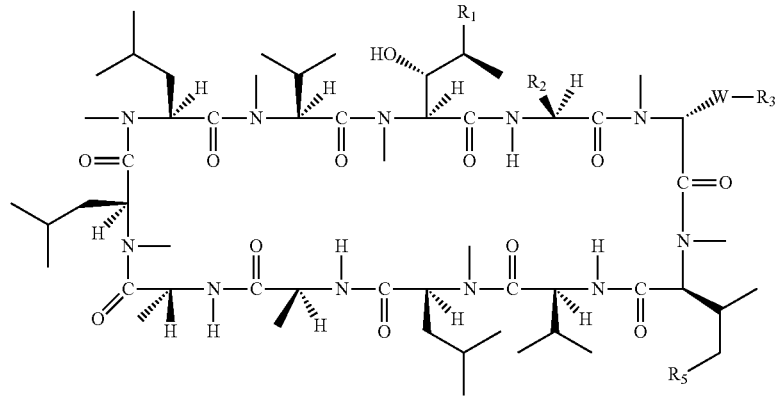

or pharmaceutically acceptable salt thereof, wherein the symbols have the following meanings and are, for each occurrence, independently selected:

$R_1$ is n-butyl or (E)-but-2-enyl;
$R_2$ is ethyl, 1-hydroxyethyl, isopropyl or n-propyl;
W is O, or S;
$R_3$ is alkyl or substituted alkyl, alkenyl or substituted alkenyl, alkynyl or substituted alkynyl, cycloalkyl or substituted cycloalkyl, or cycloalkenyl or substituted cycloalkenyl; and
$R_5$ is H or methyl.

In another aspect, the present invention provides a method for treating or preventing hepatitis C virus infection or hepatitis B virus infection in a mammalian species in need thereof, the method comprising administering to the mammalian species a therapeutically effective amount of a compound of the formula (I):

W is O, or S;
$R_3$ is:
  $(C_1-C_6)$alkyl, optionally substituted by one or more groups $R_4$ which may be the same or different;
  $(C_2-C_6)$alkenyl, optionally substituted by one or more groups which may be the same or different selected from halogen, hydroxy, amino, monoalkylamino and dialkylamino;
  $(C_2-C_6)$alkynyl, optionally substituted by one or one or more groups which may be the same or different selected from halogen, hydroxy, amino, monoalkylamino and dialkylamino; or
  $(C_3-C_7)$cycloalkyl, optionally substituted by one or more groups which may be the same or different selected from halogen, hydroxy, amino, monoalkylamino and dialkylamino;
$R_4$ is halogen, hydroxy, C(=O)$(C_1-C_6)$alkyl, C(=O)OH, C(=O)O$(C_1-C_6)$alkyl, —$NR_AR_B$; or —$NR_C(CH_2)_mNR_AR_B$;
each occurrence of $R_A$ and $R_B$ is independently:
  hydrogen;
  $(C_1-C_6)$alkyl, optionally substituted by one or more groups $R_D$ which may be the same or different;
  $(C_2-C_6)$alkenyl or $(C_2-C_6)$alkynyl;

(I)

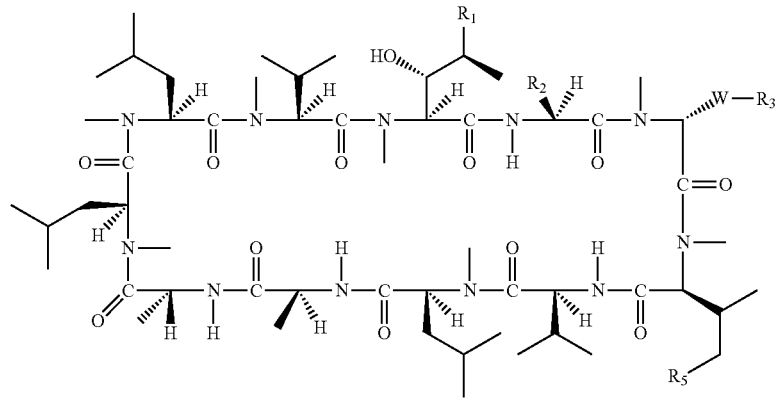

or pharmaceutically acceptable salt thereof, wherein the symbols have the following meanings and are, for each occurrence, independently selected:

$R_1$ is n-butyl or (E)-but-2-enyl;
$R_2$ is ethyl, 1-hydroxyethyl, isopropyl or n-propyl;

$(C_3-C_7)$cycloalkyl optionally substituted with $(C_1-C_6)$alkyl;
phenyl optionally substituted with from one to five groups which may be the same or different selected from halogen, —O($C_1$-$C_6$)alkyl, —C(=O)O($C_1$-$C_6$)alkyl, amino, alkylamino and dialkylamino; or a heterocyclic ring which may be saturated or unsaturated containing five or six ring atoms and from one to three heteroatoms which may the same or different selected from nitrogen, sulfur and oxygen;

or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;

each occurrence of $R_C$ is independently hydrogen or ($C_1$-$C_6$)alkyl;

each occurrence of $R_D$ is independently halogen, hydroxy, O($C_1$-$C_6$)alkyl, C(=O)($C_1$-$C_6$)alkyl, C(=O)O($C_1$-$C_6$)alkyl or —$NR_ER_F$;

each occurrence of $R_E$ and $R_F$ is independently hydrogen or ($C_1$-$C_6$)alkyl;

$R_5$ is H or methyl; and m is an integer of 2, 3, 4, or 5.

In certain embodiments, $R_1$ is n-butyl or

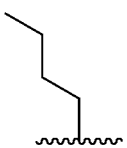

In certain other embodiments, $R_1$ is (E)-but-2-enyl or

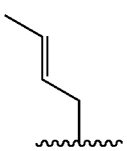

In certain embodiments, $R_2$ is ethyl. In certain other embodiments, $R_2$ is 1-hydroxyethyl. In yet other embodiments, $R_2$ is isopropyl. In yet other embodiments, $R_2$ is n-propyl.

In certain embodiments, W is O. In certain other embodiments, W is S, or W is C.

In certain embodiments, $R_5$ is H. In certain other embodiments, $R_5$ is methyl.

In certain embodiments, m is 2. In certain other embodiments, m is 3. In yet other embodiments, m is 4 or 5.

In certain embodiments, the compound has the following structure of formula (Ia):

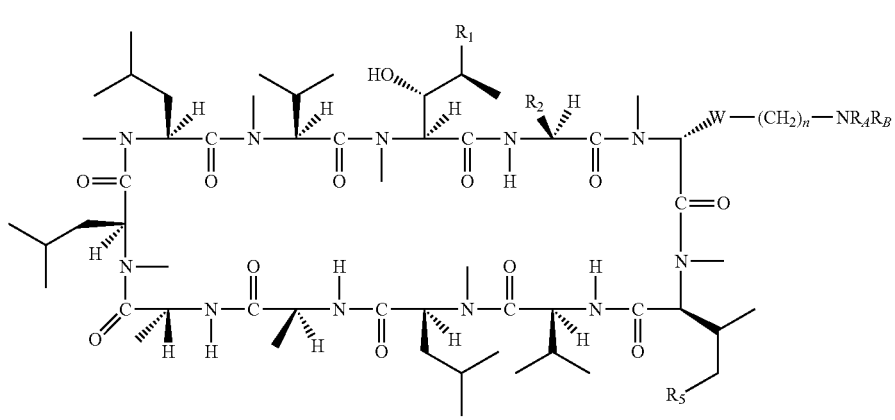

(Ia)

or pharmaceutically acceptable salt thereof, wherein the symbols are described herein.

In certain embodiments, $R_3$ is —$(CH_2)_nNR_AR_B$, wherein n is an integer of 2, 3, 4, 5, or 6; and wherein each occurrence of $R_A$ and $R_B$ is independently hydrogen; ($C_1$-$C_4$)alkyl, optionally substituted by one or more groups $R_D$ which may be the same or different, in which each occurrence of $R_D$ is independently halogen, hydroxy, O($C_1$-$C_4$)alkyl, C(=O)($C_1$-$C_4$)alkyl, C(=O)O($C_1$-$C_4$)alkyl; or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from ($C_1$-$C_4$)alkyl, phenyl and benzyl.

In certain embodiments, $R_3$ is —$(CH_2)_nNR_AR_B$, wherein n is an integer of 2, 3, 4, 5, or 6; and wherein $R_A$ and $R_B$, together with the nitrogen atom to which they are attached, form a saturated or unsaturated heterocyclic ring containing from three to seven ring atoms, which ring may optionally contain another heteroatom selected from nitrogen, oxygen and sulfur and may be optionally substituted by from one to four groups which may be the same or different selected from ($C_1$-$C_4$)alkyl, phenyl and benzyl.

In certain embodiments, n is 2. In certain other embodiments, n is 3. In yet other embodiments, n is 4, 5, or 6.

In certain embodiments, $R_3$ is 2-aminoethyl, 2-aminopropyl, 3-aminopropyl, 2-monoalkylaminoethyl, 2-monoalkylaminopropyl, 3-monoalkylaminopropyl, 2-dialkylaminoethyl, 2-dialkylaminopropyl, or 3-dialkylaminopropyl, wherein said alkyl is ($C_1$-$C_4$)alkyl.

In certain embodiments, $R_3$ is 2-aminoethyl, 2-aminopropyl, 3-aminopropyl, 2-monoalkylaminoethyl, 2-monoalkylaminopropyl, 3-monoalkylaminopropyl, 2-dialkylaminoethyl, 2-dialkylaminopropyl, or 3-dialkylaminopropyl, wherein said alkyl is ($C_1$-$C_4$)alkyl. wherein $R_3$ is dimethylaminoethyl, diethylaminoethyl, methylethylaminoethyl, methyl-iso-butylaminoethyl, ethyl-iso-butylaminoethyl, methyl-tert-butylaminoethyl, or ethyl-tert-butylaminoethyl.

In certain embodiments, $R_3$ is

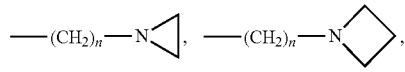

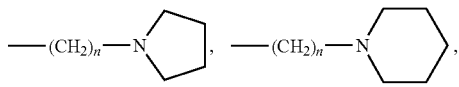

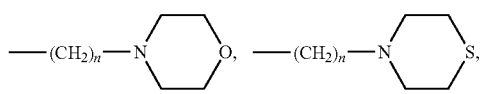

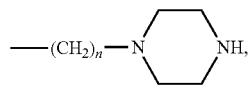

-continued

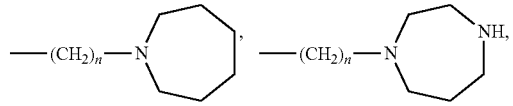

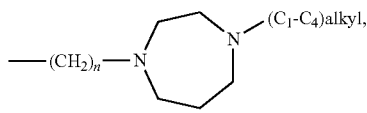

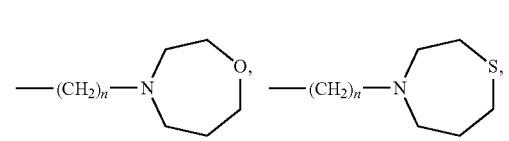

in which n is an integer of 2, 3, 4, 5, or 6. In certain embodiments, n is 2. In certain other embodiments, n is 3. In yet other embodiments, n is 4, or 5, or 6.

In certain embodiments, the compound has the following chemical structure:

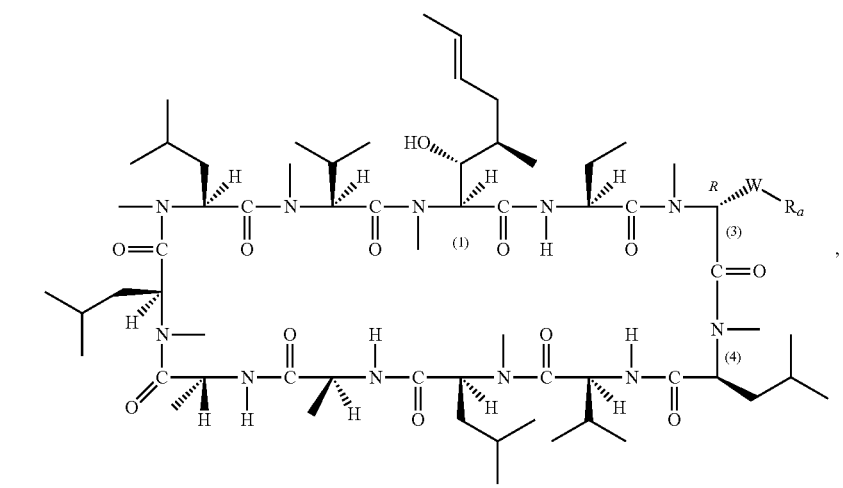

(II)

wherein W is S or O;

$R_a$ is methyl, ethyl, n-propyl, i-propyl, n-butyl, i-butyl, t-butyl, $CH_2CMe_3$, phenyl, $CH_2$-phenyl,

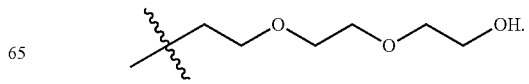

In certain other embodiments, the compound has the following chemical structure:

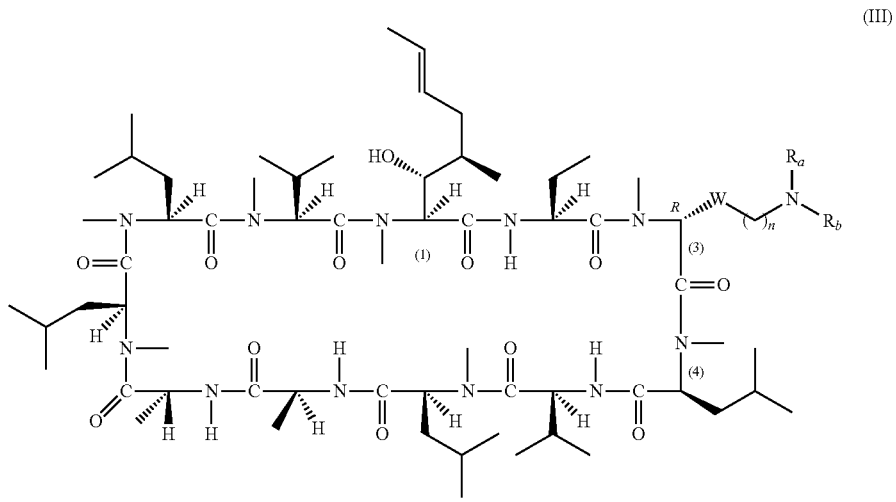

(III)

wherein n is 2, 3, 4, 5, or 6;

$R_a$ is methyl, ethyl, n-propyl, i-propyl, n-butyl, i-butyl, t-butyl, $CH_2CMe_3$, phenyl, or $CH_2$-phenyl; and $R_b$ is H, n-propyl, i-propyl, n-butyl, i-butyl, t-butyl, $CH_2CMe_3$, phenyl, or $CH_2$-phenyl;

or

is

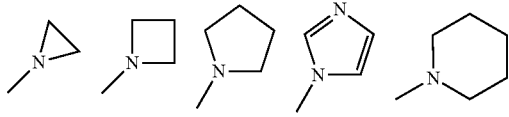

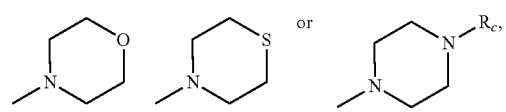

in which $R_c$ is H, methyl, ethyl, n-propyl, i-propyl, n-butyl, i-butyl, t-butyl, $CH_2CMe_3$, phenyl, or $CH_2$-phenyl.

In yet other embodiments, the compound has the following chemical structure:

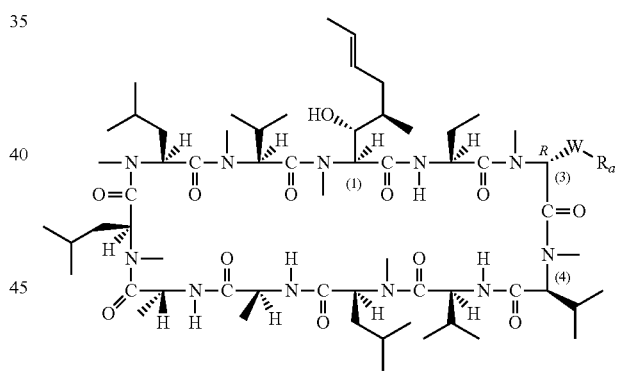

(IV)

wherein W is S or O; and $R_a$ is methyl, ethyl, n-propyl, i-propyl, n-butyl, i-butyl, t-butyl, $CH_2CMe_3$, phenyl, $CH_2$-phenyl,

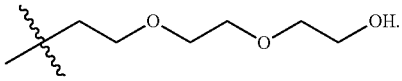

In yet other embodiments, the compound has the following chemical structure:

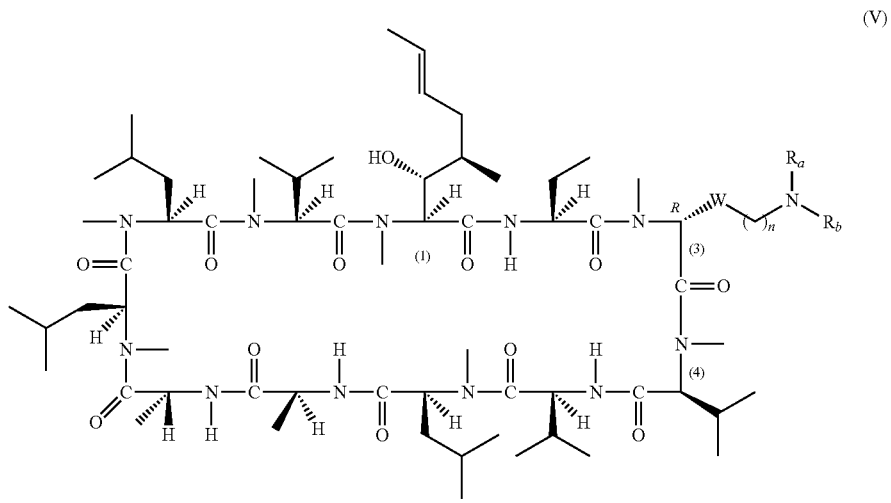

(V)

wherein W is S or O;

n is 2, 3, 4, 5, or 6;

$R_a$ is H, methyl, ethyl, n-propyl, i-propyl, n-butyl, i-butyl, t-butyl, $CH_2CMe_3$, phenyl, or $CH_2$-phenyl; and $R_b$ is H, n-propyl, i-propyl, n-butyl, i-butyl, t-butyl, $CH_2CMe_3$, phenyl, or $CH_2$-phenyl;

or

is

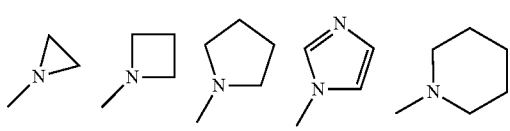

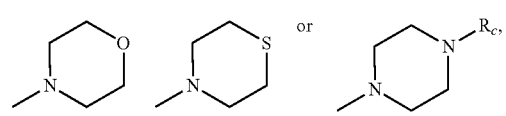

in which $R_c$ is H, methyl, ethyl, n-propyl, i-propyl, n-butyl, i-butyl, t-butyl, $CH_2CMe_3$, phenyl, or $CH_2$-phenyl.

In yet other embodiments, the compound has the following chemical structure:

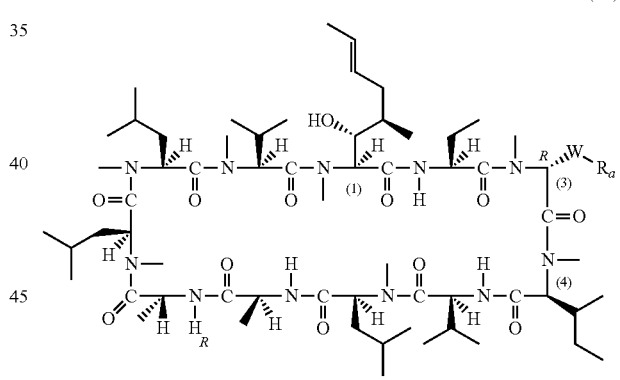

(VI)

wherein W is S or O;

$R_a$ is methyl, ethyl, n-propyl, i-propyl, n-butyl, i-butyl, t-butyl, $CH_2CMe_3$, phenyl, $CH_2$-phenyl,

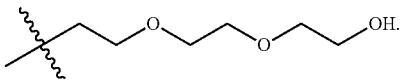

In yet other embodiments, the compound has the following chemical structure:

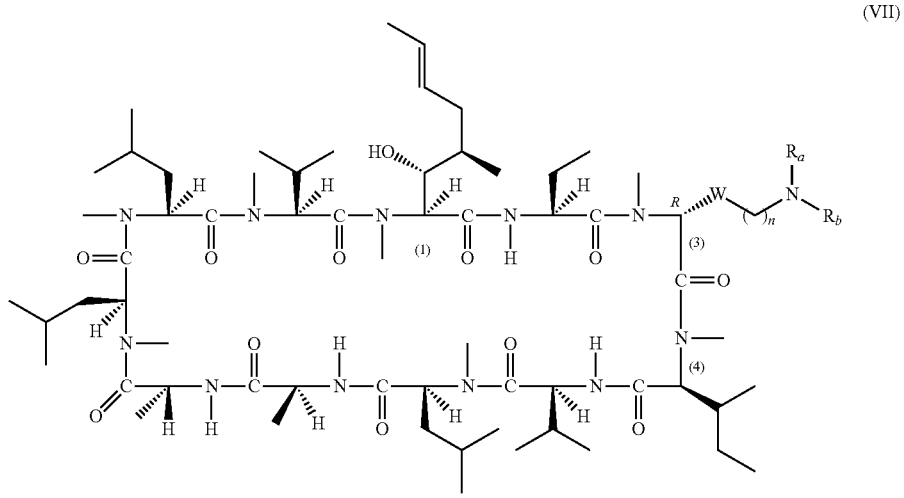

(VII)

wherein W is S or O;

n is 2, 3, 4, 5, or 6;

$R_a$ is H, methyl, ethyl, n-propyl, i-propyl, n-butyl, i-butyl, t-butyl, $CH_2CMe_3$, phenyl, or $CH_2$-phenyl; and $R_b$ is H, n-propyl, i-propyl, n-butyl, i-butyl, t-butyl, $CH_2CMe_3$, phenyl, or $CH_2$-phenyl;

or

is

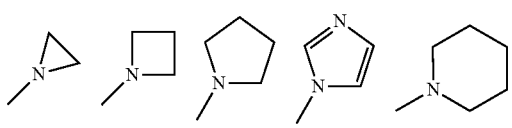

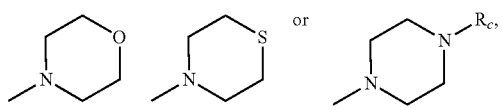

in which $R_c$ is H, methyl, ethyl, n-propyl, i-propyl, n-butyl, i-butyl, t-butyl, $CH_2CMe_3$, phenyl, or $CH_2$-phenyl.

In yet other embodiments, the compound is:

[(R)-2-(N,N-Diethylamino)ethylthio-Sar]-3-cyclosporin;

[(R)-2-(N-iso-Propyl-N-ethylamino)ethylthio-Sar]-3-cyclosporin;

[(R)-2-(N,N-Diethylamino)ethylthio-Sar]-3-[N-MeIle]-4-cyclosporin;

[(R)-3-(N,N-Diethylamino)propylthio-Sar]-3-[N-MeIle]-4-cyclosporin;

[(R)-3-(N-Morpholino)propyl-Sar]-3-[N-MeIle]-4-cyclosporin;

[(R)-3-(N-Pyrrolidinyl)propylthio-Sar]-3-[N-MeIle]-4-cyclosporin;

[(R)-3-(N-Piperidinyl)propylthio-Sar]-3-[N-MeIle]-4-cyclosporin;

[(R)-3-(N-4-Methylpiperazinyl)propylthio-Sar]-3-[N-MeIle]-4-cyclosporin;

[(R)-3-(N,N-Diethylamino)propylthio-Sar]-3-[N-MeVal]-4-cyclosporin;

[(R)-3-(N-Morpholino)propyl-Sar]-3-[N-MeVal]-4-cyclosporin;

[(R)-3-(N-Pyrrolidinyl)propylthio-Sar]-3-[N-MeVal]-4-cyclosporin;

[(R)-3-(N-Piperidinyl)propylthio-Sar]-3-[N-MeVal]-4-cyclosporin; or

[(R)-3-(N-4-Methylpiperazinyl)propylthio-Sar]-3-[N-MeVal]-4-cyclosporin, or pharmaceutically acceptable salt thereof.

In another aspect, the present invention provides a compound of formula (Ia):

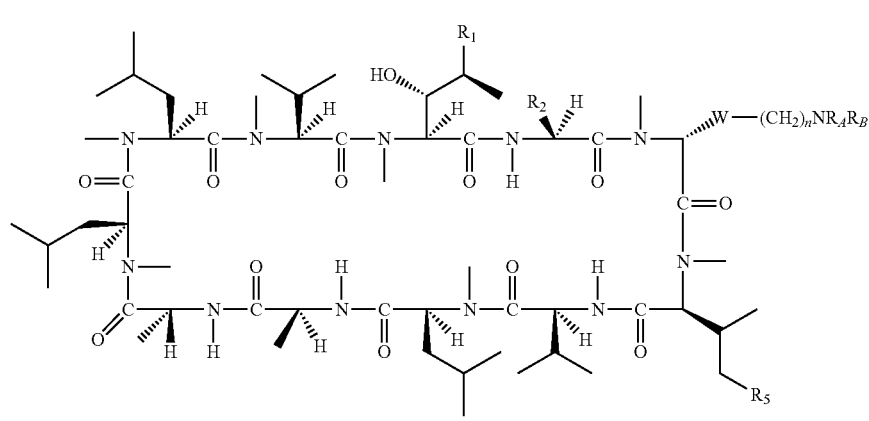

or pharmaceutically acceptable salt thereof, wherein the symbols have the following meanings and are, for each occurrence, independently selected:

$R_1$ is n-butyl or (E)-but-2-enyl;

$R_2$ is ethyl, 1-hydroxyethyl, isobutyl or n-butyl;

W is O or S;

n is an integer of 3, 4, 5 or 6;

each occurrence of $R_A$ and $R_B$ is independently hydrogen; $(C_1-C_4)$alkyl, optionally substituted by one or more groups $R_D$ which may be the same or different, in which each occurrence of $R_D$ is independently halogen, hydroxy, $O(C_1-C_4)$alkyl, $C(=O)(C_1-C_4)$alkyl, $C(=O)O(C_1-C_4)$alkyl; or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from $(C_1-C_4)$alkyl, phenyl and benzyl.

$R_1$ is n-butyl.

In certain embodiments, $R_1$ is n-butyl. In certain other embodiments, $R_1$ is (E)-but-2-enyl.

In certain embodiments, $R_2$ is ethyl.

In certain embodiments, W is O. In certain other embodiments, W is S.

In certain embodiments, each occurrence of $R_A$ and $R_B$ is independently hydrogen or $(C_1-C_4)$alkyl. In certain other embodiments, $R_A$ and $R_B$, together with the nitrogen atom to which they are attached, form a saturated or unsaturated heterocyclic ring containing from three to seven ring atoms, which ring may optionally contain another heteroatom selected from nitrogen, oxygen and sulfur and may be optionally substituted by from one to four groups which may be the same or different selected from $(C_1-C_4)$alkyl, phenyl and benzyl.

In yet other embodiments, $(CH_2)_nR_AR_B$ is selected from

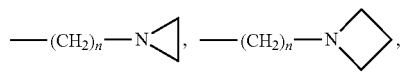

-continued

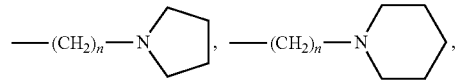

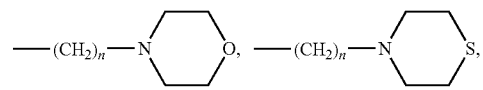

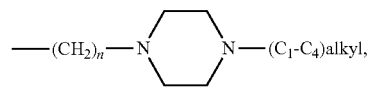

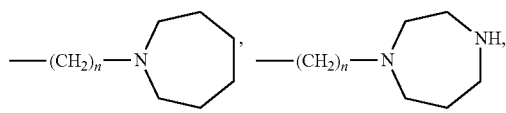

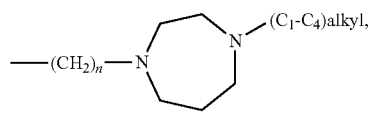

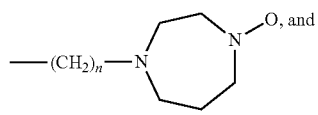

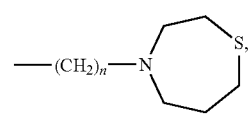

in which n is an integer of 3, 4, 5 or 6.

In certain embodiments, $R_5$ is H. In certain other embodiments, $R_5$ is methyl.

In one aspect, the present invention provides a compound of formula (II), or pharmaceutically acceptable salt thereof,

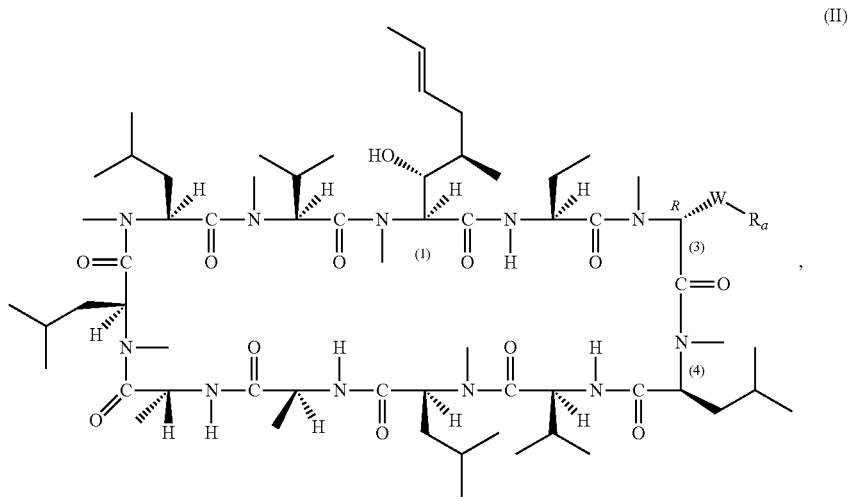

(II)

wherein W is S or O;
$R_a$ is methyl, ethyl, n-propyl, i-propyl, n-butyl, i-butyl, t-butyl, $CH_2CMe_3$, phenyl, $CH_2$-phenyl,

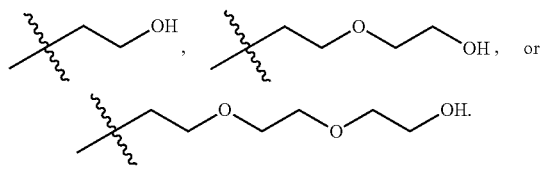

wherein W is S or O;
n is 3, 4, 5, or 6;
$R_a$ is methyl, ethyl, n-propyl, i-propyl, n-butyl, i-butyl, t-butyl, $CH_2CMe_3$, phenyl, or $CH_2$-phenyl; and
$R_b$ is H, n-propyl, i-propyl, n-butyl, i-butyl, t-butyl, $CH_2CMe_3$, phenyl, or $CH_2$-phenyl;
or

In another aspect, the present invention provides a compound of formula (III), or pharmaceutically acceptable salt thereof,

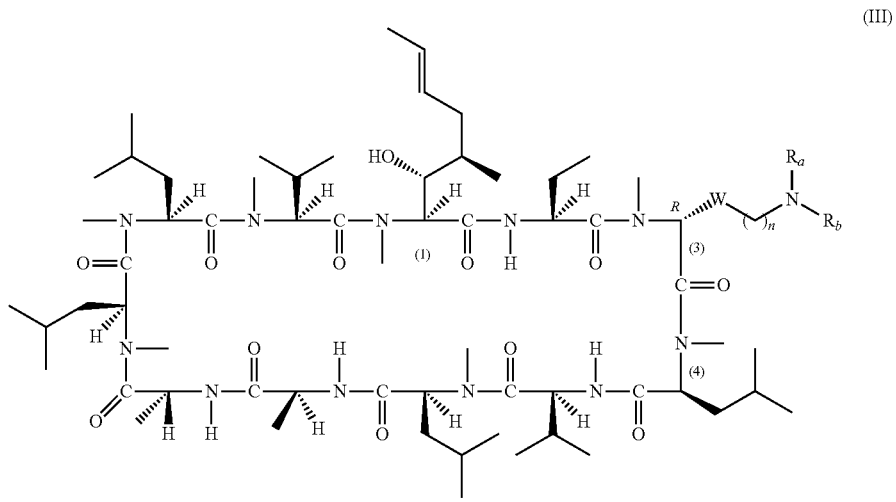

(III)

is

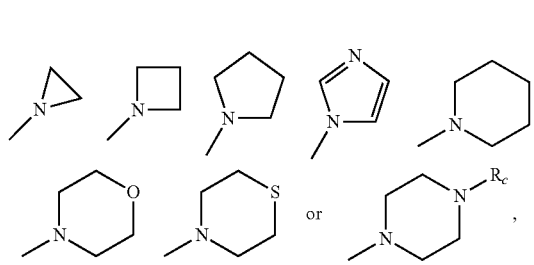

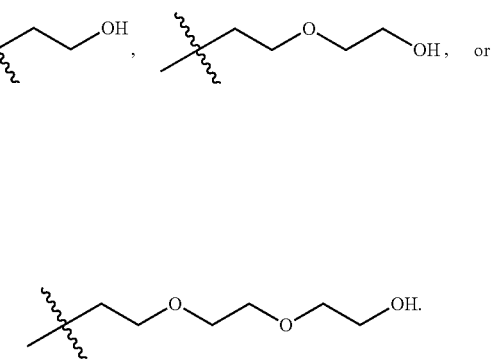

in which $R_c$ is H, methyl, ethyl, n-propyl, i-propyl, n-butyl, i-butyl, t-butyl, $CH_2CMe_3$, phenyl, or $CH_2$-phenyl.

In yet another aspect, the present invention provides a compound of formula (IV), or pharmaceutically acceptable salt thereof, (IV)

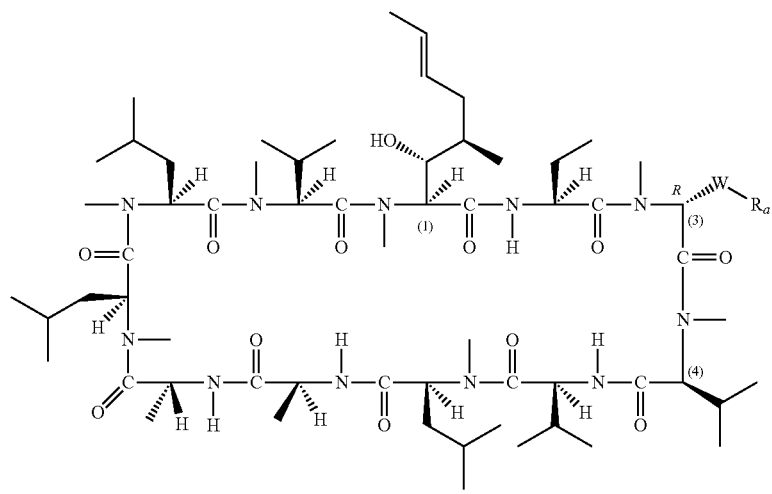

wherein W is S or O; and $R_a$ is methyl, ethyl, n-propyl, i-propyl, n-butyl, i-butyl, t-butyl, $CH_2CMe_3$, phenyl, $CH_2$-phenyl, In yet another aspect, the present invention provides a compound of formula (V), or pharmaceutically acceptable salt thereof, (V)

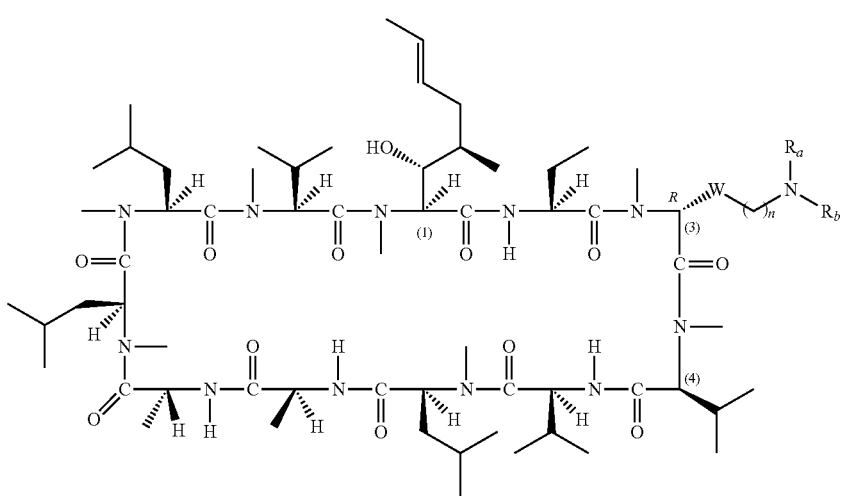

wherein W is S or O;

n is 3, 4, 5, or 6;

$R_a$ is H, methyl, ethyl, n-propyl, i-propyl, n-butyl, i-butyl, t-butyl, $CH_2CMe_3$, phenyl, or $CH_2$-phenyl; and $R_b$ is H, n-propyl, i-propyl, n-butyl, i-butyl, t-butyl, $CH_2CMe_3$, phenyl, or $CH_2$-phenyl;

or

is

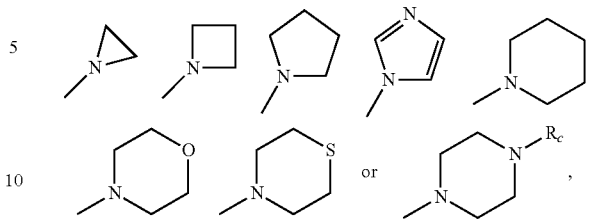

in which $R_c$ is H, methyl, ethyl, n-propyl, i-propyl, i-butyl, t-butyl, $CH_2CMe_3$, phenyl, or $CH_2$-phenyl.

In yet another aspect, the present invention provides a compound of formula (VI), or pharmaceutically acceptable salt thereof,

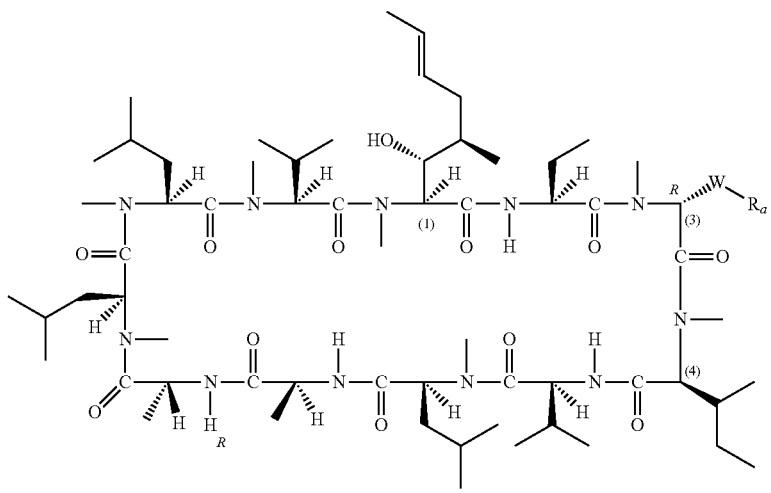

wherein W is S or O;

$R_a$ is methyl, ethyl, n-propyl, i-propyl, n-butyl, i-butyl, t-butyl, $CH_2CMe_3$, phenyl, $CH_2$-phenyl,

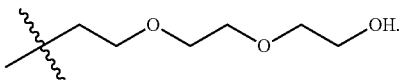

In yet another aspect, the present invention provides a compound of formula (VII), or pharmaceutically acceptable salt thereof, (VII)

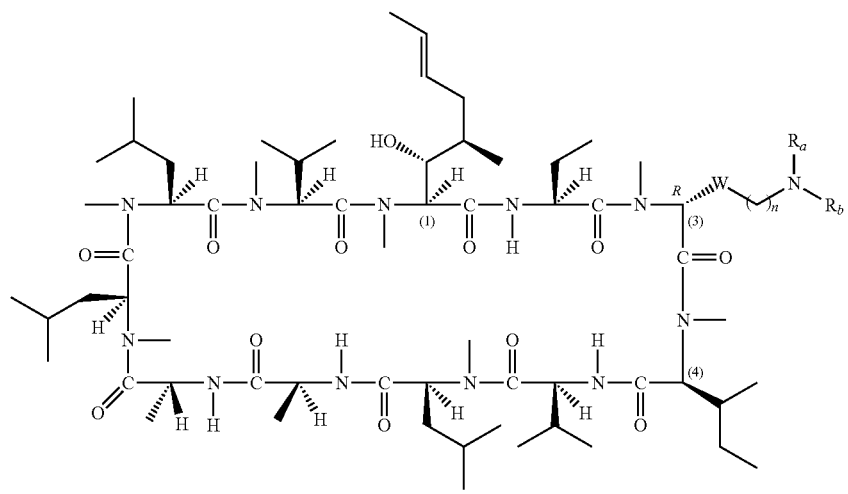

wherein W is S or O;
n is 3, 4, 5, or 6;
$R_a$ is H, methyl, ethyl, n-propyl, i-propyl, n-butyl, i-butyl, t-butyl, $CH_2CMe_3$, phenyl, or $CH_2$-phenyl; and
$R_b$ is H, n-propyl, i-propyl, n-butyl, i-butyl, t-butyl, $CH_2CMe_3$, phenyl, or $CH_2$-phenyl;
or

is

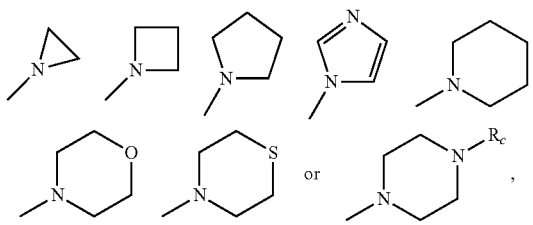

in which $R_c$ is H, methyl, ethyl, n-propyl, i-propyl, n-butyl, i-butyl, t-butyl, $CH_2CMe_3$, phenyl, or $CH_2$-phenyl.

In one aspect, the present invention provides a compound selected from Examples 1-496, or pharmaceutically acceptable salt thereof.

In another aspect, the present invention provides a compound selected from:
[(R)-2-(N,N-Diethylamino)ethylthio-Sar]-3-cyclosporin;
[(R)-2-(N-iso-Propyl-N-ethylamino)ethylthio-Sar]-3-cyclosporin;
[(R)-2-(N,N-Diethylamino)ethylthio-Sar]-3-[N-MeIle]-4-cyclosporin;
[(R)-3-(N,N-Diethylamino)propylthio-Sar]-3-[N-MeIle]-4-cyclosporin;
[(R)-3-(N-Morpholino)propyl-Sar]-3-[N-MeIle]-4-cyclosporin;
[(R)-3-(N-Pyrrolidinyl)propylthio-Sar]-3-[N-MeIle]-4-cyclosporin;
[(R)-3-(N-Piperidinyl)propylthio-Sar]-3-[N-MeIle]-4-cyclosporin;
[(R)-3-(N-4-Methylpiperazinyl)propylthio-Sar]-3-[N-MeIle]-4-cyclosporin;
[(R)-3-(N,N-Diethylamino)propylthio-Sar]-3-[N-MeVal]-4-cyclosporin;
[(R)-3-(N-Morpholino)propyl-Sar]-3-[N-MeVal]-4-cyclosporin;
[(R)-3-(N-Pyrrolidinyl)propylthio-Sar]-3-[N-MeVal]-4-cyclosporin;
[(R)-3-(N-Piperidinyl)propylthio-Sar]-3-[N-MeVal]-4-cyclosporin; and
[(R)-3-(N-4-Methylpiperazinyl)propylthio-Sar]-3-[N-MeVal]-4-cyclosporin, or
pharmaceutically acceptable salt thereof.

In yet another aspect, the present invention provides a pharmaceutical composition comprising at least one compound described herein and a pharmaceutically-acceptable carrier or diluent.

In a further aspect, the present invention provides a method for treating or preventing a viral infection in a mammalian species in need thereof, the method comprising administering to the mammalian species a therapeutically effective amount of at least one compound described herein. In certain embodiments, the viral infection is HIV infection. In certain other embodiments, the viral infection is HBV infection. In yet other embodiments, the viral infection is HCV infection. In yet other embodiments, the viral infection is influenza A virus infection, severe acute respiratory syndrome coronavirus infection or vaccinia virus infection. In yet other embodiments, the viral infection is herpes simplex virus.

In another aspect, the present invention provides a method for treating or preventing hepatitis C virus or hepatitis B virus infection in a mammalian species in need thereof, the method comprising administering to the mammalian species a therapeutically effective amount of at least one compound described herein.

In another aspect, the present invention provides a method for treating or preventing a central nervous system disorder in a mammalian species in need thereof, the method comprising administering to the mammalian species a therapeutically effective amount of at least one compound described herein. In certain embodiments, the central nervous system disorder is mitochondrial protection for stroke, traumatic brain and spinal cord injury, Alzheimer, Parkinson's Disease, or Huntington's Diseases.

In yet another aspect, the present invention provides a method for treating or preventing a cardiovascular disease in a mammalian species in need thereof, the method comprising administering to the mammalian species a therapeutically effective amount of at least one compound described herein. In certain embodiments, the cardiovascular disease is reperfusion injury, heart attack, or chronic heart failure.

In yet another aspect, the present invention provides a method for treating or preventing an inflammation disease in a mammalian species in need thereof, the method comprising administering to the mammalian species a therapeutically effective amount of at least one compound described herein. In certain embodiments, the inflammation disease is respiratory inflammation, asthma, ulcerative colitis, rheumatoid arthritis, or dry eye disease.

Methods of Preparation

The NIM-811 (N-MeIle-4-Cyclosporin) and SDZ 220-384 (N-MeVal-4-Cyclosporin) were prepared by selectively open Cylosporin A ring between position 3 and 4 (Papageorgiou C. et al., 1994, *J. Med. Chem.*, 37, 3674-3676 and its reference 11: Su, Z., Wenger, R. Unpublished results; Papageorgiou C. et al., 1994, *Bioorg & Med Chem Lett*, 4. 267-272 and its reference 14: Su, Z., Wenger, R. Unpublished results; each of which is incorporated herein by reference). Debio-025, an antiviral non-immunosuppressive cyclosporine derivative, was synthesized by using this methodology as a key step (PCT/IB2005/003205, U.S. Pat. Nos. 6,927,208, 7,439,227, WO 2000/01715, WO 2006/038088; each of which is incorporated herein by reference).

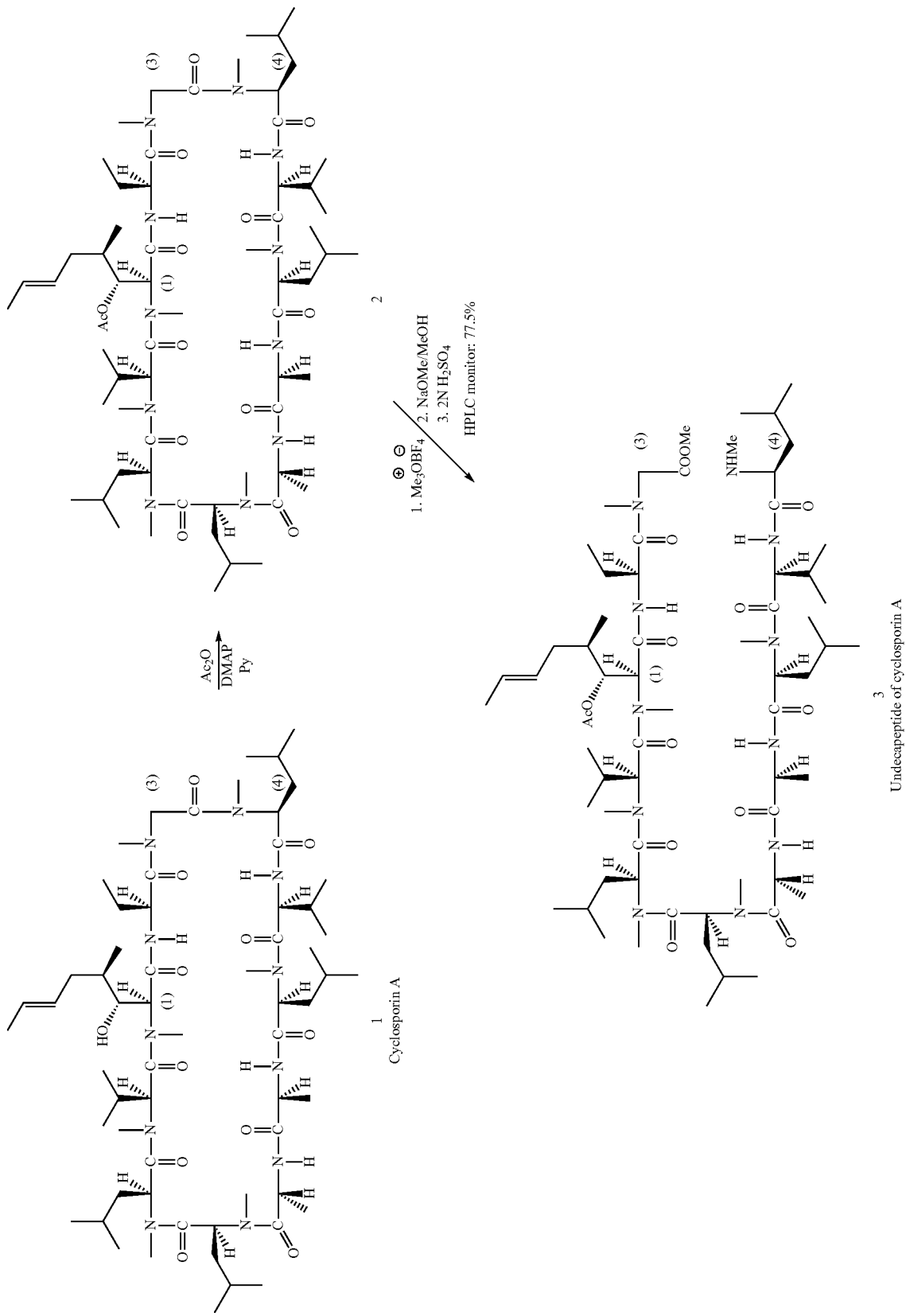

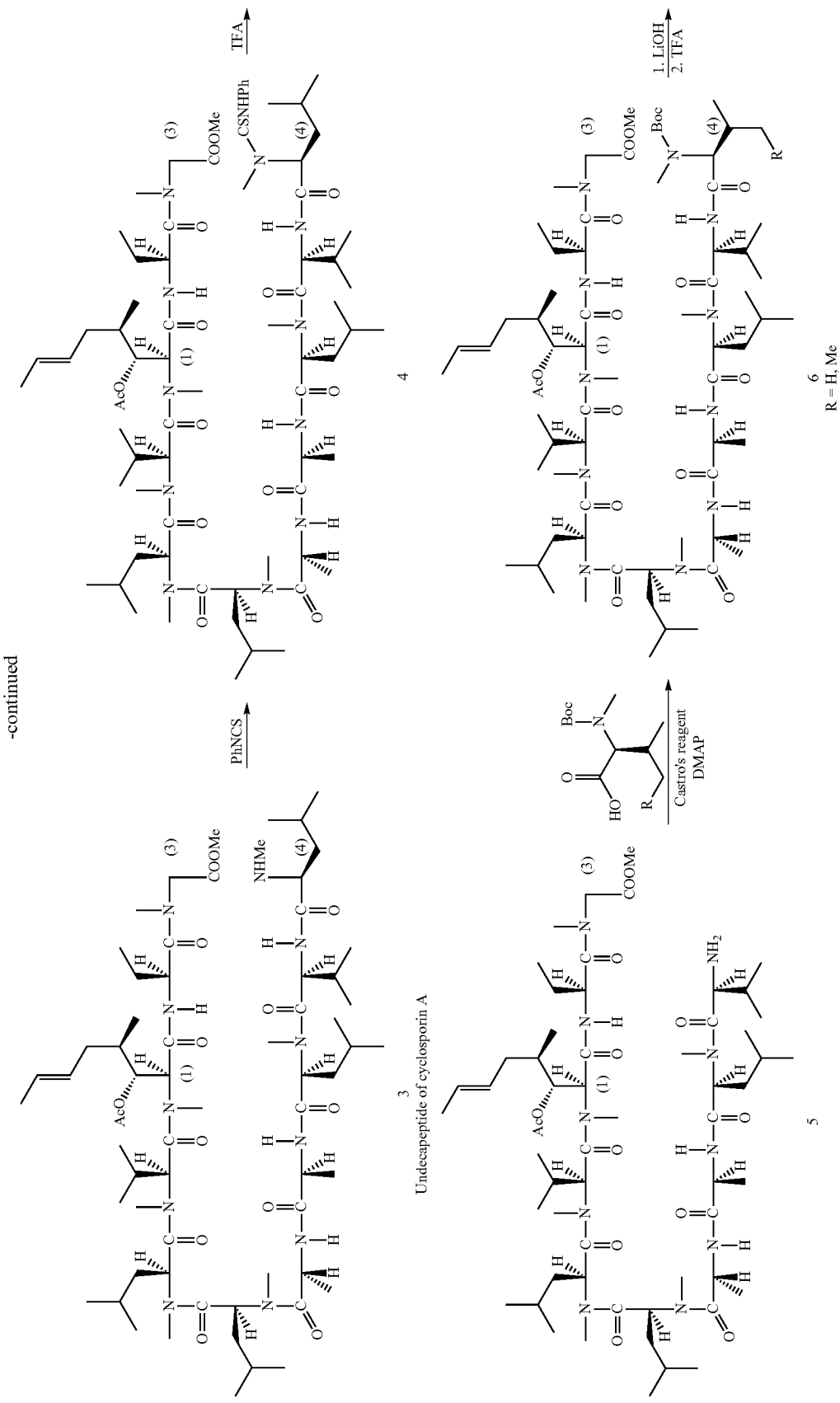

-continued
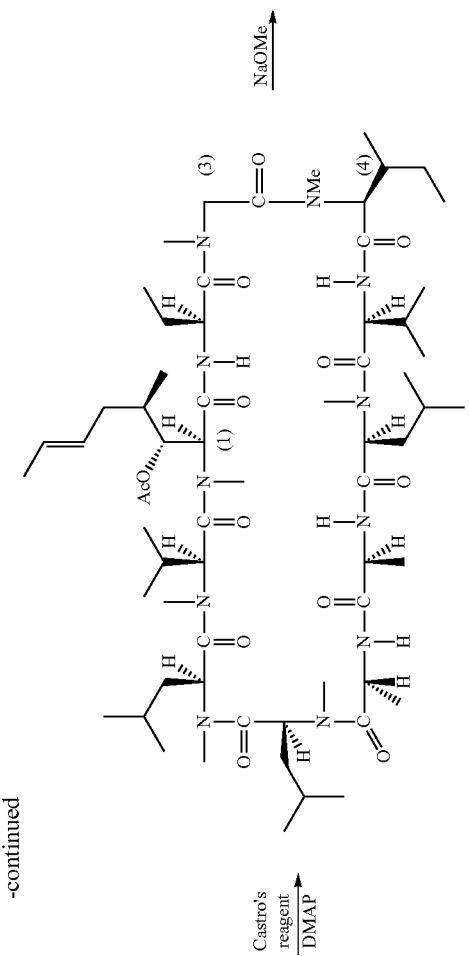
8
R = H, Me
Castro's reagent / DMAP →
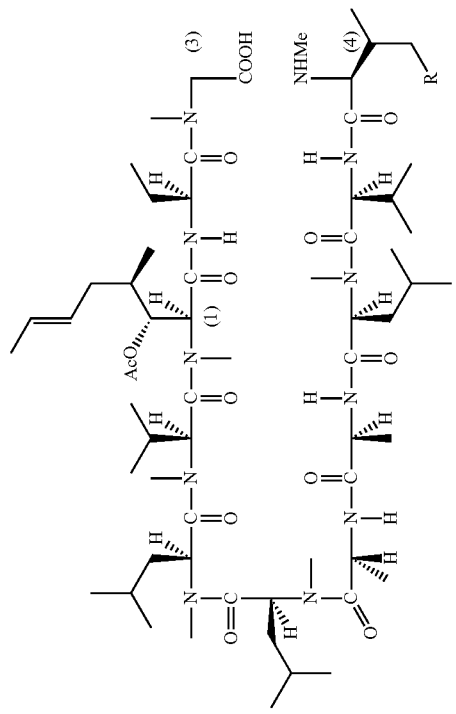
7
R = H, Me
NaOMe →
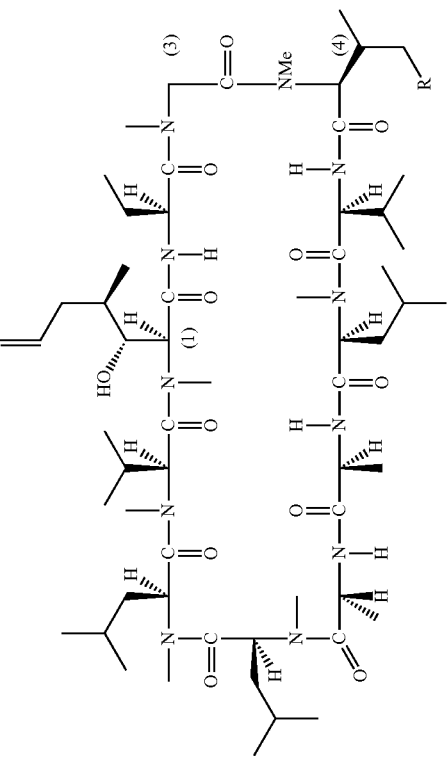
9
R = H SDZ-220-384, N-MeVal-4-Cyclosporin
R = Me SDZ-NIM-811, N-MeIle-4-Cyclosporin The derivatives on the sarcosine of position 3 of NIM-811 and SDZ 220-384 (formula (I)) can be prepared by using Dr. Dieter Seebach's method to generate the enolate at the sarcosine with a base (e.g., LDA), and then the enolate was trapped by disulphide electrophile to form the thioether side chain (Seebach D. et al., 1993, *Helv. Chim. Acta,* 76, 1564-1590; U.S. Pat. Nos. 6,583,265, 7,718,767; each of which is incorporated herein by reference).

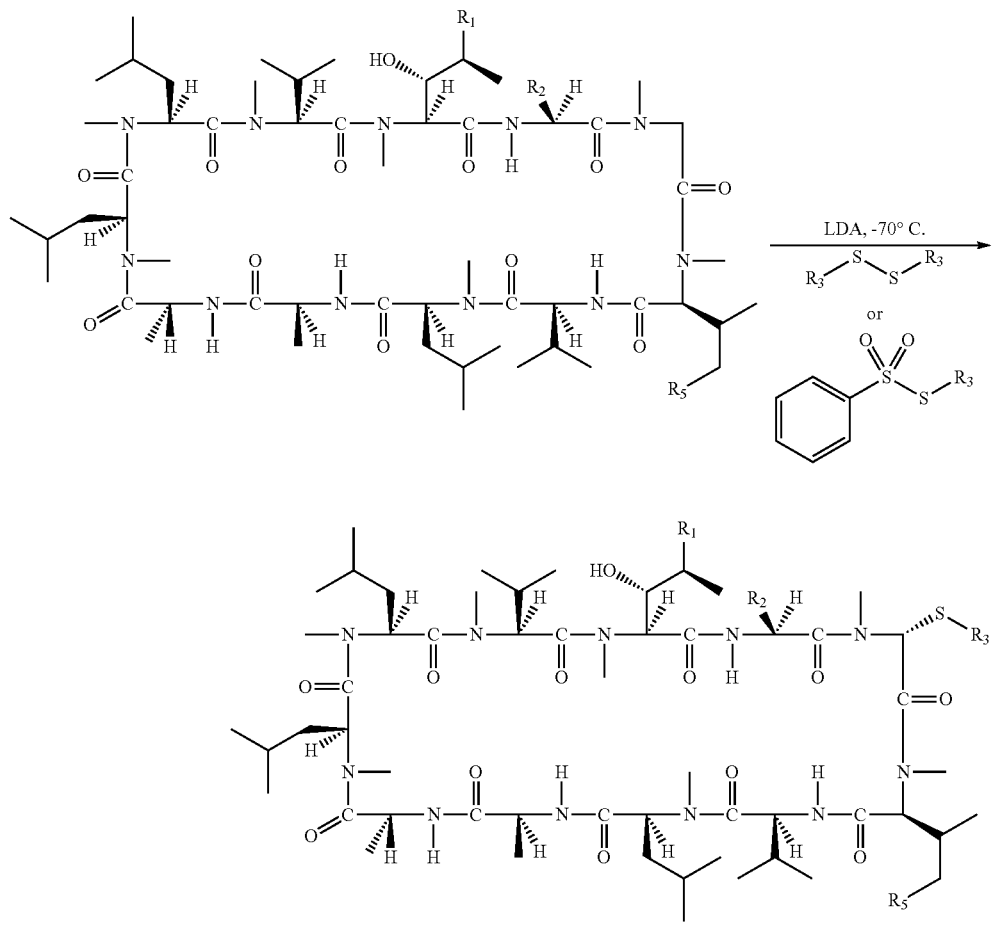

The ether side chain on the sarcosine of cyclosporin at position 3 was reported by C-Chem and Scynexis by using the similar method, which the thioether side chain had been introduced in the first step, and then exchanged to ether side chain (U.S. Pat. Nos. 6,583,265, 7,718,767; each of which is incorporated herein by reference).

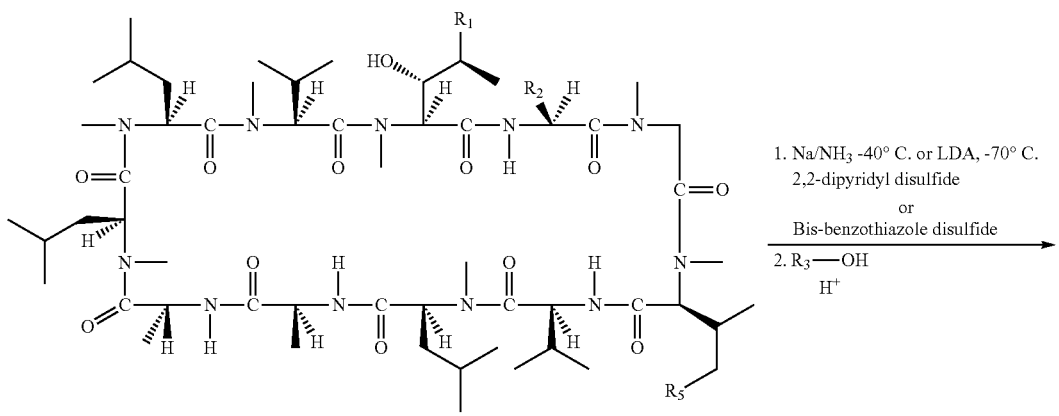

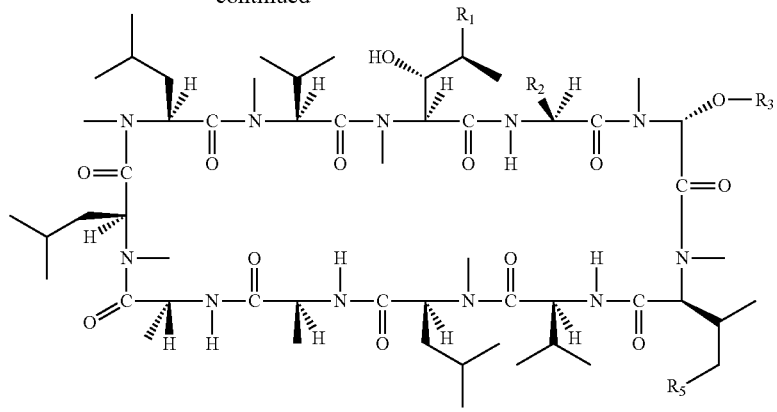

The hydrogenation of double bond on the MeBmt at cyclosporine position 1 gave the (Dihydro-MeBmt)-1-cyclosporin as described by former Sandoz and Novartis patents (U.S. Pat. Nos. 4,108,985, 5,767,069, and 5,981,479, each of which is incorporated herein by reference).

Pharmaceutical Compositions

This invention also provides a pharmaceutical composition comprising at least one of the compounds as described herein or a pharmaceutically-acceptable salt or solvate thereof, and a pharmaceutically-acceptable carrier.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as butylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As set out above, certain embodiments of the present pharmaceutical agents may be provided in the form of pharmaceutically-acceptable salts. The term "pharmaceutically-acceptable salt", in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al., (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, butionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate, magnesium stearate, and polyethylene oxide-polybutylene oxide copolymer as well as coloring agents, release agents, coating agents, sweetening, flavoring and perfuming agents, preservatives and antioxidants can also be present in the compositions.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of 100%, this amount will range from about 1% to about 99% of active ingredient, preferably from about 5% to about 70%, most preferably from about 10% to about 30%.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polybutylene oxide copolymer; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxybutylmethyl cellulose), lubricant, inert diluent, preservative, disintegrant (for example, sodium starch glycolate or cross-linked sodium carboxymethyl cellulose), surface-active or dispersing agent. Molded tablets, may be, made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxybutylmethyl cellulose in varying butortions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if apbutriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isobutyl alcohol, ethyl carbonate, ethyl acetate, benzyl alcohol, benzyl benzoate, butylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g., hydroxybutyl-.beta.-cyclodextrin, may be used to solubilize compounds.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active pharmaceutical agents of the invention.

Formulations of the present invention which are suitable for vaginal administration also include pessaries, tampons, creams, gels, pastes, foams or spray formulations containing such carriers as are known in the art to be apbutriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or butellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary butellants, such as chlorofluorohydrocarbons and volatile unsubstituted hydrocarbons, such as butane and butane.

Transdermal patches have the added advantage of providing controlled delivery of a compound of the present invention to the body. Such dosage forms can be made by dissolving, or dispersing the pharmaceutical agents in the buter medium. Absorption enhancers can also be used to increase the flux of the pharmaceutical agents of the invention across the skin. The rate of such flux can be controlled, by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle. One strategy for depot injections includes the use of polyethylene oxide-polybutylene oxide copolymers wherein the vehicle is fluid at room temperature and solidifies at body temperature.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly (anhydrides). Depot injectable formulations are also prepared by entrapping the drug in liposomes or microemulsions, which are compatible with body tissue.

When the compounds of the present invention are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, the compound of the present invention may be administered concurrently with another anti-HCV agent), or they may achieve different effects (e.g., control of any adverse effects).

The compounds of the invention may be administered intravenously, intramuscularly, intraperitoneally, subcutaneously, topically, orally, or by other acceptable means. The compounds may be used to treat arthritic conditions in mammals (i.e., humans, livestock, and domestic animals), birds, lizards, and any other organism, which can tolerate the compounds.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Equivalents

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional information, exemplification and guidance which can be adapted to the practice of this invention in its various embodiments and equivalents thereof.

EXAMPLES

Example 1

[(R)-2-(N,N-Diethylamino)ethylthio-Sar]-3-[N-methylvaline]-4-cyclosporin

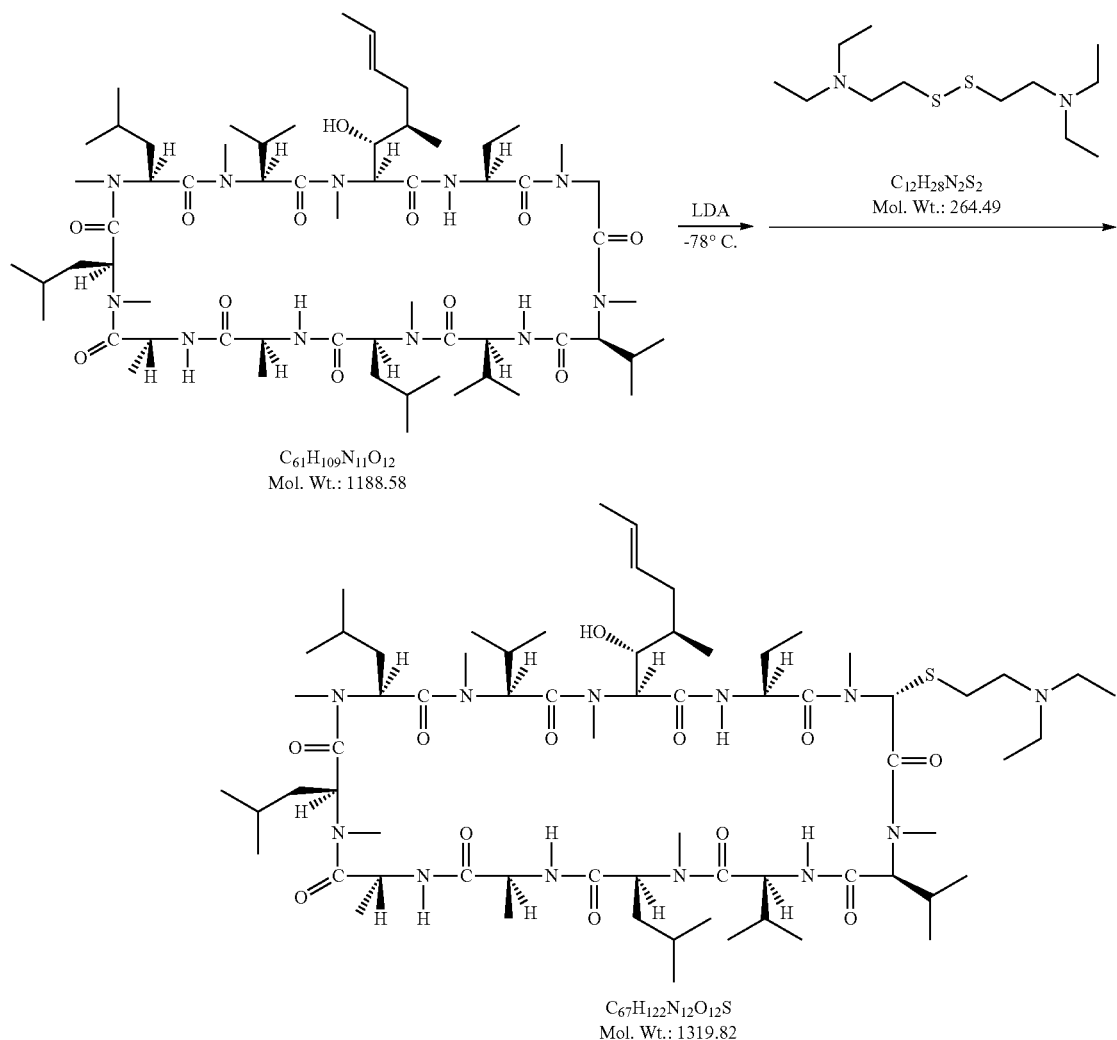

The LDA was prepared by adding diisopropylamine (0.89 ml, 6.31 mmol, 15 equiv), followed by n-butyllithium (2.87 M, 6.3 mmol, 2.20 ml, 15 eqiv.) to 20 ml of THF at −78° C. under nitrogen. The LDA solution was stirred for an hour and then a solution of N-MeVal-4-Cyclosporin (0.5 g, 0.42 mmol) in 5 ml of THF was dropwise added during 5-10 min below −65° C. The mixture was stirred at −78° C. for 2 hrs. Bis[2-(N,N-diethylamino)ethyl]disulfide (2.15 g, 8.13 mmol) dissolved in 5 ml of THF was added at −70° C. and the mixture was kept stirring at −70° C. for additional two hours. The cooling bath was removed and the mixture was allowed to warm up to room temperature for one hour under stirring. The reaction was quenched by the addition of citric acid and then THF was removed under vacuum. The residue was extracted with methylene chloride (3×25 ml) and the organic phase was dried over $MgSO_4$. After removal of solvent under vacuum, the crude product was purified by chromatography on silica gel using ethyl acetate/methanol (5:1) to obtain product (isomer mixture). The desired isomer was separated by silica gel column eluting with DCM/methanol. [(R)-2-(N,N-Diethylamino)ethylthio-Sar]-3-[N-methylvaline]-4-cyclosporin molecule formula: $C_{67}H_{122}N_{12}O_{12}S$, Exact Mass: 1318.90; MS (m/z): 1319.70 (M+1)$^+$; TLC $R_f$: 0.12 (ethyl acetate/methanol=10/1); HPLC RT: 12.39 min. (C8, 250 mm column, 210 nm, acetonitrile/water ($NH_4Ac$, 10 mmol/l), operation temperature: 64° C.).

Di(2-(N,N-diethylamino)ethyl)disulphide was prepared according to Bretschneider, et al., (1950) Montatsh. Chem., 81, 385-396 and H. Gilman, (1945) J. Am. Chem. Soc., 67, 1846, incorporated herein by reference.

N-MeVal-4-cyclosporin (SDZ-220-384) has been prepared according to the literature: See, e.g., Papageorgiou C. et al., 1994, *Bioorg & Med Chem Lett*, 4. 267-272 and Papageorgiou C. at al., 1994, *J. Med. Chem.*, 37, 3674-3676.

Example 2

[(R)-3-(N,N-Diethylamino)propylthio-Sar]-3-[N-methylvaline]-4-cyclosporin

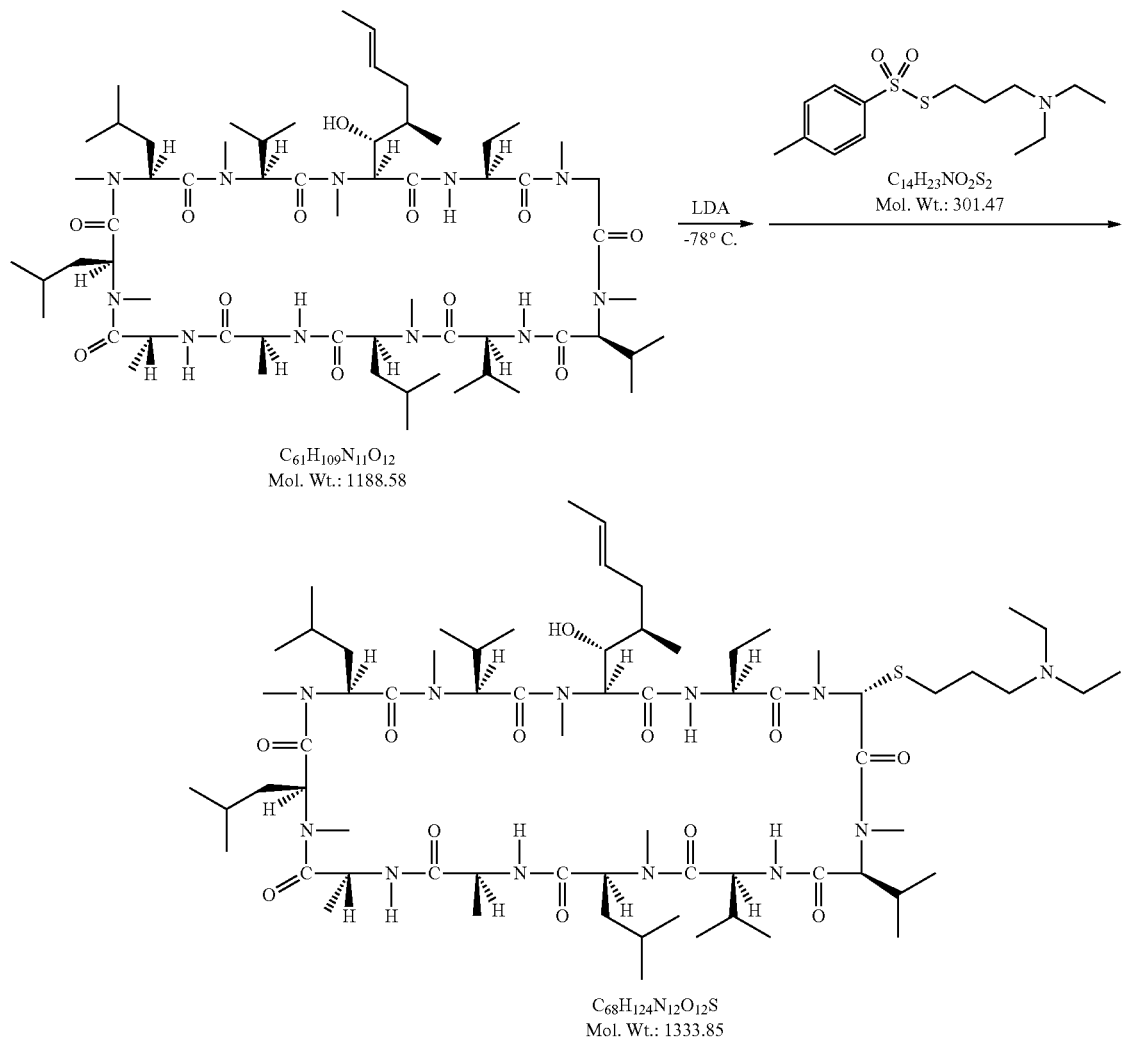

The LDA was prepared by adding diisopropylamine (0.712 ml, 5.05 mmol, 10 equiv), followed by n-butyllithium (2.87 M, 5.05 mmol, 1.76 ml, 10 equiv) to THF (20 ml) at −78° C. under nitrogen. The LDA solution was stirred for an hour and then a solution of N-MeVal-4-Cyclosporin (0.6 g, 0.505 mmol) in 5 ml of THF was dropwise added to LDA solution under stirring. The mixture was stirred at −78° C. for 2 hrs. The p-Toluene sulphonic acid (3-N,N-diethylamino)propylthioester (0.912 g, 3.0 mmol) dissolved in 5 ml of THF was added at −70° C. and the mixture was kept stirring at −78° C. for additional two hours. The cooling bath was removed and the mixture was allowed to warm up to room temperature for one hour. The reaction mixture was quenched with citric acid and then THF was removed under vacuum. The residue was extracted with ethyl acetate (3×25 ml), and the organic phase was dried over $MgSO_4$. Removal of solvent under vacuum yielded crude product, which was subject to chromatography on silica gel eluting with ethyl acetate/methanol (5:1) to obtain the product (isomer mixture). The desired isomer was separated by silica gel column eluting with DCM/methanol. [(R)-3-(N,N-Diethylamino)propylthio-Sar]-3-[N-methylvaline]-4-cyclosporin molecule formula: $C_{68}H_{124}N_{12}O_{12}S$, Exact Mass: 1332.92; MS (m/z): 1333.61 (M+1)$^+$, 1355.80 (M+Na)$^+$; TLC $R_f$: 0.05 (ethyl acetate/methanol=5/1); HPLC RT: 13.03 min (C8, 250 mm column, 210 nm, acetonitrile/water (0.05% TFA), operation temperature: 64° C.).

Preparation of p-toluene sulphonic acid (3-N,N-diethylamino)propylthioester

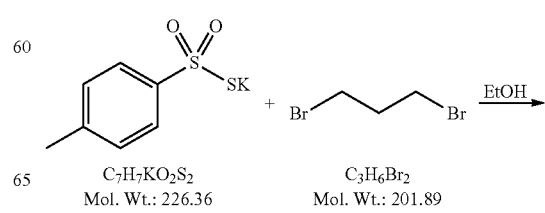

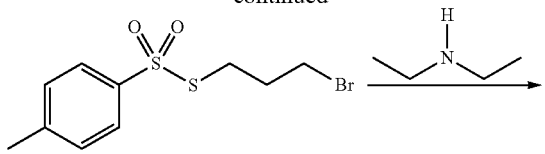

C₁₀H₁₃BrO₂S₂
Mol. Wt.: 309.24

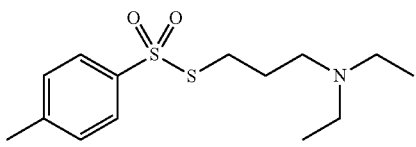

C₁₄H₂₃NO₂S₂
Mol. Wt.: 301.47 p-Toluenethiosulfonic acid potassium salt (10.00 g, 44.18 mmol) and 1,3-dibromopropane (44.67 g, 221.26 mmol) were added to ethanol (150 ml). The reaction mixture was stirred and heated to reflux for 3 hours. Removal of ethanol under vacuum yielded the residue, which was then mixed with 50 ml ethyl acetate. The ethyl acetate solution was washed with brine, dried over MgSO₄ and evaporated. The resulting residue was purified by column on silica gel using hexane/ethyl acetate (5:1) as solvents to give 12.40 g p-toluene sulphonic acid 3-bromopropylthioester. p-Toluene sulphonic acid 3-bromopropylthioester (12.00 g, 38.80 mmol) and diethylamine (8.55 g, 116.90 mmol) were mixed in 50 ml DCM. The reaction mixture was stirred and heated to reflux for one hour. Then the reaction mixture was washed with a NaHCO₃ solution (15 ml×2). The DCM solution was dried over MgSO₄ and evaporated. The residue was purified by column on silica gel with DCM/Methanol as solvent to give 4.40 g product.

Example 3

[(R)-3-(N-Morpholino)propylthio-Sar]-3-[N-methylvaline]-4-cyclosporin

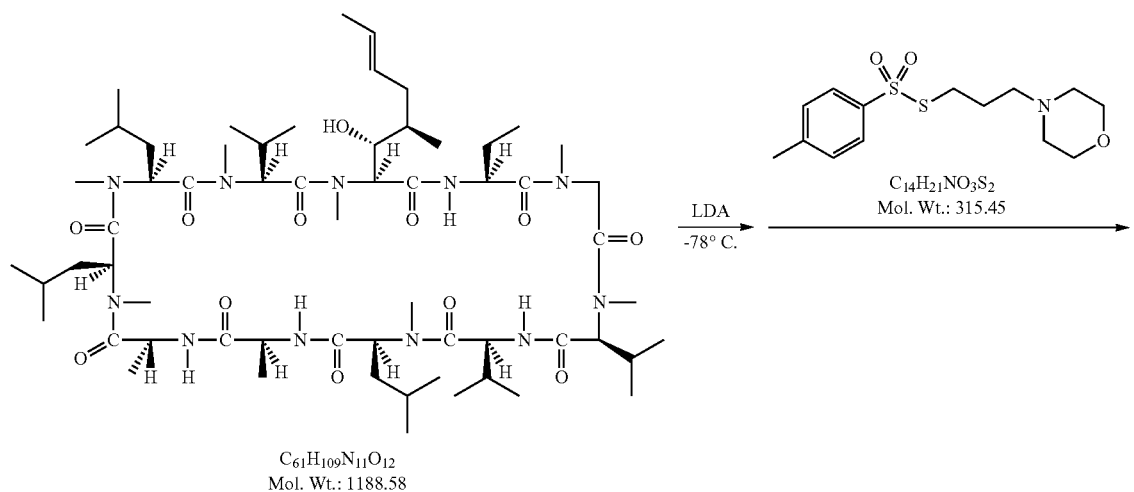

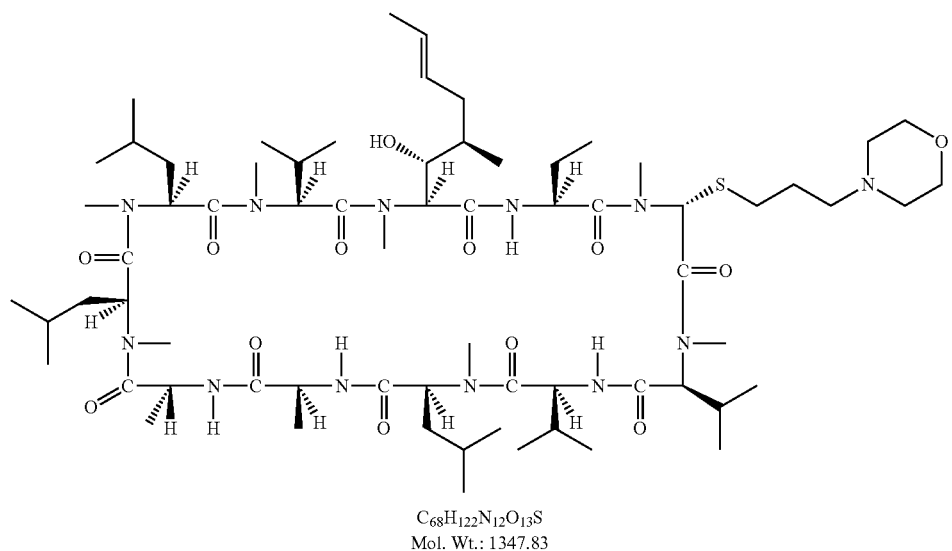

The LDA was prepared by adding diisopropylamine (0.712 ml, 5.05 mmol, 10 equiv), followed by n-butyllithium (2.87 M, 5.05 mmol, 1.76 ml, 10 equiv) to THF (20 ml) at −78° C. under nitrogen. The LDA solution was stirred for an hour and then a solution of N-MeVal-4-Cyclosporin (0.6 g, 0.505 mmol) in 5 ml of THF was quickly added to LDA solution. The mixture was stirred at −78° C. for 2 hrs. p-Toluene sulphonic acid 3-(4-morpholino)propylthioester (0.956 g, 3.0 mmol) dissolved in 5 mL of THF was added at −70° C. and the mixture was kept stirring at −78° C. for additional two hours. The cooling bath was removed and the mixture was warmed up to room temperature for one hour under stirring. The reaction was quenched with citric acid and then THF was removed under vacuum. The residue was extracted with ethyl acetate (3×25 ml). The organic phase was dried over $MgSO_4$. After removal of solvent under vacuum, the crude product was subject to chromatography on silica gel eluting with ethyl acetate/methanol (5:1) to obtain product (isomer mixture). The desired isomer was separated by silica gel column eluting with DCM/methanol. [(R)-3-(N-Morpholino)propylthio-Sar]-3-[N-methylvaline]-4-cyclosporin molecule formula: $C_{68}H_{122}N_{12}O_{13}S$, Exact Mass: 1346.90; MS (m/z): 1347.55 $(M+1)^+$, 1369.71 $(M+Na)^+$; TLC $R_f$: 0.5 (ethyl acetate/methanol=5/1); HPLC RT: 12.31 min (C8, 250 mm column, 210 nm, acetonitrile/water (0.05% TFA), operation temperature: 64° C.).

Preparation of p-Toluene sulphonic acid (3-Morphlino)propylthioester

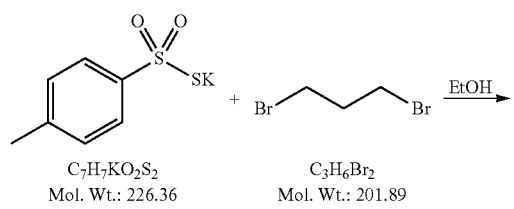

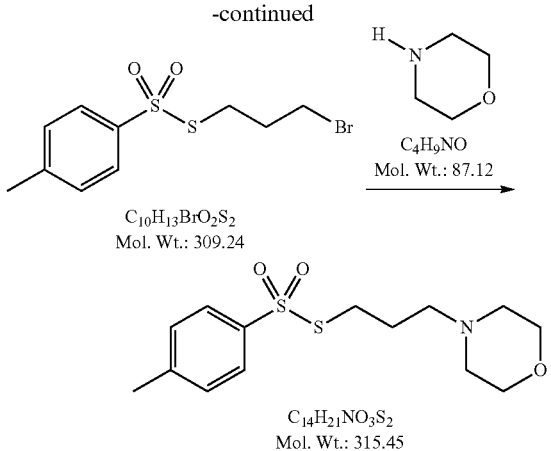

p-Toluenethiosulfonic acid potassium salt (10.00 g, 44.18 mmol) and 1,3-dibromopropane (44.67 g, 221.26 mmol) were added to ethanol (150 ml). The reaction mixture was stirred and heated to reflux for 3 hours. Removal of ethanol under vacuum yielded the residue, which was then mixed with 50 ml ethyl acetate. The ethyl acetate solution was washed with brine, dried over $MgSO_4$ and evaporated. The resulting residue was purified by column on silica gel using hexane/ethyl acetate (5:1) as solvents to give 12.40 g p-toluene sulphonic acid 3-bromopropylthioester. p-Toluenethiosulfonic acid potassium salt (9.67 g, 31.27 mmol) and morpholine (4.10 g, 47.10 mmol) and DIPEA (11.61 g, 89.72 mmol) were mixed in 125 ml DCM. The reaction mixture was stirred at room temperature for 48 hours. Then the reaction mixture was washed with a 1.3 N NaOH solution (15 ml×2). The DCM solution was dried over $MgSO_4$ and evaporated to give 8.90 g product.

Example 4

[(R)-2-(N,N-Diethylamino)ethylthio-Sar]-3-[N-methylisoleucine]-4-cyclosporin

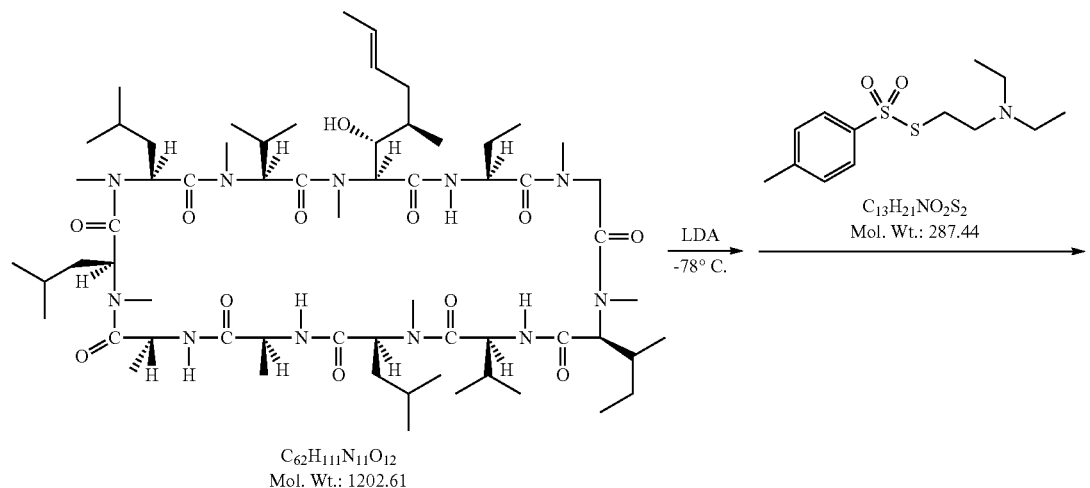

-continued

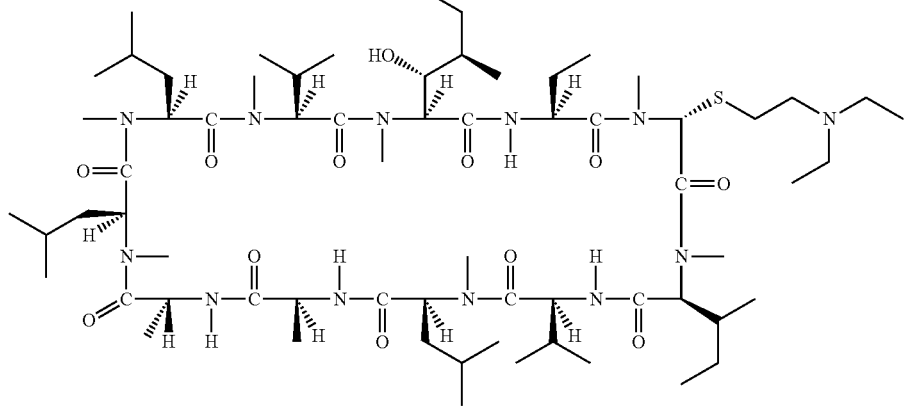

$C_{68}H_{124}N_{12}O_{12}S$
Mol. Wt.: 1333.85

To a solution of lithium diisobutylamide (LDA) (10.0 mmol) in dry tetrahydrofuran at −70° C. under an inert atmosphere was added, dropwise, a solution of N-MeIle-4-Cyclosporin (NIM-811, 1.2 g, 1.0 mmol) in dry THF, stirring was continued at −70° C. for 1 hour, and then the p-toluene sulphonic acid (2-N,N-diethylamino) ethyl thioestar (0.98 g, 3.4 mmol) dissolved in 5 ml of THF was added at −70° C. and the mixture was kept stirring at −70° C. for additional two hours. The reaction mixture was allowed to warm up to room temperature and was stirred for 2 hours. The reaction was quenched with citric acid and then THF was removed under vacuum. The residue was extracted with ethyl acetate (3×25 ml) and the organic phase was dried over $MgSO_4$. After removal of solvent under vacuum, the crude product was subject to chromatography on silica gel eluting with ethyl acetate/methanol (5:1) to obtain product and its isomer.

[(R)-2-(N,N-diethylamino)ethylthio-Sar]-3-[N-methylisoleucine]-4-cyclosporin molecule formula: $C_{68}H_{124}N_{12}O_{12}S$, Exact Mass: 1332.92; MS (m/z): 1333.9 $(M+1)^+$, 1355.9 $(M+Na)^+$; TLC $R_f$: 0.2 (ethyl acetate/methanol=10/1); HPLC RT: 12.56 min (C8, 250 mm column, 210 nm, acetonitrile/water ($NH_4Ac$, 10 mmol/l), operation temperature: 64° C.). Its isomer TLC $R_f$: 0.54 (ethyl acetate/methanol=10/1); HPLC RT: 12.94 min.

The preparation of p-toluene sulphonic acid (3-N,N-diethylamino)ethylthioester

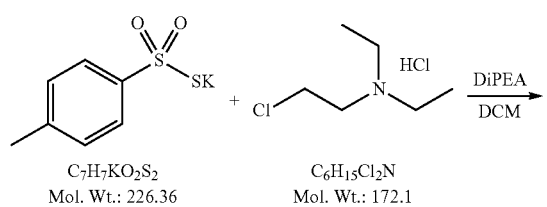

$C_7H_7KO_2S_2$
Mol. Wt.: 226.36

$C_6H_{15}Cl_2N$
Mol. Wt.: 172.1

-continued

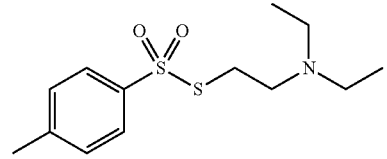

$C_{13}H_{21}NO_2S_2$
Mol. Wt.: 287.44

2-Chloro-N,N-diethylethanamine hydrochloride (15. 22 g, 88.44 mmol) was dissolved in 333 ml $H_2O$. p-Toluenethiosulfonic acid potassium salt (20.00 g, 88.50 mmol), KOH (4.96 g, 88.50 mmol) and DCM (220 ml) were added. The reaction mixture was stirred at room temperature for 48 hours and separated. The aqueous layer was extracted with DCM (100 ml×3). The combined DCM layers were washed with saturated $NaHCO_3$ solution, brine and dried over $MgSO_4$. The solvent was evaporated to give 22.80 g product.

N-MeIle-4-cyclosporin (NIM-811) was prepared according to the literature. See, e.g., Papageorgiou C. at al., 1994, *Bioorg & Med Chem Lett*, 4. 267-272 and Papageorgiou C. at al., 1994, *J. Med. Chem.*, 37, 3674-3676.

Example 5

[(R)-3-(N,N-Diethylamino)propylthio-Sar]-3-[N-methylisoleucine]-4-cyclosporin

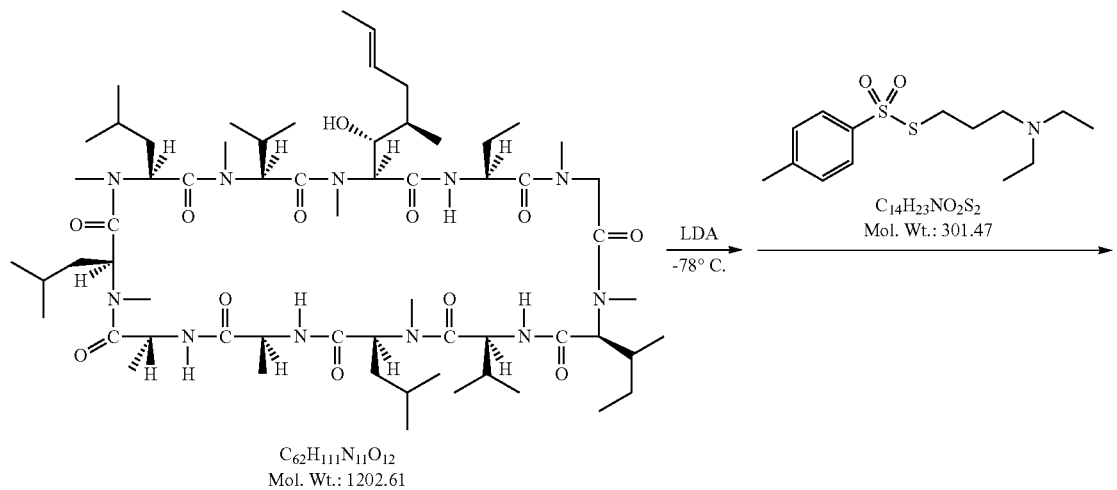

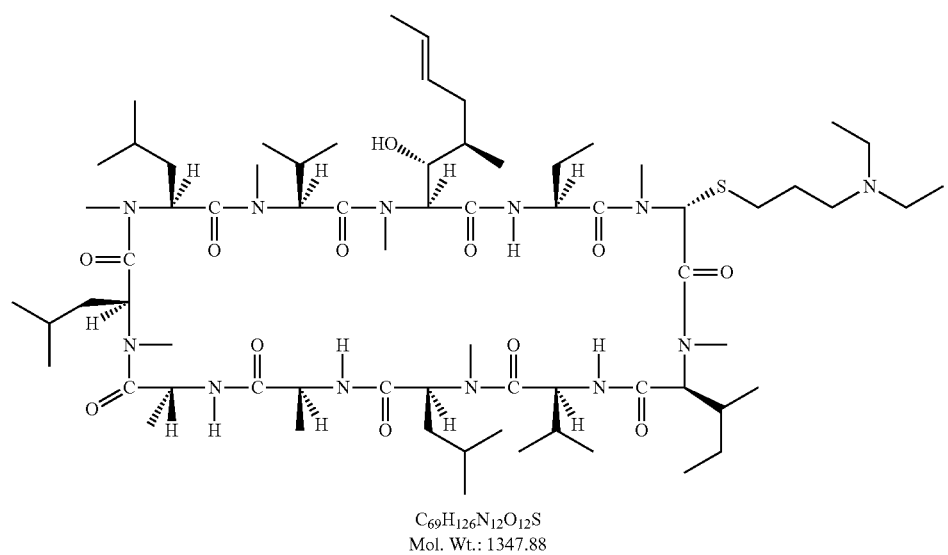

[(R)-3-(N,N-Diethylamino)propylthio-Sar]-3-[N-methylisoleucine]4-cyclosporin has been prepared according to the previous procedure.

[(R)-2-(N,N-diethylamino)propylthio-Sar]-3-[N-methylisoleucine]-4-cyclosporin molecule formula:

$C_{69}H_{126}N_{12}O_{12}S$, Exact Mass: 1346.93; MS (m/z): 1347.63 (M+1)$^+$, 1369.75 (M+Na)$^+$; TLC R$_f$: 0.40 (CH$_2$Cl$_2$/MeOH=9:1); HPLC RT: 13.66 min (C8, 250 mm column, 210 nm, acetonitrile/water (0.05% TFA in MeCN and H$_2$O), operation temperature: 64° C.).

Example 6

[(R)-3-(N-Morpholino)propylthio-Sar]-3-[N-methylisoleucine]-4-cyclosporin

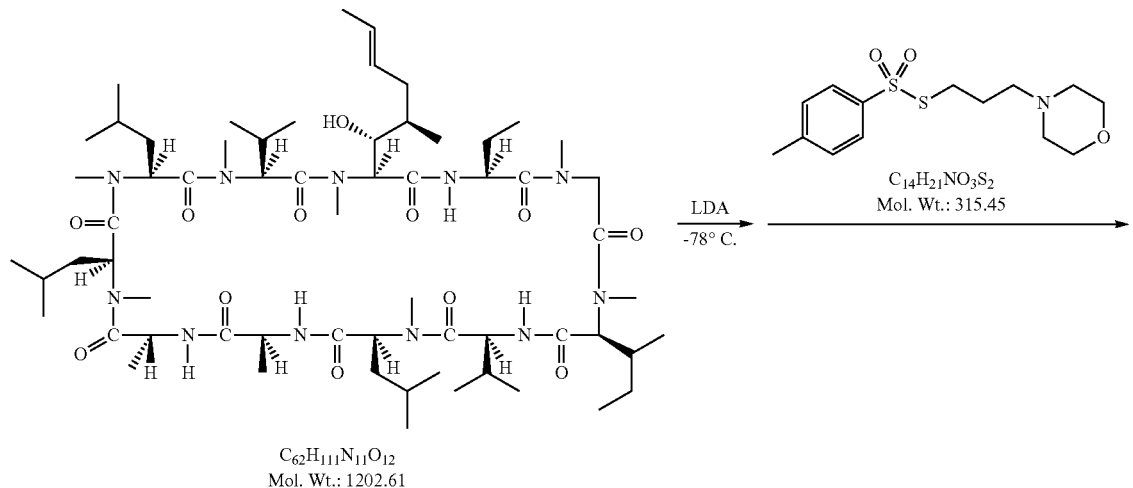

[(R)-3-(N-Morpholino)propylthio-Sar]-3-[N-methylisoleucine]-4-cyclosporin and its isomer have been prepared according to the previous procedure.

[(R)-2-(N-Morpholino)propylthio-Sar]-3-[N-methylisoleucine]-4-cyclosporin molecule formula: $C_{69}H_{124}N_{12}O_{13}S$, Exact Mass: 1360.91; MS (m/z): 1361.90 $(M+1)^+$, 1383.90 $(M+Na)^+$; TLC $R_f$: 0.21 (EtOAc/MeOH=10/1); HPLC RT: 18.59 min (C8, 250 mm column, 210 nm, acetonitrile/water ($NH_4OAc$ 10 mmol in MeCN and $H_2O$), operation temperature: 64° C.), and its isomer TLC $R_f$=0.36 (EtOAc/MeOH=10/1); HPLC rt=18.09 min (C8, 250 mm, $NH_4OAc$ 10 mmol in MeCN and $H_2O$, operation temperature: 64° C.).

Example 7

Stability Testing of Cyclosporin Derivatives

The stability of Cyclosporin derivatives were evaluated in methanol at 65° C. and 50° C., and HPLC was used to monitor possible degradation of these compounds (C8, 250 mm, $NH_4OAc$ 10 mmol in MeCN and $H_2O$, operation temperature: 65° C.).

It was found that [(R)-2-(N,N-Dimethylamino)ethylthio-Sar]-3-cyclosporin was not stable, and can easily degrade to form its corresponding epimer, which is expected to have low or no anti-HCV activity.

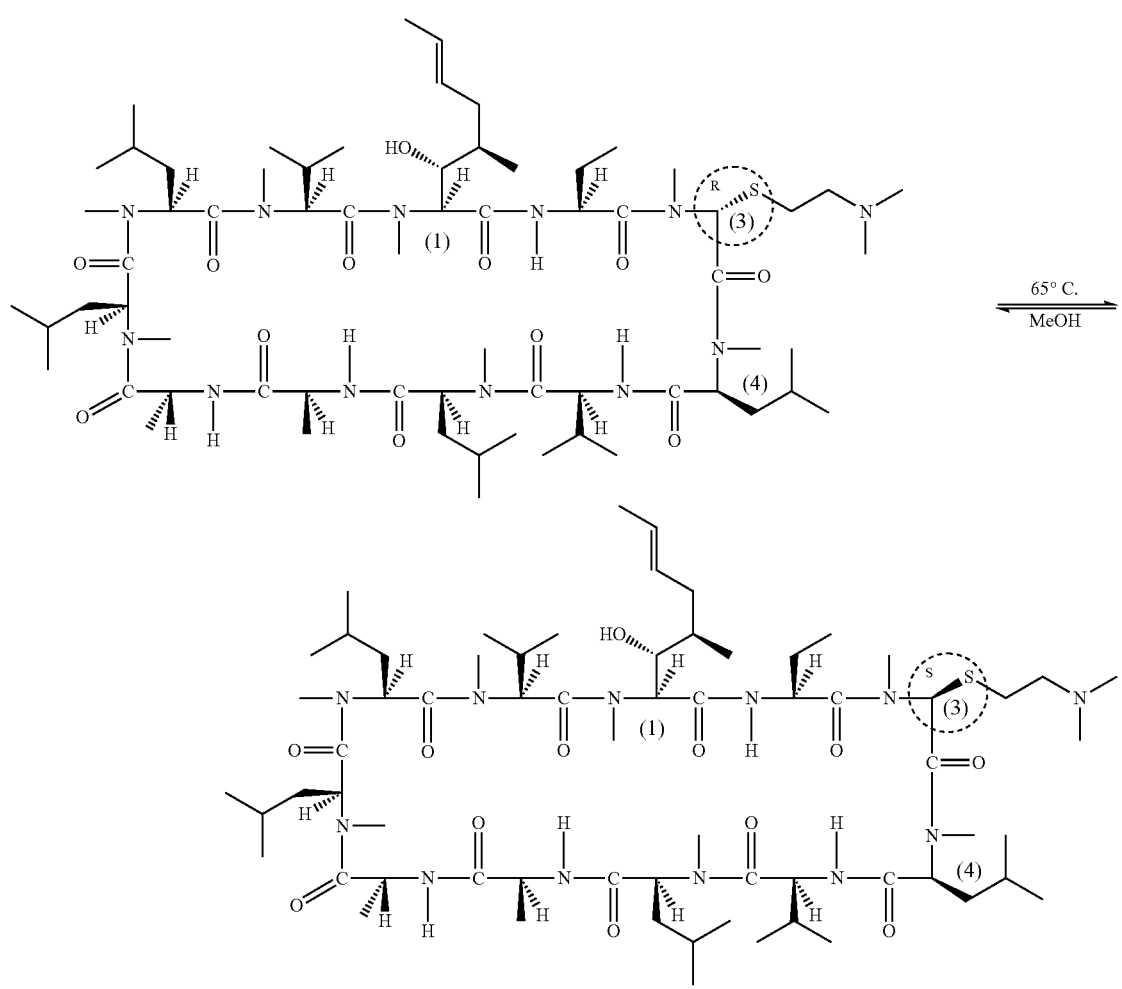
Epimerization of [(R)-2-(N,N-Dimethylamino)eth-ylthio-Sar]-3-cyclosporin in MeOH at 65° C.
| Compound | 2 hours | 4 hours | 6 hours |
|---|---|---|---|
| | 12% | 19% | 23% |

Epimerization of Cyclosporin Derivative in MeOH at 50° C.
| | 29 hrs | 77 hrs | 125 hrs |
|---|---|---|---|
| | 25.5% | 31.8% | 34.9% |
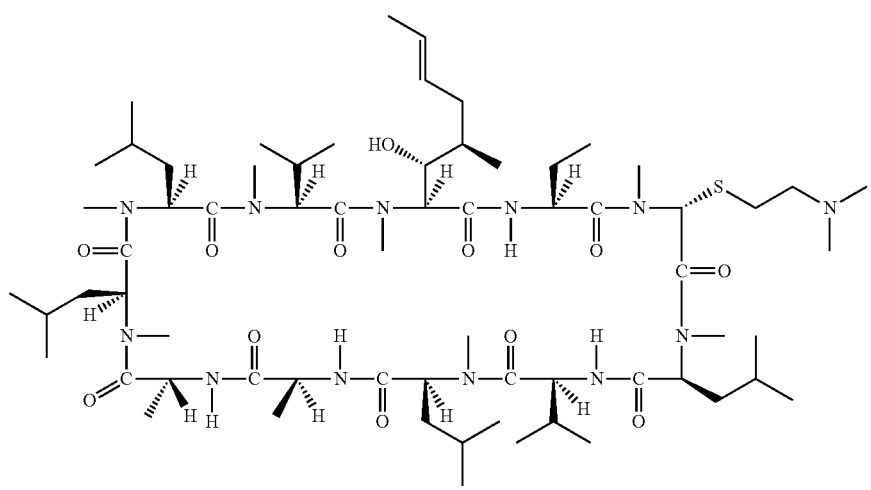 [SMILES: C/C=C/C[C@@H](C)[C@@H](O)[C@H]1C(=O)N[C@@H](CC)C(=O)N(C)[C@H](SCCN(C)C)C(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-2-(N,N-Dimethylamino)ethylthio-Sar]-3-cyclosporin
| | 4.4% | 10.4% | 16.2% |
|---|---|---|---|
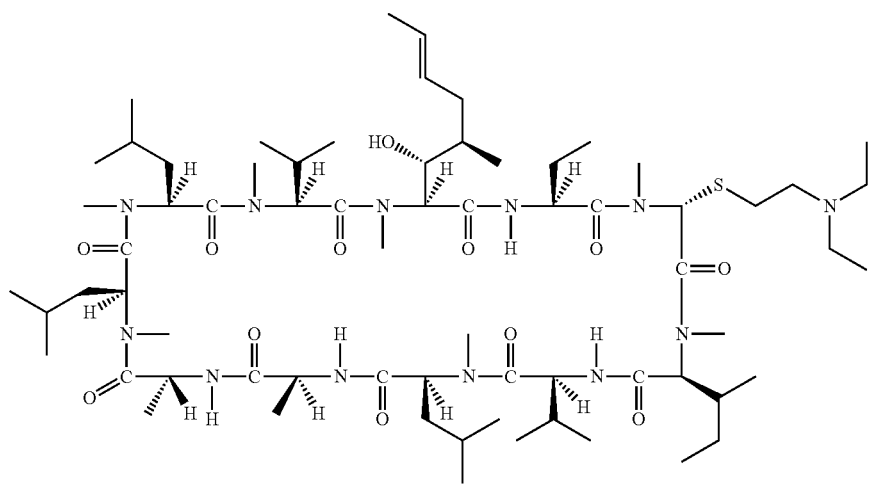
[(R)-2-(N,N-Diethylamino)ethylthio-Sar]-3-[N-MeIle]-4-cyclosporin -continued
|  | 29 hrs | 77 hrs | 125 hrs |
|---|---|---|---|
|  | 0% | 0% | 0% |
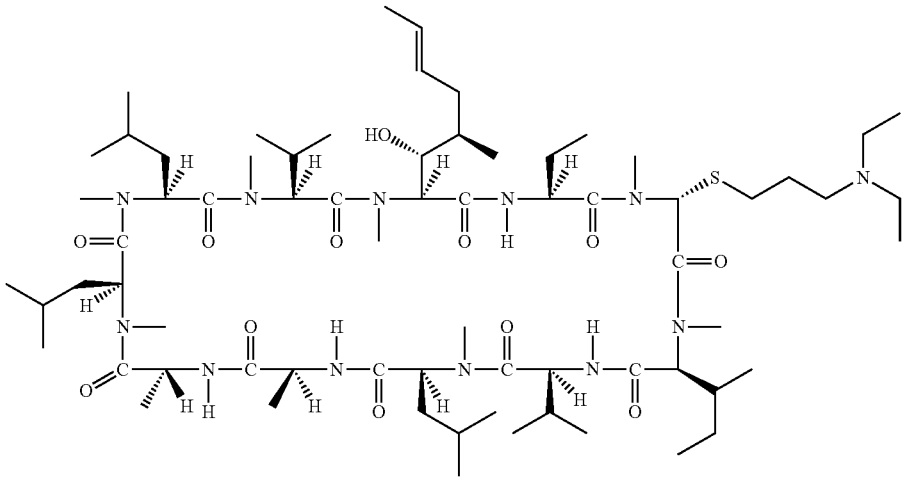
[(R)-3-(N,N-Diethylamino)propylthio-Sar]-3-[N-MeIle]-4-cyclosporin
|  | 0% | 0% | 0% |
|---|---|---|---|
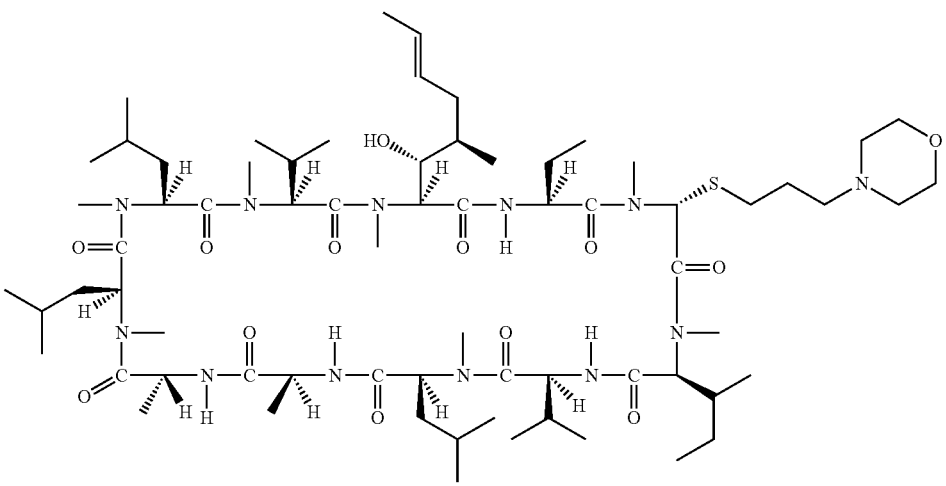
[(R)-3-(N-Morpholino)propyl-Sar]-3-[N-MeIle]-4-cyclosporin
|  | 0% | 0% | 0% |
|---|---|---|---|
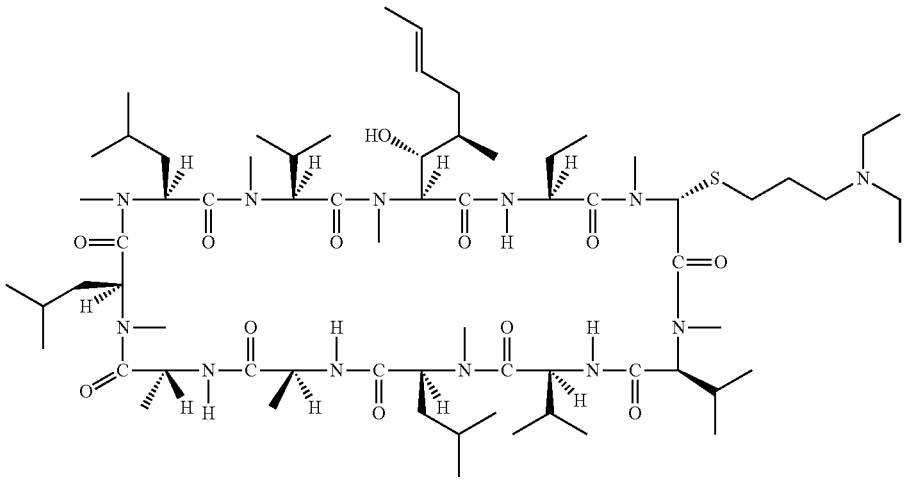
[(R)-3-(N,N-Diethylamino)propylthio-Sar]-3-[N-MeVal]-4-cyclosporin

|  | 29 hrs | 77 hrs | 125 hrs |
|---|---|---|---|
| 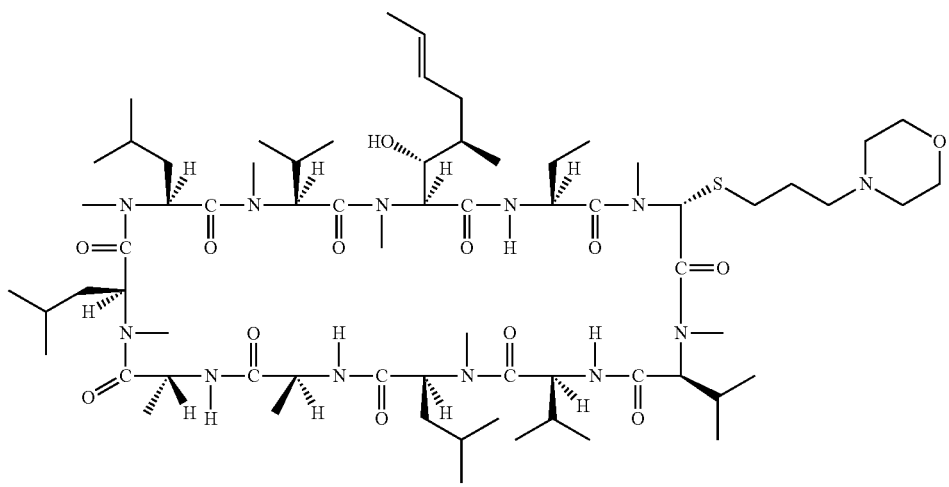<br>[(R)-3-(N-Morpholino)propyl-Sar]-3-[N-MeVal]-4-cyclosporin | 0% | 0% | 0% |
While not being bound by a particular theory, the inventors hypothesized that the epimerization occurred through the following pathway:

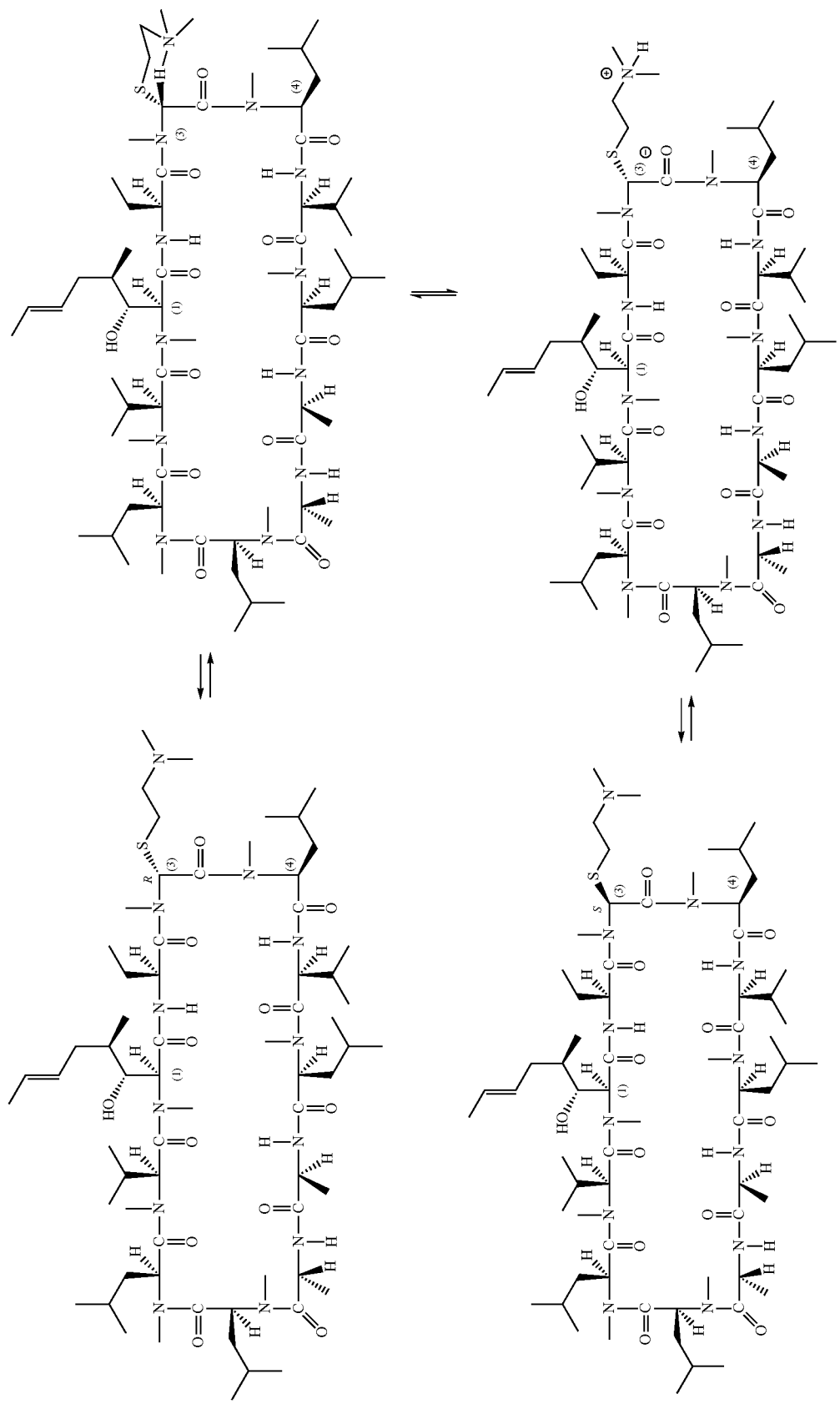

Thus, the two carbon side chain at position 3 of the sarcosine of cyclosporine contributes to the unstability, because it can form a six-membered ring transation state, and stimulate the epimerization. Accordingly, the inventors envisioned novel cyclosporine derivatives having enhanced stability while maintaining good cyclophilin binding activity. In particular, the inventors have surprisingly found that the longer side carbon chain (e.g., with 3 carbons or higher) and the bulky substitution on the amine terminal at position 3 can prevent or minimize the epimerization.

Reference Example 1

The synthesis of (N-MeVal)-4-Cyclosporin (SDZ-220-384)

Cyclosporin A-acetate

To a solution of 12 g (10 mmol) of Cyclosporin A (MW: 1202.61) in 40 ml of acetic anhydride (MW: 102.09, d 1.082), 40 ml of pyridine (MW: 79.01, d 0.978) and 0.4 g of 4-N,N-dimethylaminopyridine (MW: 122.17) was added. This solution was stirred for overnight at room temperature, and then the mixture was diluted with 600 ml of ethyl acetate. The mixture was washed with brine, saturated ammonium chloride water solution and with 15% of sodium bicarbonate. The organic phase was dried with sodium sulphate. filtered and evaporated under the reduced pressure. The toluene was added to the mixture until all of pyridine was evaporated to yield the pale yellow solid residue, which was purified by flash chromatography on a silica gel column (100-200 mesh) with eluent of ethyl acetate in haxene (1/3) to give the 11.8 g (9.48 mmol, 95%) of Cyclosporin A-acetate (MW: 1244.65).
MeLeuValMeLeuAlaDAlaMeLeuMeLeuMeValMeBmt(OAc)AbuSar-OMe To a suspension of 2.96 g (20 mmol, 2.5 equiv.) trimethyloxonium-fluoroborate (MW: 147.91) in 80 ml dichloromethane, 10 g (8 mmol) Cyclosporine A-acetate (MW: 1244.65) was added. The suspension was stirred for 18 hrs at room temperature, and then 9.9 mmol sodium methoxide in 40 ml methanol was added. The mixture was stirred for further 0.5 hr and then 40 ml of 2N sulfuric acid in 40 ml methanol was then added. The mixture was stirred for next 15-30 minutes at room temperature. The mixture is neutralized with 15% potassium bicarbonate solution. After that, it was extracted twice with 700 ml of ethyl acetate. The combined organic phase was washed with brine, dried with sodium sulphate, filtered and evaporated under reduced pressure. The crude product was purified by flash chromatography on a silica column (100-200 mesh) with eluent of methanol in methyl t-butyl ether to give the 7.15 g (5.6 mmol, 70%) of linear undecapeptide peptide (MW: 1276.69).
Phenylthiourea-MeLeuValMeLeuAlaD-AlaMeLeuMeLeuMeValMeBmt(OAc)AbuSar-OMe To a solution of 7.0 g (5.5 mmol) of linear undecapeptide peptide in 80 ml of tetrahydrofuran, 0.855 ml (7.15 mmol, 1.3 equiv.) of phenyl isothiocyanate (MW: 135.19, d 1.130) was added at room temperature. The solution was stirred for 3 hrs. The solvent was evaporated under reduced pressure. The residue was purified by flash chromatography on a silica gel column (100-200 mesh) with eluent of acetone in hexane (1/5) to give the 6.99 g (4.95 mmol, 90%) of linear phenylthiourea undecapeptide (MW: 1411.88, Exact Mass: 1410.89, found 1433.88 [M+Na]).
ValMeLeuAlaDAlaMeLeuMeLeuMeValMeBmt(OAc)AbuSar-OMe The Edman degradation was carried by similar method as Eur. J. Biochem., 1967; 1; 80, incorporated herein by reference. To 6.80 g (4.82 mmol) of linear phenylthiourea undecapeptide (MW: 1411.88) in 300 ml of toluene. 8 ml of trifluoroacetic acid (MW: 114.02, d 1.480) was added at room temperature and the mixture was stirred for 1.5-2 hrs. The reaction was quenched by using the slurry of sodium bicarbonate, the separated water phase was extracted twice with 100 ml of toluene and 100 ml of ethyl acetate. The combined organic phases were dried and the solvent was evaporated under reduced pressure. The residue was purified by flash chromatography on a silica column (100-200 mesh) with eluent of acetone in hexane (3/1) to give the 3.88 g (3.37 mmol, 70%) of linear decapeptide peptide (MW: 1149.51, Exact Mass: 1148.78, found 1149.78 [M+1].
BocMeValValMeLeuAlaDAlaMeLeuMeLeuMeValMeBmt(OAc)AbuSar-OMe To 3.8 g (3.3 mmol) of linear decapeptide peptide (MW: 1149.51) in 150 ml of dichloromethane, 0.92 g (3.96 mmol, 1.2 equiv.) of Boc-MeVal (MW: 231.29), 2.1 ml of 1-propanephosphonic acid cyclic anhydride (MW: 318.18, 50 wt. % solution in ethyl acetate) and 0.46 ml (3.3 mmol) of triethylamine (MW: 101.19, d 0.726) at 0° C. with stirring. The resulting solution was stirred at room temperature for 5 hrs. The solution was washed with brine and the organic phase separated. The water phase was extracted with 100 ml of ethyl acetate. The combined organic phase was dried over sodium sulphate and filtrated. Removal of the solvent under reduced pressure gave the residue, which was purified by flash chromatography on a silica column (100-200 mesh) with eluent of acetone in hexane (1/2.5) to give the 4.05 g (2.97 mmol, 90%) of linear Boc-N-MeVal-decapeptide peptide (MW: 1362.78, Exact Mass: 1361.91, found 1384.91 [M+Na].
BocMeValValMeLeuAlaDAlaMeLeuMeLeuMeValMeBmt(OAc)AbuSar-OH To 4.0 g (2.94 mmol) of linear Boc-N-MeVal-4-decapeptide peptide (MW: 1362.78) in 150 ml of ethyl alcohol cooled to 0° C. 7.1 ml (1.2 equiv.) of 0.5N sodium hydroxide was added with stirring. The solution was kept at 0° C. for 16 hrs, then neutralized with 0.5N hydrochloric acid to pH 3. The solvent was evaporated under the reduced pressure. The residue dissolved in 200 ml of ethyl acetate and washed with pH 3 buffer. The organic phase was dried over sodium sulphate and filtrated, removal of the solvent under the reduced pressure to gave the residue, which was purified by flash chromatography on a silica column (100-200 mesh) with eluent of methanol in ethyl acetate (1/8) to yield 2.55 g (1.89 mmol, 64.3%) of the free acid (MW: 1348.75).
MeValValMeLeuAlaDAlaMeLeuMeLeuMeValMeBmt(OAc)AbuSar-OH To 2.55 g (1.89 mmol) of free acid (MW: 1348.75) in 25 ml of dichloromethane was slowly added 5 ml of trifluoroacetic acid (MW: 114.02, d 1.480) at 0° C. The solution was allowed to stir at room for 2 hrs. After that, 300 ml of ethyl acetate was added and the solvent was removed under reduced pressure. Another 300 ml of ethyl acetate was added and the solvent was removed under reduced pressure again. The residue was purified by flash chromatography on a silica gel column (100-200 mesh) with eluent of methanol in acetone (1/3) to give the 2.01 g (1.61 mmol, 85%) of linear N-MeVal-4-decapeptide peptide free acid (MW: 1248.64, Exact Mass: 1247.90, found 1248.85 [M+1].

(N-MeVal)-4-Cyclosporin acetate

To 1032 mg (0.83 mmol) of linear N-MeVal-4-decapeptide peptide free acid (MW: 1248.64) in 250 ml of dichloromethane, 0.53 ml of 1-propanephosphonic acid cyclic anhydride (MW: 318.18, 50 wt. % solution in ethyl acetate), 0.109 ml (0.83 mmol) of 2,4,6-collidine (MW: 121.18, d 0.917) was added at 0° C. under stirring condition. The mixture was stirred at room temperature for 24 hrs. After that, the solution was passed into a thin layer of silica gel, and which was washed two times by 40 ml of ethyl acetate. The collected organic solution was evaporated under the reduced pressure. The residue was purified by flash chromatography on a silica gel column (230-400 mesh) with eluent of methanol in acetone (1/6) to give the 611 mg (0.50 mmol, 60%) of (N-Methyl-Val)-4-Cyclosporin acetate (MW: 1230.62, Exact Mass: 1229.84, found 1252.82 [M+Na].

(N-MeVal)-4-Cyclosporin

To 603 mg (0.49 mmol) of (N-Methyl-Val)-4-Cyclosporin acetate (MW: 1230.62) in 40 ml of methanol was added 1.9 ml (2.0 equiv.) of sodium methoxide (0.5 M in methanol), and the solution stirred at 0° C. for 0.5 hr and for 24 hrs at room temperature. The mixture was neutralized with 0.5N hydrochloric acid to pH 6. The solvent was evaporated under reduced pressure, the residue was dissolved in 200 ml of ethyl acetate, which was washed by aqueous sodium bicarbonate and brine, dried over sodium sulphate and filtered. Removal of the solvent gave the crude solid product, which was purified by flash chromatography on a silica gel column (230-400 mesh) with eluent of acetone in hexane (1/2) to give the 406 mg (0.34 mmol, 70%) of (N-Methyl-Val)-4-Cyclosporin (MW: 1188.58, Exact Mass: 1187.83, found 1210.81 [M+Na].

(N-MeVal)-4-Cyclosporin has been prepared according to the literatures: Papageorgiou C. at al., 1994, *Bioorg & Med Chem Lett*, 4. 267-272 and Papageorgiou C. at al., 1994, *J. Med. Chem.*, 37, 3674-3676.

Reference Example 2

The synthesis of (N-MeIle)-4-Cyclosporin (NIM-811)

The (N-MeIle)-4-Cyclosporin (NIM-811) has been synthesized according to the procedure described for the synthesis of (N-MeVal)-4-cyclosporin (SDZ 220-384).

Reference Example 3

[(R)-2-(N,N-Dimethylamino)ethylthio-Sar]-3-[N-methylvaline]-4-cyclosporin

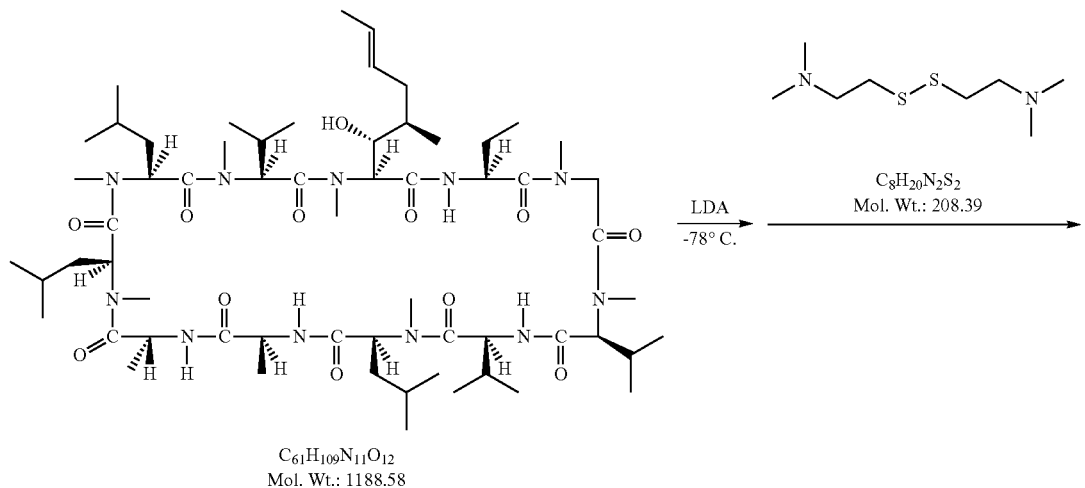

$C_{61}H_{109}N_{11}O_{12}$
Mol. Wt.: 1188.58

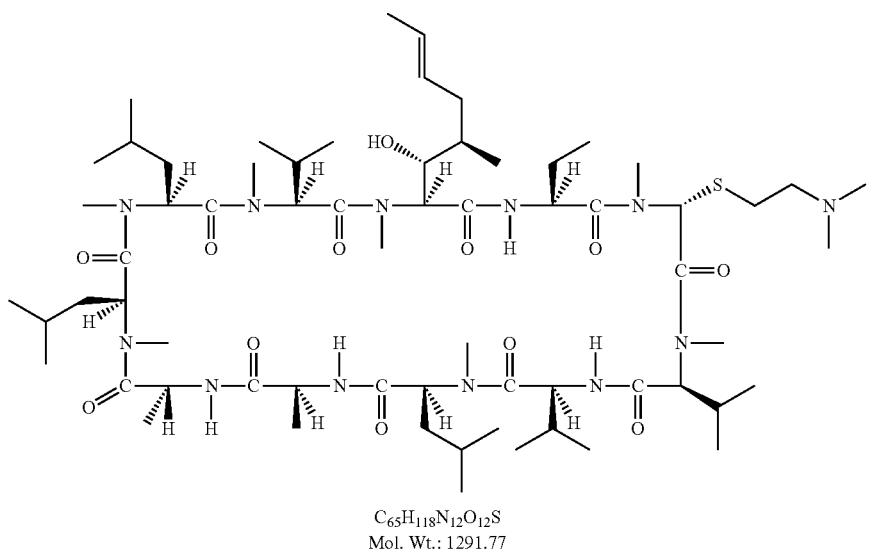

$C_{65}H_{118}N_{12}O_{12}S$
Mol. Wt.: 1291.77

The LDA was prepared by adding diisopropylamine (0.89 ml, 6.31 mmol, 15 equiv), followed by n-butyllithium (2.87 M, 6.31 mmol, 2.18 ml, 15 equiv.) to THF (20 ml) at −78° C. under nitrogen. The LDA solution was stirred for an hour and then a solution of N-MeVal-4-Cyclosporin in 5 ml of THF (0.5 g, 0.42 mmol) was dropwise added to the above LDA solution. The mixture was stirred at −78° C. for 2 hrs. Bis[2-(N,N-dimethylamino)ethyl]disulfide (1.75 g, 8.40 mmol) dissolved in 5 ml of THF was added at −70° C. and the mixture was kept stirring at −78° C. for additional two hours. The cooling bath was removed and the mixture was allowed to warm up to room temperature for one hour under stirring. The reaction was quenched with citric acid and then THF was removed under vacuum. The residue was extracted with methylene chloride (3×25 ml), and the organic phase was dried over MgSO$_4$. After removal of solvent under vacuum, the crude product was purified by chromatography on silica gel using ethyl acetate/methanol (5:1) to obtain the product (isomer mixture). The desired isomer was separated by silica gel column eluting with DCM/methanol.

[(R)-2-(N,N-Dimethylamino)ethylthio-Sar]-3-[N-methylvaline]-4-cyclosporin molecule formula: $C_{65}H_{15}N_{12}O_{12}S$, Exact Mass: 1290.87; MS (m/z): 1291.80 (M+1)$^+$; TLC R$_f$: 0.1 (ethyl acetate/methanol=10/1); HPLC RT: 11.87 min. (C8, 250 mm column, 210 nm, acetonitrile/water (NH$_4$Ac, 10 mmol/l), operation temperature: 64° C.).

N-MeVal-4-cyclosporin (SDZ-220-384) was prepared according to the literature. See, e.g., Papageorgiou C. at al., 1994, *Bioorg & Med Chem Lett*, 4. 267-272 and Papageorgiou C. at al., 1994, *J. Med. Chem.*, 37, 3674-3676.

TABLE I

| Ex. No. | W | R$_a$ | Name |
|---|---|---|---|
| | | 2 Carbon Chain | |
| 7 | S | 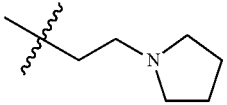 [SMILES: *CCN1CCCC1] | [(R)-2-(N-Pyrrolidinyl)ethylthio-Sar]-3-[N-methylisoleucine]-4-cyclosporin |
| 8 | S | 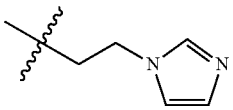 [SMILES: *CCn1ccnc1] | [(R)-2-(N-1H-Imidazolyl)ethylthio-Sar]-3-[N-methylisoleucine]-4-cyclosporin |
| 9 | S | 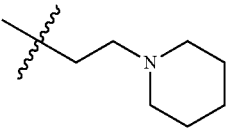 [SMILES: *CCN1CCCCC1] | [(R)-2-(N-Piperidinyl)ethylthio-Sar]-3-[N-methylisoleucine]-4-cyclosporin |
| 10 | S | 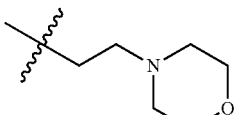 | [(R)-2-(N-Morpholino)ethylthio-Sar]-3-[N-methylisoleucine]-4-cyclosporin |
| 11 | S | 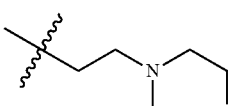 | [(R)-2-(N-Thiomorpholino)ethylthio-Sar]-3-[N-methylisoleucine]-4-cyclosporin |
| 12 | S | 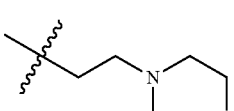 | [(R)-2-(Piperazinyl)ethylthio-Sar]-3-[N-methylisoleucine]-4-cyclosporin |
| 13 | S | 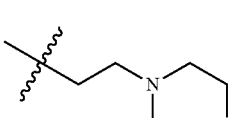 | [(R)-2-(N-4-Methylpiperazinyl)ethylthio-Sar]-3-[N-methylisoleucine]-4-cyclosporin |
| 14 | S | 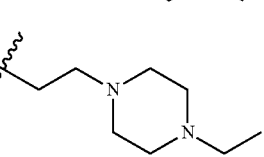 | [(R)-2-(N-4-Ethylpiperazinyl)ethylthio-Sar]-3-[N-methylisoleucine]-4-cyclosporin |

TABLE I-continued

| Ex. No. | W | R_a | Name |
|---|---|---|---|
| 15 | S | (piperazine with N-propyl) | [(R)-2-(N-4-n-Propylpiperazinyl)ethylthio-Sar]-3-[N-methylisoleucine]-4-cyclosporin |
| 16 | S | (piperazine with N-isopropyl) | [(R)-2-(N-4-iso-Propylpiperazinyl)ethylthio-Sar]-3-[N-methylisoleucine]-4-cyclosporin |
| 17 | O | (pyrrolidine) | [(R)-2-(N-Pyrrolidinyl)ethoxy-Sar]-3-[N-methylisoleucine]-4-cyclosporin |
| 18 | O | (imidazole) | [(R)-2-(N-1H-Imidazolyl)ethoxy-Sar]-3-[N-methylisoleucine]-4-cyclosporin |
| 19 | O | (piperidine) | [(R)-2-(N-Piperidinyl)ethoxy-Sar]-3-[N-methylisoleucine]-4-cyclosporin |
| 20 | O | (morpholine) | [(R)-2-(N-Morpholino)ethoxy-Sar]-3-[N-methylisoleucine]-4-cyclosporin |
| 21 | O | (thiomorpholine) | [(R)-2-(N-Thiomorpholino)ethoxy-Sar]-3-[N-methylisoleucine]-4-cyclosporin |
| 22 | O | (piperazine NH) | [(R)-2-(Piperazinyl)ethoxy-Sar]-3-[N-methylisoleucine]-4-cyclosporin |
| 23 | O | (N-methylpiperazine) | [(R)-2-(N-4-Methylpiperazinyl)ethoxy-Sar]-3-[N-methylisoleucine]-4-cyclosporin |
| 24 | O | (N-ethylpiperazine) | [(R)-2-(N-4-Ethylpiperazinyl)ethoxy-Sar]-3-[N-methylisoleucine]-4-cyclosporin |

TABLE I-continued

| Ex. No. | W | Name |
|---|---|---|
| 25 | O | [(R)-2-(N-4-n-Propylpiperazinyl)ethoxy-Sar]-3-[N-methylisoleucine]-4-cyclosporin |
| 26 | O | [(R)-2-(N-4-iso-Propylpiperazinyl)ethoxy-Sar]-3-[N-methylisoleucine]-4-cyclosporin |
| 27 | S | [(R)-2-(N,N-Di-n-proylamino)ethylthio-Sar]-3-[N-methylisoleucine]-4-cyclosporin |
| 28 | S | [(R)-2-(N-n-Propylamino)ethylthio-Sar]-3-[N-methylisoleucine]-4-cyclosporin |
| 29 | S | [(R)-2-(N-n-Propyl-N-methylamino)ethylthio-Sar]-3-[N-methylisoleucine]-4-cyclosporin |
| 30 | S | [(R)-2-(N-n-Propyl-N-ethylamino)ethylthio-Sar]-3-[N-methylisoleucine]-4-cyclosporin |
| 31 | S | [(R)-2-(N,N-Di-iso-propylamino)ethylthio-Sar]-3-[N-methylisoleucine]-4-cyclosporin |
| 32 | S | [(R)-2-(N-iso-Propylamino)ethylthio-Sar]-3-[N-methylisoleucine]-4-cyclosporin |
| 33 | S | [(R)-2-(N-iso-Propyl-N-methylamino)ethylthio-Sar]-3-[N-methylisoleucine]-4-cyclosporin |
| 34 | S | [(R)-2-(N-iso-Propyl-N-ethylamino)ethylthio-Sar]-3-[N-methylisoleucine]-4-cyclosporin |
| 35 | S | [(R)-2-(N-iso-Butylamino)ethylthio-Sar]-3-[N-methylisoleucine]-4-cyclosporin |

TABLE I-continued

| Ex. No. | W | $R_a$ | Name |
|---|---|---|---|
| 36 | S | (structure) | [(R)-2-(N-iso-Butyl-N-methylamino)ethylthio-Sar]-3-[N-methylisoleucine]-4-cyclosporin |
| 37 | S | (structure) | [(R)-2-(N-iso-Butyl-N-ethylamino)ethylthio-Sar]-3-[N-methylisoleucine]-4-cyclosporin |
| 38 | S | (structure) | [(R)-2-(N-(2',2'-dimethyl)propylamino)ethylthio-Sar]-3-[N-methylisoleucine]-4-cyclosporin |
| 39 | S | (structure) | [(R)-2-(N-(2',2'-dimethyl)propyl-N-methylamino)ethylthio-Sar]-3-[N-methylisoleucine]-4-cyclosporin |
| 40 | S | (structure) | [(R)-2-(N-(2',2'-dimethyl)propyl-N-ethylamino)ethylthio-Sar]-3-[N-methylisoleucine]-4-cyclosporin |
| 41 | O | (structure) | [(R)-2-(N,N-Diethylamino)ethoxy-Sar]-3-[N-methylisoleucine]-4-cyclosporin |
| 42 | O | (structure) | [(R)-2-(N,N-Di-n-proylamino)ethoxy-Sar]-3-[N-methylisoleucine]-4-cyclosporin |
| 43 | O | (structure) | [(R)-2-(N-n-Propylamino)ethoxy-Sar]-3-[N-methylisoleucine]-4-cyclosporin |
| 44 | O | (structure) | [(R)-2-(N-n-Propyl-N-methylamino)ethoxy-Sar]-3-[N-methylisoleucine]-4-cyclosporin |
| 45 | O | (structure) | [(R)-2-(N-n-Propyl-N-ethylamino)ethoxy-Sar]-3-[N-methylisoleucine]-4-cyclosporin |
| 46 | O | (structure) | [(R)-2-(N,N-Di-iso-propylamino)ethoxy-Sar]-3-[N-methylisoleucine]-4-cyclosporin |

TABLE I-continued

| Ex. No. | W | $R_a$ | Name |
|---|---|---|---|
| 47 | O | 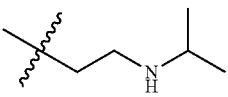 [SMILES: *CCNC(C)C] | [(R)-2-(N-iso-Propylamino)ethoxy-Sar]-3-[N-methylisoleucine]-4-cyclosporin |
| 48 | O | 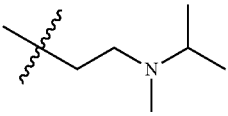 [SMILES: *CCN(C)C(C)C] | [(R)-2-(N-iso-Propyl-N-methylamino)ethoxy-Sar]-3-[N-methylisoleucine]-4-cyclosporin |
| 49 | O | 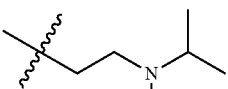 | [(R)-2-(N-iso-Propyl-N-ethylamino)ethoxy-Sar]-3-[N-methylisoleucine]-4-cyclosporin |
| 50 | O | 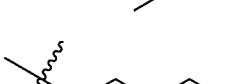 | [(R)-2-(N-iso-Butylamino)ethoxy-Sar]-3-[N-methylisoleucine]-4-cyclosporin |
| 51 | O |  | [(R)-2-(N-iso-Butyl-N-methylamino)ethoxy-Sar]-3-[N-methylisoleucine]-4-cyclosporin |
| 52 | O |  | [(R)-2-(N-iso-Butyl-N-ethylamino)ethoxy-Sar]-3-[N-methylisoleucine]-4-cyclosporin |
| 53 | O | 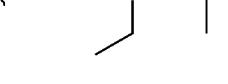 | [(R)-2-(N-(2',2'-dimethyl)propylamino)ethoxy-Sar]-3-[N-methylisoleucine]-4-cyclosporin |
| 54 | O | 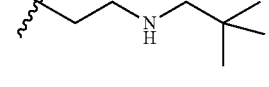 | [(R)-2-(N-(2',2'-dimethyl)propyl-N-methylamino)ethoxy-Sar]-3-[N-methylisoleucine]-4-cyclosporin |
| 55 | O | 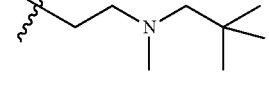 | [(R)-2-(N-(2',2'-dimethyl)propyl-N-ethylamino)ethoxy-Sar]-3-[N-methylisoleucine]-4-cyclosporin |
| 56 | S | 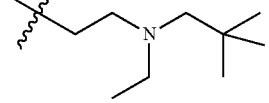 | [(R)-3-(N-Azetidinyl)propylthio-Sar]-3-[N-methylisoleucine]-4-cyclosporin |
| 57 | S | 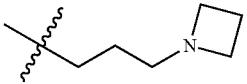 [SMILES: *CCCN1CCC1] | [(R)-3-(N-Pyrrolidinyl)propylthio-Sar]-3-[N-methylisoleucine]-4-cyclosporin |
| 58 | S | 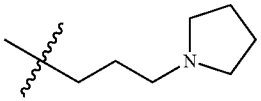 | [(R)-3-(N-1H-Imidazolyl)propylthio-Sar]-3-[N-methylisoleucine]-4-cyclosporin |

TABLE I-continued

| Ex. No. | W | Name |
|---|---|---|
| 59 | S | [(R)-3-(N-Piperidinyl)propylthio-Sar]-3-[N-methylisoleucine]-4-cyclosporin |
| 60 | S | [(R)-3-(N-Thiomorpholino)propylthio-Sar]-3-[N-methylisoleucine]-4-cyclosporin |
| 61 | S | [(R)-3-(Piperazinyl)propylthio-Sar]-3-[N-methylisoleucine]-4-cyclosporin |
| 62 | S | [(R)-3-(N-4-Methylpiperazinyl)propylthio-Sar]-3-[N-methylisoleucine]-4-cyclosporin |
| 63 | S | [(R)-3-(N-4-Ethylpiperazinyl)propylthio-Sar]-3-[N-methylisoleucine]-4-cyclosporin |
| 64 | S | [(R)-3-(N-4-n-Propylpiperazinyl)propylthio-Sar]-3-[N-methylisoleucine]-4-cyclosporin |
| 65 | S | [(R)-3-(N-4-iso-Propylpiperazinyl)propylthio-Sar]-3-[N-methylisoleucine]-4-cyclosporin |
| 66 | O | [(R)-3-(N-Azetidinyl)propoxy-Sar]-3-[N-methylisoleucine]-4-cyclosporin |
| 67 | O | [(R)-3-(N-Pyrrolidinyl)propoxy-Sar]-3-[N-methylisoleucine]-4-cyclosporin |
| 68 | O | [(R)-3-(N-1H-Imidazolyl)propoxy-Sar]-3-[N-methylisoleucine]-4-cyclosporin |
| 69 | O | [(R)-3-(N-Piperidinyl)propoxy-Sar]-3-[N-methylisoleucine]-4-cyclosporin |
| 70 | O | [(R)-3-(N-Morpholino)propoxy-Sar]-3-[N-methylisoleucine]-4-cyclosporin |

TABLE I-continued

| Ex. No. | W | $R_a$ | Name |
|---|---|---|---|
| 71 | O | 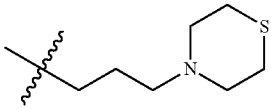 [SMILES: *CCCN1CCSCC1] | [(R)-3-(N-Thiomorpholino)propoxy-Sar]-3-[N-methylisoleucine]-4-cyclosporin |
| 72 | O | 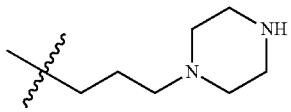 [SMILES: *CCCN1CCNCC1] | [(R)-3-(Piperazinyl)propoxy-Sar]-3-[N-methylisoleucine]-4-cyclosporin |
| 73 | O | 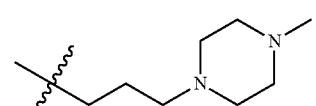 | [(R)-3-(N-4-Methylpiperazinyl)propoxy-Sar]-3-[N-methylisoleucine]-4-cyclosporin |
| 74 | O | 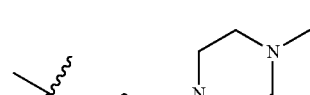 | [(R)-3-(N-4-Ethylpiperazinyl)propoxy-Sar]-3-[N-methylisoleucine]-4-cyclosporin |
| 75 | O | 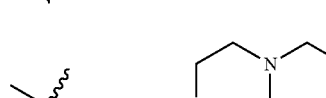 | [(R)-3-(N-4-n-Propylpiperazinyl)propoxy-Sar]-3-[N-methylisoleucine]-4-cyclosporin |
| 76 | O | 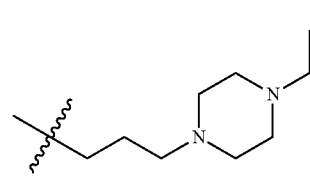 | [(R)-3-(N-4-iso-Propylpiperazinyl)propoxy-Sar]-3-[N-methylisoleucine]-4-cyclosporin |
| 77 | S | 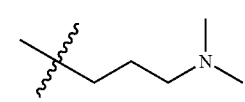 [SMILES: *CCCN(C)C] | [(R)-3-(N,N-Dimethylamino)propylthio-Sar]-3-[N-methylisoleucine]-4-cyclosporin |
| 78 | S | 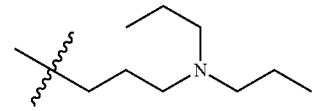 [SMILES: *CCCN(CCC)CCC] | [(R)-3-(N,N-Di-n-proylamino)propylthio-Sar]-3-[N-methylisoleucine]-4-cyclosporin |
| 79 | S | 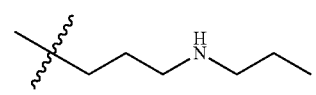 [SMILES: *CCCNCCC] | [(R)-3-(N-n-Propylamino)propylthio-Sar]-3-[N-methylisoleucine]-4-cyclosporin |
| 80 | S | 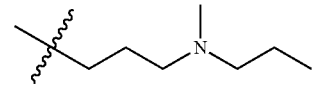 [SMILES: *CCCN(C)CCC] | [(R)-3-(N-n-Propyl-N-methylamino)propylthio-Sar]-3-[N-methylisoleucine]-4-cyclosporin |
| 81 | S | 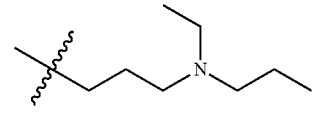 [SMILES: *CCCN(CC)CCC] | [(R)-3-(N-n-Propyl-N-ethylamino)propylthio-Sar]-3-[N-methylisoleucine]-4-cyclosporin |
| 82 | S | 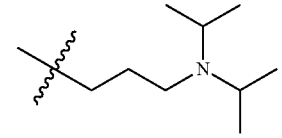 [SMILES: *CCCN(C(C)C)C(C)C] | [(R)-3-(N,N-Di-iso-propylamino)propylthio-Sar]-3-[N-methylisoleucine]-4-cyclosporin |

TABLE I-continued

| Ex. No. | W | Name |
|---|---|---|
| 83 | S | [(R)-3-(N-iso-Propylamino)propylthio-Sar]-3-[N-methylisoleucine]-4-cyclosporin |
| 84 | S | [(R)-3-(N-iso-Propyl-N-methylamino)propylthio-Sar]-3-[N-methylisoleucine]-4-cyclosporin |
| 85 | S | [(R)-3-(N-iso-Propyl-N-ethylamino)propylthio-Sar]-3-[N-methylisoleucine]-4-cyclosporin |
| 86 | S | [(R)-3-(N-iso-Butylamino)propylthio-Sar]-3-[N-methylisoleucine]-4-cyclosporin |
| 87 | S | [(R)-3-(N-iso-Butyl-N-methylamino)propylthio-Sar]-3-[N-methylisoleucine]-4-cyclosporin |
| 88 | S | [(R)-3-(N-iso-Butyl-N-ethylamino)propylthio-Sar]-3-[N-methylisoleucine]-4-cyclosporin |
| 89 | S | [(R)-3-(N-(2',2'-dimethyl)propylamino)propylthio-Sar]-3-[N-methylisoleucine]-4-cyclosporin |
| 90 | S | [(R)-3-(N-(2',2'-dimethyl)propyl-N-methylamino)propylthio-Sar]-3-[N-methylisoleucine]-4-cyclosporin |
| 91 | S | [(R)-3-(N-(2',2'-dimethyl)propyl-N-ethylamino)propylthio-Sar]-3-[N-methylisoleucine]-4-cyclosporin |
| 92 | O | [(R)-3-(N,N-Dimethylamino)propoxy-Sar]-3-[N-methylisoleucine]-4-cyclosporin |
| 93 | O | [(R)-3-(N,N-Diethylamino)propoxy-Sar]-3-[N-methylisoleucine]-4-cyclosporin |
| 94 | O | [(R)-3-(N,N-Di-n-proylamino)propoxy-Sar]-3-[N-methylisoleucine]-4-cyclosporin |
| 95 | O | [(R)-3-(N-n-Propylamino)propoxy-Sar]-3-[N-methylisoleucine]-4-cyclosporin |

TABLE I-continued

| Ex. No. | W | Rₐ | Name |
|---|---|---|---|
| 96 | O | | [(R)-3-(N-n-Propyl-N-methylamino)propoxy-Sar]-3-[N-methylisoleucine]-4-cyclosporin |
| 97 | O | | [(R)-3-(N-n-Propyl-N-ethylamino)propoxy-Sar]-3-[N-methylisoleucine]-4-cyclosporin |
| 98 | O | | [(R)-3-(N,N-Di-iso-propylamino)propoxy-Sar]-3-[N-methylisoleucine]-4-cyclosporin |
| 99 | O | | [(R)-3-(N-iso-Propylamino)propoxy-Sar]-3-[N-methylisoleucine]-4-cyclosporin |
| 100 | O | | [(R)-3-(N-iso-Propyl-N-methylamino)propoxy-Sar]-3-[N-methylisoleucine]-4-cyclosporin |
| 101 | O | | [(R)-3-(N-iso-Propyl-N-ethylamino)propoxy-Sar]-3-[N-methylisoleucine]-4-cyclosporin |
| 102 | O | | [(R)-3-(N-iso-Butylamino)propoxy-Sar]-3-[N-methylisoleucine]-4-cyclosporin |
| 103 | O | | [(R)-3-(N-iso-Butyl-N-methylamino)propoxy-Sar]-3-[N-methylisoleucine]-4-cyclosporin |
| 104 | O | | [(R)-3-(N-iso-Butyl-N-ethylamino)propoxy-Sar]-3-[N-methylisoleucine]-4-cyclosporin |
| 105 | O | | [(R)-3-(N-(2',2'-dimethyl)propylamino)propoxy-Sar]-3-[N-methylisoleucine]-4-cyclosporin |
| 106 | O | | [(R)-3-(N-(2',2'-dimethyl)propyl-N-methylamino)propoxy-Sar]-3-[N-methylisoleucine]-4-cyclosporin |
| 107 | O | | [(R)-3-(N-(2',2'-dimethyl)propyl-N-ethylamino)propoxy-Sar]-3-[N-methylisoleucine]-4-cyclosporin |
| 108 | S | | [(R)-4-(N-Azetidinyl)Butylthio-Sar]-3-[N-methylisoleucine]-4-cyclosporin |

TABLE I-continued

| Ex. No. | W | R$_a$ | Name |
|---|---|---|---|
| 109 | S | 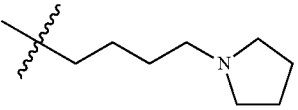 [SMILES: *CCCCN1CCCC1] | [(R)-4-(N-Pyrrolidinyl)Butylthio-Sar]-3-[N-methylisoleucine]-4-cyclosporin |
| 110 | S | 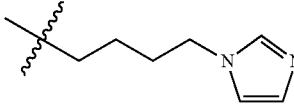 | [(R)-4-(N-1H-Imidazolyl)Butylthio-Sar]-3-[N-methylisoleucine]-4-cyclosporin |
| 111 | S | 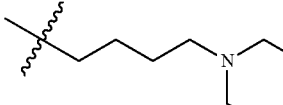 | [(R)-4-(N-Piperidinyl)Butylthio-Sar]-3-[N-methylisoleucine]-4-cyclosporin |
| 112 | S | 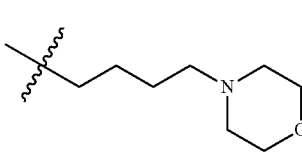 [SMILES: *CCCCN1CCCCC1] | [(R)-4-(N-Morpholino)Butylthio-Sar]-3-[N-methylisoleucine]-4-cyclosporin |
| 113 | S | 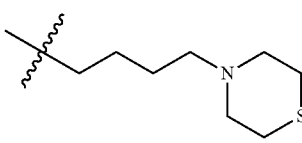 | [(R)-4-(N-Thiomorpholino)Butylthio-Sar]-3-[N-methylisoleucine]-4-cyclosporin |
| 114 | S | 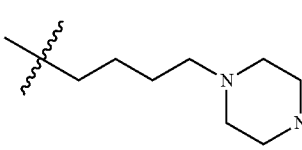 | [(R)-4-(Piperazinyl)Butylthio-Sar]-3-[N-methylisoleucine]-4-cyclosporin |
| 115 | S | 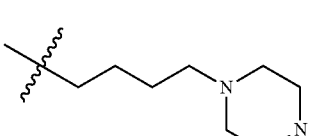 | [(R)-4-(N-4-Methylpiperazinyl)Butylthio-Sar]-3-[N-methylisoleucine]-4-cyclosporin |
| 116 | S | 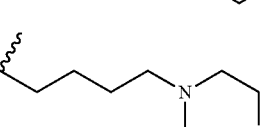 | [(R)-4-(N-4-Ethylpiperazinyl)Butylthio-Sar]-3-[N-methylisoleucine]-4-cyclosporin |
| 117 | S | 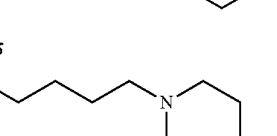 | [(R)-4-(N-4-n-Propylpiperazinyl)Butylthio-Sar]-3-[N-methylisoleucine]-4-cyclosporin |
| 118 | S | 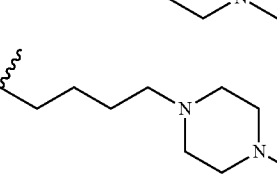 | [(R)-4-(N-4-iso-Propylpiperazinyl)Butylthio-Sar]-3-[N-methylisoleucine]-4-cyclosporin |
| 119 | O | 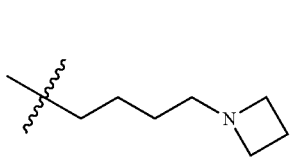 [SMILES: *CCCCN1CCC1] | [(R)-4-(N-Azetidinyl)Butoxy-Sar]-3-[N-methylisoleucine]-4-cyclosporin |

TABLE I-continued

| Ex. No. | W | R_a | Name |
|---|---|---|---|
| 120 | O | | [(R)-4-(N-Pyrrolidinyl)Butoxy-Sar]-3-[N-methylisoleucine]-4-cyclosporin |
| 121 | O | | [(R)-4-(N-1H-Imidazolyl)Butoxy-Sar]-3-[N-methylisoleucine]-4-cyclosporin |
| 122 | O | | [(R)-4-(N-Piperidinyl)Butoxy-Sar]-3-[N-methylisoleucine]-4-cyclosporin |
| 123 | O | | [(R)-4-(N-Morpholino)Butoxy-Sar]-3-[N-methylisoleucine]-4-cyclosporin |
| 124 | O | | [(R)-4-(N-Thiomorpholino)Butoxy-Sar]-3-[N-methylisoleucine]-4-cyclosporin |
| 125 | O | | [(R)-4-(Piperazinyl)Butoxy-Sar]-3-[N-methylisoleucine]-4-cyclosporin |
| 126 | O | | [(R)-4-(N-4-Methylpiperazinyl)Butoxy-Sar]-3-[N-methylisoleucine]-4-cyclosporin |
| 127 | O | | [(R)-4-(N-4-Ethylpiperazinyl)Butoxy-Sar]-3-[N-methylisoleucine]-4-cyclosporin |
| 128 | O | | [(R)-4-(N-4-n-Propylpiperazinyl)Butoxy-Sar]-3-[N-methylisoleucine]-4-cyclosporin |
| 129 | O | | [(R)-4-(N-4-iso-Propylpiperazinyl)Butoxy-Sar]-3-[N-methylisoleucine]-4-cyclosporin |

TABLE I-continued

| Ex. No. | W | $R_a$ | Name |
|---|---|---|---|
| 130 | S | 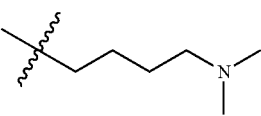 [SMILES: *CCCCN(C)C] | [(R)-4-(N,N-Dimethylamino)butylthio-Sar]-3-[N-methylisoleucine]-4-cyclosporin |
| 131 | S | 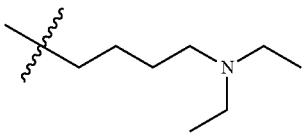 [SMILES: *CCCCN(CC)CC] | [(R)-4-(N,N-Diethylamino)butylthio-Sar]-3-[N-methylisoleucine]-4-cyclosporin |
| 132 | S | 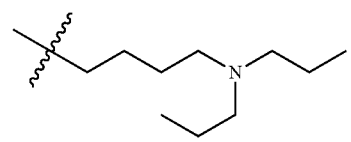 [SMILES: *CCCCN(CCC)CCC] | [(R)-4-(N,N-Di-n-proylamino)butylthio-Sar]-3-[N-methylisoleucine]-4-cyclosporin |
| 133 | S | 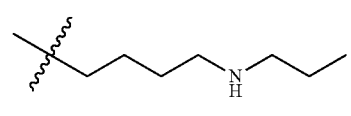 [SMILES: *CCCCNCCC] | [(R)-4-(N-n-Propylamino)butylthio-Sar]-3-[N-methylisoleucine]-4-cyclosporin |
| 134 | S | 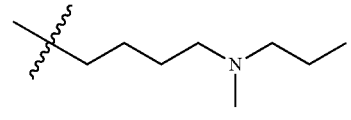 [SMILES: *CCCCN(C)CCC] | [(R)-4-(N-n-Propyl-N-methylamino)butylthio-Sar]-3-[N-methylisoleucine]-4-cyclosporin |
| 135 | S | 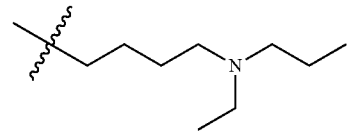 [SMILES: *CCCCN(CC)CCC] | [(R)-4-(N-n-Propyl-N-ethylamino)butylthio-Sar]-3-[N-methylisoleucine]-4-cyclosporin |
| 136 | S | 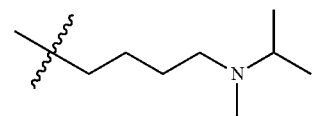 | [(R)-4-(N,N-Di-iso-propylamino)butylthio-Sar]-3-[N-methylisoleucine]-4-cyclosporin |
| 137 | S | 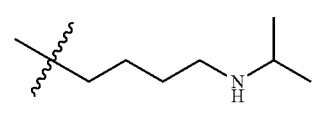 [SMILES: *CCCCNC(C)C] | [(R)-4-(N-iso-Propylamino)butylthio-Sar]-3-[N-methylisoleucine]-4-cyclosporin |
| 138 | S | 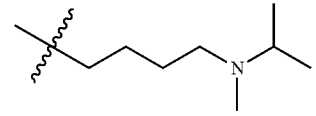 [SMILES: *CCCCN(C)C(C)C] | [(R)-4-(N-iso-Propyl-N-methylamino)butylthio-Sar]-3-[N-methylisoleucine]-4-cyclosporin |
| 139 | S | 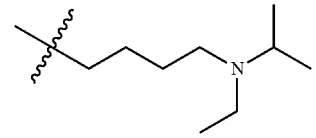 | [(R)-4-(N-iso-Propyl-N-ethylamino)butylthio-Sar]-3-[N-methylisoleucine]-4-cyclosporin |
| 140 | S | 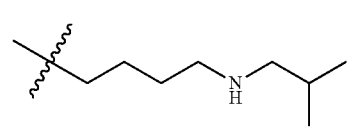 [SMILES: *CCCCNCC(C)C] | [(R)-4-(N-iso-Butylamino)butylthio-Sar]-3-[N-methylisoleucine]-4-cyclosporin |
| 141 | S | 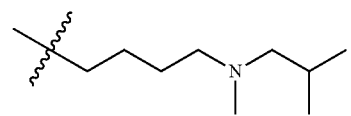 [SMILES: *CCCCN(C)CC(C)C] | [(R)-4-(N-iso-Butyl-N-methylamino)butylthio-Sar]-3-[N-methylisoleucine]-4-cyclosporin |

TABLE I-continued

| Ex. No. | W | Name |
|---|---|---|
| 142 | S | [(R)-4-(N-iso-Butyl-N-ethylamino)butylthio-Sar]-3-[N-methylisoleucine]-4-cyclosporin |
| 143 | S | [(R)-4-(N-(2',2'-dimethyl)propylamino)butylthio-Sar]-3-[N-methylisoleucine]-4-cyclosporin |
| 144 | S | [(R)-4-(N-(2',2'-dimethyl)propyl-N-methylamino)butylthio-Sar]-3-[N-methylisoleucine]-4-cyclosporin |
| 145 | S | [(R)-4-(N-(2',2'-dimethyl)propyl-N-ethylamino)butylthio-Sar]-3-[N-methylisoleucine]-4-cyclosporin |
| 146 | O | [(R)-4-(N,N-Dimethylamino)butoxy-Sar]-3-[N-methylisoleucine]-4-cyclosporin |
| 147 | O | [(R)-4-(N,N-Diethylamino)butoxy-Sar]-3-[N-methylisoleucine]-4-cyclosporin |
| 148 | O | [(R)-4-(N,N-Di-n-proylamino)butoxy-Sar]-3-[N-methylisoleucine]-4-cyclosporin |
| 149 | O | [(R)-4-(N-n-Propylamino)butoxy-Sar]-3-[N-methylisoleucine]-4-cyclosporin |
| 150 | O | [(R)-4-(N-n-Propyl-N-methylamino)butoxy-Sar]-3-[N-methylisoleucine]-4-cyclosporin |
| 151 | O | [(R)-4-(N-n-Propyl-N-ethylamino)butoxy-Sar]-3-[N-methylisoleucine]-4-cyclosporin |
| 152 | O | [(R)-4-(N,N-Di-iso-propylamino)butoxy-Sar]-3-[N-methylisoleucine]-4-cyclosporin |

TABLE I-continued

| Ex. No. | W | $R_a$ | Name |
|---|---|---|---|
| 153 | O | 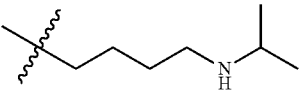 [SMILES: *CCCCNC(C)C] | [(R)-4-(N-iso-Propylamino)butoxy-Sar]-3-[N-methylisoleucine]-4-cyclosporin |
| 154 | O | 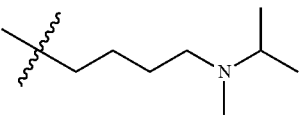 [SMILES: *CCCCN(C)C(C)C] | [(R)-4-(N-iso-Propyl-N-methylamino)butoxy-Sar]-3-[N-methylisoleucine]-4-cyclosporin |
| 155 | O | 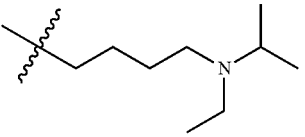 [SMILES: *CCCCN(CC)C(C)C] | [(R)-4-(N-iso-Propyl-N-ethylamino)butoxy-Sar]-3-[N-methylisoleucine]-4-cyclosporin |
| 156 | O | 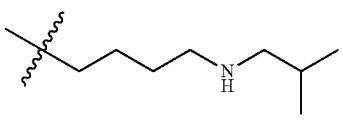 | [(R)-4-(N-iso-Butylamino)butoxy-Sar]-3-[N-methylisoleucine]-4-cyclosporin |
| 157 | O | 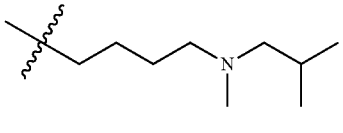 [SMILES: *CCCCN(C)CC(C)C] | [(R)-4-(N-iso-Butyl-N-methylamino)butoxy-Sar]-3-[N-methylisoleucine]-4-cyclosporin |
| 158 | O | 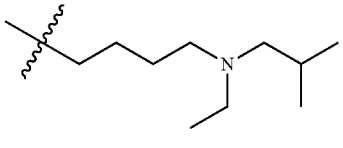 [SMILES: *CCCCN(CC)CC(C)C] | [(R)-4-(N-iso-Butyl-N-ethylamino)butoxy-Sar]-3-[N-methylisoleucine]-4-cyclosporin |
| 159 | O | 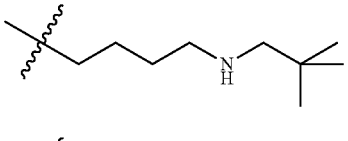 | [(R)-4-(N-(2',2'-dimethyl)propylamino)butoxy-Sar]-3-[N-methylisoleucine]-4-cyclosporin |
| 160 | O | 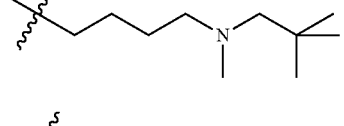 | [(R)-4-(N-(2',2'-dimethyl)propyl-N-methylamino)butoxy-Sar]-3-[N-methylisoleucine]-4-cyclosporin |
| 161 | O | 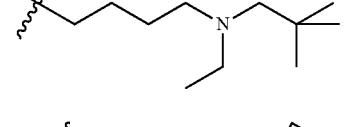 | [(R)-4-(N-(2',2'-dimethyl)propyl-N-ethylamino)butoxy-Sar]-3-[N-methylisoleucine]-4-cyclosporin |
| 162 | S | 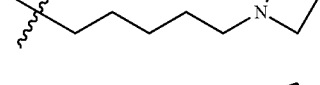 | [(R)-5-(N-Azetidinyl)pentylthio-Sar]-3-[N-methylisoleucine]-4-cyclosporin |
| 163 | S | 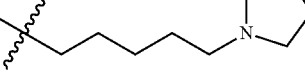 | [(R)-5-(N-Pyrrolidinyl)pentylthio-Sar]-3-[N-methylisoleucine]-4-cyclosporin |
| 164 | S | 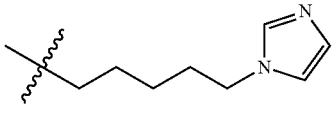 [SMILES: *CCCCCn1ccnc1] | [(R)-5-(N-1H-Imidazolyl)pentylthio-Sar]-3-[N-methylisoleucine]-4-cyclosporin |

TABLE I-continued

| Ex. No. | W | R_a | Name |
|---|---|---|---|
| 165 | S | (pentyl-piperidinyl) | [(R)-5-(N-Piperidinyl)pentylthio-Sar]-3-[N-methylisoleucine]-4-cyclosporin |
| 166 | S | (pentyl-morpholino) | [(R)-5-(N-Morpholino)pentylthio-Sar]-3-[N-methylisoleucine]-4-cyclosporin |
| 167 | S | (pentyl-thiomorpholino) | [(R)-5-(N-Thiomorpholino)pentylthio-Sar]-3-[N-methylisoleucine]-4-cyclosporin |
| 168 | S | (pentyl-piperazinyl) | [(R)-5-(Piperazinyl)pentylthio-Sar]-3-[N-methylisoleucine]-4-cyclosporin |
| 169 | S | (pentyl-N-methylpiperazinyl) | [(R)-5-(N-4-Methylpiperazinyl)pentylthio-Sar]-3-[N-methylisoleucine]-4-cyclosporin |
| 170 | S | (pentyl-N-ethylpiperazinyl) | [(R)-5-(N-4-Ethylpiperazinyl)pentylthio-Sar]-3-[N-methylisoleucine]-4-cyclosporin |
| 171 | S | (pentyl-N-propylpiperazinyl) | [(R)-5-(N-4-n-Propylpiperazinyl)pentylthio-Sar]-3-[N-methylisoleucine]-4-cyclosporin |
| 172 | S | (pentyl-N-isopropylpiperazinyl) | [(R)-5-(N-4-iso-Propylpiperazinyl)pentylthio-Sar]-3-[N-methylisoleucine]-4-cyclosporin |
| 173 | O | (pentyl-azetidinyl) | [(R)-5-(N-Azetidinyl)pentyloxy-Sar]-3-[N-methylisoleucine]-4-cyclosporin |
| 174 | O | (pentyl-pyrrolidinyl) | [(R)-5-(N-Pyrrolidinyl)pentyloxy-Sar]-3-[N-methylisoleucine]-4-cyclosporin |
| 175 | O | (pentyl-imidazolyl) | [(R)-5-(N-1H-Imidazolyl)pentyloxy-Sar]-3-[N-methylisoleucine]-4-cyclosporin |
| 176 | O | (pentyl-piperidinyl) | [(R)-5-(N-Piperidinyl)pentyloxy-Sar]-3-[N-methylisoleucine]-4-cyclosporin |

TABLE I-continued

| Ex. No. | W | R_a | Name |
|---|---|---|---|
| 177 | O | 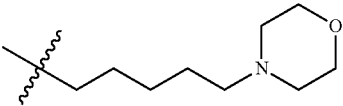 [SMILES: *CCCCCN1CCOCC1] | [(R)-5-(N-Morpholino)pentyloxy-Sar]-3-[N-methylisoleucine]-4-cyclosporin |
| 178 | O | 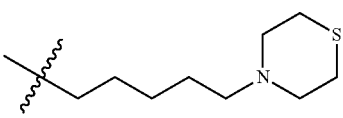 [SMILES: *CCCCCN1CCSCC1] | [(R)-5-(N-Thiomorpholino)pentyloxy-Sar]-3-[N-methylisoleucine]-4-cyclosporin |
| 179 | | 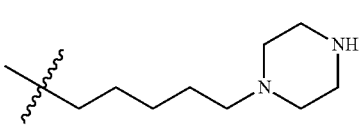 [SMILES: *CCCCCN1CCNCC1] | [(R)-5-(Piperazinyl)pentyloxy-Sar]-3-[N-methylisoleucine]-4-cyclosporin |
| 180 | O | 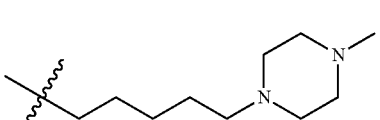 | [(R)-5-(N-4-Methylpiperazinyl)pentyloxy-Sar]-3-[N-methylisoleucine]-4-cyclosporin |
| 181 | O |  | [(R)-5-(N-4-Ethylpiperazinyl)pentyloxy-Sar]-3-[N-methylisoleucine]-4-cyclosporin |
| 182 | O | 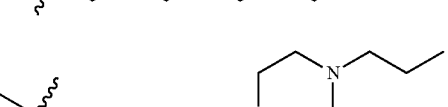 | [(R)-5-(N-4-n-Propylpiperazinyl)pentyloxy-Sar]-3-[N-methylisoleucine]-4-cyclosporin |
| 183 | O | 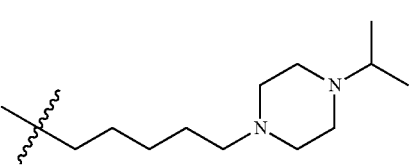 [SMILES: *CCCCCN1CCN(C(C)C)CC1] | [(R)-5-(N-4-iso-Propylpiperazinyl)pentyloxy-Sar]-3-[N-methylisoleucine]-4-cyclosporin |
| 184 | S | 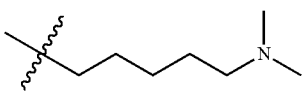 | [(R)-5-(N,N-Dimethylamino)pentylthio-Sar]-3-[N-methylisoleucine]-4-cyclosporin |
| 185 | S | 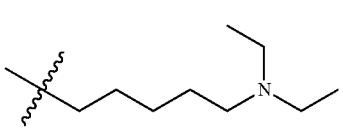 [SMILES: *CCCCCN(CC)CC] | [(R)-5-(N,N-Diethylamino)pentylthio-Sar]-3-[N-methylisoleucine]-4-cyclosporin |
| 186 | S | 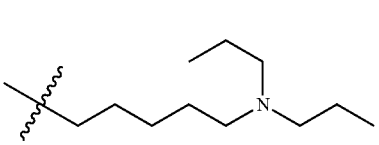 [SMILES: *CCCCCN(CCC)CCC] | [(R)-5-(N,N-Di-n-proylamino)pentylthio-Sar]-3-[N-methylisoleucine]-4-cyclosporin |
| 187 | S | 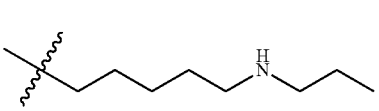 [SMILES: *CCCCCNCCC] | [(R)-5-(N-n-Propylamino)pentylthio-Sar]-3-[N-methylisoleucine]-4-cyclosporin |
| 188 | S | 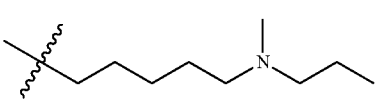 [SMILES: *CCCCCN(C)CCC] | [(R)-5-(N-n-Propyl-N-methylamino)pentylthio-Sar]-3-[N-methylisoleucine]-4-cyclosporin |

TABLE I-continued

| Ex. No. | W | R$_a$ | Name |
|---|---|---|---|
| 189 | S | | [(R)-5-(N-n-Propyl-N-ethylamino)pentylthio-Sar]-3-[N-methylisoleucine]-4-cyclosporin |
| 190 | S | | [(R)-5-(N,N-Di-iso-propylamino)pentylthio-Sar]-3-[N-methylisoleucine]-4-cyclosporin |
| 191 | S | | [(R)-5-(N-iso-Propylamino)pentylthio-Sar]-3-[N-methylisoleucine]-4-cyclosporin |
| 192 | S | | [(R)-5-(N-iso-Propyl-N-methylamino)pentlthio-Sar]-3-[N-methylisoleucine]-4-cyclosporin |
| 193 | S | | [(R)-5-(N-iso-Propyl-N-ethylamino)pentylthio-Sar]-3-[N-methylisoleucine]-4-cyclosporin |
| 194 | S | | [(R)-5-(N-iso-Butylamino)pentylthio-Sar]-3-[N-methylisoleucine]-4-cyclosporin |
| 195 | S | | [(R)-5-(N-iso-Butyl-N-methylamino)pentylthio-Sar]-3-[N-methylisoleucine]-4-cyclosporin |
| 196 | S | | [(R)-5-(N-iso-Butyl-N-ethylamino)pentylthio-Sar]-3-[N-methylisoleucine]-4-cyclosporin |
| 197 | S | | [(R)-5-(N-(2',2'-dimethyl)propylamino)pentylthio-Sar]-3-[N-methylisoleucine]-4-cyclosporin |
| 198 | S | | [(R)-5-(N-(2',2'-dimethyl)propyl-N-methylamino)pentylthio-Sar]-3-[N-methylisoleucine]-4-cyclosporin |
| 199 | S | | [(R)-5-(N-(2',2'-dimethyl)propyl-N-ethylamino)pentylthio-Sar]-3-[N-methylisoleucine]-4-cyclosporin |
| 200 | O | | [(R)-5-(N,N-Dimethylamino)pentyloxy-Sar]-3-[N-methylisoleucine]-4-cyclosporin |
| 201 | O | | [(R)-5-(N,N-Diethylamino)pentyloxy-Sar]-3-[N-methylisoleucine]-4-cyclosporin |

TABLE I-continued

| Ex. No. | W | Ra | Name |
|---|---|---|---|
| 202 | O | | [(R)-5-(N,N-Di-n-proylamino)pentyloxy-Sar]-3-[N-methylisoleucine]-4-cyclosporin |
| 203 | O | | [(R)-5-(N-n-Propylamino)pentyloxy-Sar]-3-[N-methylisoleucine]-4-cyclosporin |
| 204 | O | | [(R)-5-(N-n-Propyl-N-methylamino)pentyloxy-Sar]-3-[N-methylisoleucine]-4-cyclosporin |
| 205 | O | | [(R)-5-(N-n-Propyl-N-ethylamino)pentyloxy-Sar]-3-[N-methylisoleucine]-4-cyclosporin |
| 206 | O | | [(R)-5-(N,N-Di-iso-propylamino)pentyloxy-Sar]-3-[N-methylisoleucine]-4-cyclosporin |
| 207 | O | | [(R)-5-(N-iso-Propylamino)pentyloxy-Sar]-3-[N-methylisoleucine]-4-cyclosporin |
| 208 | O | | [(R)-5-(N-iso-Propyl-N-methylamino)pentyloxy-Sar]-3-[N-methylisoleucine]-4-cyclosporin |
| 209 | O | | [(R)-5-(N-iso-Propyl-N-ethylamino)pentyloxy-Sar]-3-[N-methylisoleucine]-4-cyclosporin |
| 210 | O | | [(R)-5-(N-iso-Butylamino)pentyloxy-Sar]-3-[N-methylisoleucine]-4-cyclosporin |
| 211 | O | | [(R)-S-(N-iso-Butyl-N-methylamino)pentyloxy-Sar]-3-[N-methylisoleucine]-4-cyclosporin |
| 212 | O | | [(R)-5-(N-iso-Butyl-N-ethylamino)pentyloxy-Sar]-3-[N-methylisoleucine]-4-cyclosporin |
| 213 | O | | [(R)-5-(N-(2',2'-dimethyl)propylamino)pentyloxy-Sar]-3-[N-methylisoleucine]-4-cyclosporin |
| 214 | O | | [(R)-5-(N-(2',2'-dimethyl)propyl-N-methylamino)pentyloxy-Sar]-3-[N-methylisoleucine]-4-cyclosporin |

TABLE I-continued

| Ex. No. | W | Name |
|---|---|---|
| 215 | O | [(R)-5-(N-(2',2'-dimethyl)propyl-N-ethylamino)pentyloxy-Sar]-3-[N-methylisoleucine]-4-cyclosporin |
| 216 | S | [(R)-Methylthio-Sar]-3-[N-methylisoleucine]-4-cyclosporin |
| 217 | S | [(R)-Ethylthio-Sar]-3-[N-methylisoleucine]-4-cyclosporin |
| 218 | S | [(R)-n-Propylthio-Sar]-3-[N-methylisoleucine]-4-cyclosporin |
| 219 | S | [(R)-iso-Butylthio-Sar]-3-[N-methylisoleucine]-4-cyclosporin |
| 220 | S | [(R)-iso-Pentylthio-Sar]-3-[N-methylisoleucine]-4-cyclosporin |
| 221 | S | [(R)-(4-Methyl)-Pentylthio-Sar]-3-[N-methylisoleucine]-4-cyclosporin |
| 222 | S | [(R)-2-Hydroxyethylthio-Sar]-3-[N-methylisoleucine]-4-cyclosporin |
| 223 | S | [(R)-2-Methoxyethylthio-Sar]-3-[N-methylisoleucine]-4-cyclosporin |
| 224 | S | [(R)-2-Ethoxyethylthio-Sar]-3-[N-methylisoleucine]-4-cyclosporin |
| 225 | S | [(R)-2-iso-Butoxyethylthio-Sar]-3-[N-methylisoleucine]-4-cyclosporin |
| 226 | S | [(R)-2-(2-Hydroxyethoxy)ethylthio-Sar]-3-[N-methylisoleucine]-4-cyclosporin |
| 227 | S | [(R)-2-(2-Methoxyethoxy)ethylthio-Sar]-3-[N-methylisoleucine]-4-cyclosporin |
| 228 | S | [(R)-2-(2-Ethoxyethoxy)ethylthio-Sar]-3-[N-methylisoleucine]-4-cyclosporin |

TABLE I-continued

| Ex. No. | W | R_a | Name |
|---|---|---|---|
| 229 | S | (structure: -CH2CH2-O-CH2CH2-O-CH2CH(CH3)2) | [(R)-2-(2-iso-Butoxyethoxy)ethylthio-Sar]-3-[N-methylisoleucine]-4-cyclosporin |
| 230 | S | (structure: -CH2CH2-O-CH2CH2-O-CH2CH2OH) | [(R)-2-[2-(2-Hydroxyethoxy)ethoxy]ethylthio-Sar]-3-[N-methylisoleucine]-4-cyclosporin |
| 231 | S | (structure: -CH2CH2-O-CH2CH2-O-CH2CH2-OCH3) | [(R)-2-[2-(2-Methoxyethoxy)ethoxy]ethylthio-Sar]-3-[N-methylisoleucine]-4-cyclosporin |
| 232 | S | (structure: -CH2CH2-O-CH2CH2-O-CH2CH2-OEt) | [(R)-2-[2-(2-Ethoxyethoxy)ethoxy]ethylthio-Sar]-3-[N-methylisoleucine]-4-cyclosporin |
| 233 | S | (structure: -CH2CH2-O-CH2CH2-O-CH2CH(CH3)2 extended) | [(R)-2-[2-(2-iso-Butoxyethoxy)ethoxythio-Sar]-3-[N-methylisoleucine]-4-cyclosporin |
| 234 | O | (methyl) | [(R)-Methoxy-Sar]-3-[N-methylisoleucine]-4-cyclosporin |
| 235 | O | (ethyl) | [(R)-Ethoxy-Sar]-3-[N-methylisoleucine]-4-cyclosporin |
| 236 | O | (n-propyl) | [(R)-n-Propoxy-Sar]-3-[N-methylisoleucine]-4-cyclosporin |
| 237 | O | (iso-butyl) | [(R)-iso-Butoxy-Sar]-3-[N-methylisoleucine]-4-cyclosporin |
| 238 | O | (iso-pentyl) | [(R)-iso-Pentyloxy-Sar]-3-[N-methylisoleucine]-4-cyclosporin |
| 239 | O | (4-methylpentyl) | [(R)-(4-Methyl)-Pentyloxy-Sar]-3-[N-methylisoleucine]-4-cyclosporin |
| 240 | O | (-CH2CH2OH) | [(R)-2-Hydroxyethoxy-Sar]-3-[N-methylisoleucine]-4-cyclosporin |
| 241 | O | (-CH2CH2OCH3) | [(R)-2-Methoxyethoxy-Sar]-3-[N-methylisoleucine]-4-cyclosporin |
| 242 | O | (-CH2CH2OEt) | [(R)-2-Ethoxyethoxy-Sar]-3-[N-methylisoleucine]-4-cyclosporin |
| 243 | O | (-CH2CH2-O-CH2CH(CH3)2) | [(R)-2-iso-Butoxyethoxy-Sar]-3-[N-methylisoleucine]-4-cyclosporin |

TABLE I-continued

| Ex. No. | W | $R_a$ | Name |
|---|---|---|---|
| 244 | O | (CH2CH2-O-CH2CH2-OH) | [(R)-2-(2-Hydroxyethoxy)ethoxy-Sar]-3-[N-methylisoleucine]-4-cyclosporin |
| 245 | O | (CH2CH2-O-CH2CH2-O-CH3) | [(R)-2-(2-Methoxyethoxy)ethoxy-Sar]-3-[N-methylisoleucine]-4-cyclosporin |
| 246 | O | (CH2CH2-O-CH2CH2-O-Et) | [(R)-2-(2-Ethoxyethoxy)ethoxy-Sar]-3-[N-methylisoleucine]-4-cyclosporin |
| 247 | O | (CH2CH2-O-CH2CH2-O-iBu) | [(R)-2-(2-iso-Butoxyethoxy)ethoxy-Sar]-3-[N-methylisoleucine]-4-cyclosporin |
| 248 | O | (CH2CH2-O-CH2CH2-O-CH2CH2-OH) | [(R)-2-[2-(2-Hydroxyethoxy)ethoxy]ethoxy-Sar]-3-[N-methylisoleucine]-4-cyclosporin |
| 249 | O | (CH2CH2-O-CH2CH2-O-CH2CH2-O-CH3) | [(R)-2-[2-(2-Methoxyethoxy)ethoxy]ethoxy-Sar]-3-[N-methylisoleucine]-4-cyclosporin |
| 250 | O | (CH2CH2-O-CH2CH2-O-CH2CH2-O-Et) | [(R)-2-[2-(2-Ethoxyethoxy)ethoxy]ethoxy-Sar]-3-[N-methylisoleucine]-4-cyclosporin |
| 251 | O | (CH2CH2-O-CH2CH2-O-CH2CH2-O-iBu) | [(R)-2-[2-(2-iso-Butoxyethoxy)ethoxy]ethoxy-Sar]-3-[N-methylisoleucine]-4-cyclosporin |

Examples 8-496

The following compounds can be prepared according to a method analogous to those described herein.

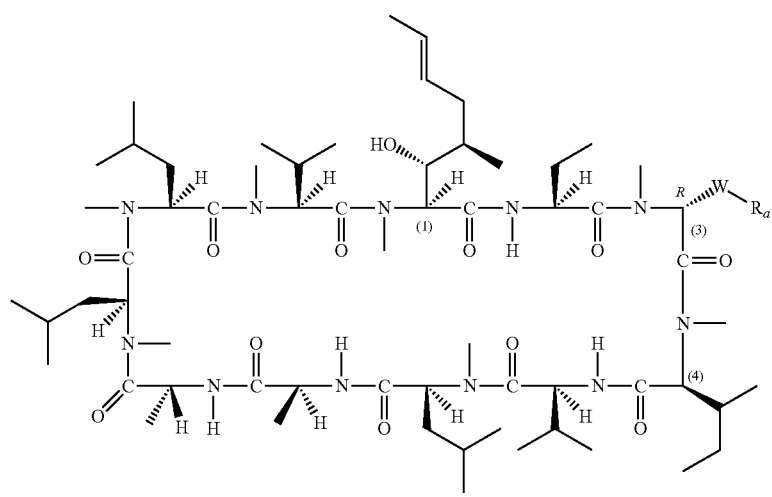

W = S, O

-continued

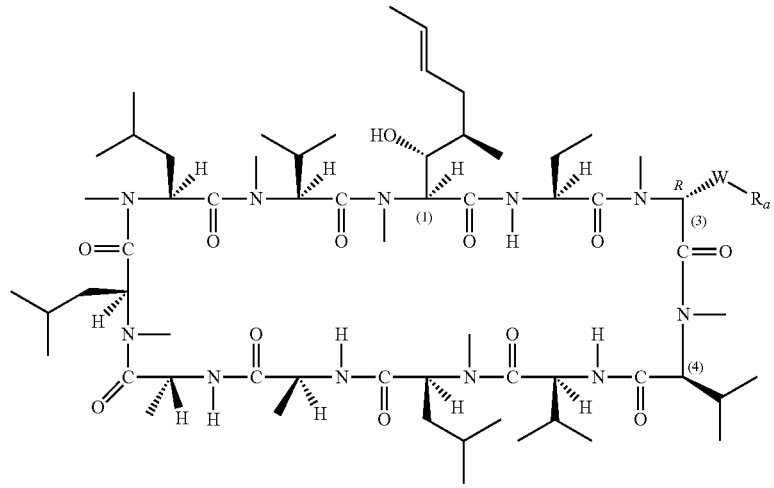

W = S, O

TABLE II

| Ex. | W | $R_a$ | Name |
|---|---|---|---|
| | | 2 Carbon Chain | |
| 252 | S | ![pyrrolidinyl] | [(R)-2-(N-Pyrrolidinyl)ethylthio-Sar]-3-[N-methylvaline]-4-cyclosporin |
| 253 | S | ![imidazolyl] | [(R)-2-(N-1H-Imidazolyl)ethylthio-Sar]-3-[N-methylvaline]-4-cyclosporin |
| 254 | S | ![piperidinyl] | [(R)-2-(N-Piperidinyl)ethylthio-Sar]-3-[N-methylvaline]-4-cyclosporin |
| 255 | S | ![morpholino] | [(R)-2-(N-Morpholino)ethylthio-Sar]-3-[N-methylvaline]-4-cyclosporin |
| 256 | S | ![thiomorpholino] | [(R)-2-(N-Thiomorpholino)ethylthio-Sar]-3-[N-methylvaline]-4-cyclosporin |
| 257 | S | ![piperazinyl] | [(R)-2-(Piperazinyl)ethylthio-Sar]-3-[N-methylvaline]-4-cyclosporin |
| 258 | S | ![methylpiperazinyl] | [(R)-2-(N-4-Methylpiperazinyl)ethylthio-Sar]-3-[N-methylvaline]-4-cyclosporin |

TABLE II-continued

| Ex. | W | R$_a$ | Name |
|---|---|---|---|
| 259 | S | | [(R)-2-(N-4-Ethylpiperazinyl)ethylthio-Sar]-3-[N-methylvaline]-4-cyclosporin |
| 260 | S | | [(R)-2-(N-4-n-Propylpiperazinyl)ethylthio-Sar]-3-[N-methylvaline]-4-cyclosporin |
| 261 | S | | [(R)-2-(N-4-iso-Propylpiperazinyl)ethylthio-Sar]-3-[N-methylvaline]-4-cyclosporin |
| 262 | O | | [(R)-2-(N-Pyrrolidinyl)ethoxy-Sar]-3-[N-methylvaline]-4-cyclosporin |
| 263 | O | | [(R)-2-(N-1H-Imidazolyl)ethoxy-Sar]-3-[N-methylvaline]-4-cyclosporin |
| 264 | O | | [(R)-2-(N-Piperidinyl)ethoxy-Sar]-3-[N-methylvaline]-4-cyclosporin |
| 265 | O | | [(R)-2-(N-Morpholino)ethoxy-Sar]-3-[N-methylvaline]-4-cyclosporin |
| 266 | O | | [(R)-2-(N-Thiomorpholino)ethoxy-Sar]-3-[N-methylvaline]-4-cyclosporin |
| 267 | O | | [(R)-2-(Piperazinyl)ethoxy-Sar]-3-[N-methylvaline]-4-cyclosporin |
| 268 | O | | [(R)-2-(N-4-Methylpiperazinyl)ethoxy-Sar]-3-[N-methylvaline]-4-cyclosporin |

TABLE II-continued

| Ex. | W | R$_a$ | Name |
|---|---|---|---|
| 269 | O | | [(R)-2-(N-4-Ethylpiperazinyl)ethoxy-Sar]-3-[N-methylvaline]-4-cyclosporin |
| 270 | O | | [(R)-2-(N-4-n-Propylpiperazinyl)ethoxy-Sar]-3-[N-methylvaline]-4-cyclosporin |
| 271 | O | | [(R)-2-(N-4-iso-Propylpiperazinyl)ethoxy-Sar]-3-[N-methylvaline]-4-cyclosporin |
| 272 | S | | [(R)-2-(N,N-Di-n-proylamino)ethylthio-Sar]-3-[N-methylvaline]-4-cyclosporin |
| 273 | S | | [(R)-2-(N-n-Propylamino)ethylthio-Sar]-3-[N-methylvaline]-4-cyclosporin |
| 274 | S | | [(R)-2-(N-n-Propyl-N-methylamino)ethylthio-Sar]-3-[N-methylvaline]-4-cyclosporin |
| 275 | S | | [(R)-2-(N-n-Propyl-N-ethylamino)ethylthio-Sar]-3-[N-methylvaline]-4-cyclosporin |
| 276 | S | | [(R)-2-(N,N-Di-iso-propylamino)ethylthio-Sar]-3-[N-methylvaline]-4-cyclosporin |
| 277 | S | | [(R)-2-(N-iso-Propylamino)ethylthio-Sar]-3-[N-methylvaline]-4-cyclosporin |
| 278 | S | | [(R)-2-(N-iso-Propyl-N-methylamino)ethylthio-Sar]-3-[N-methylvaline]-4-cyclosporin |
| 279 | S | | [(R)-2-(N-iso-Propyl-N-ethylamino)ethylthio-Sar]-3-[N-methylvaline]-4-cyclosporin |

TABLE II-continued

| Ex. | W | R$_a$ | Name |
|---|---|---|---|
| 280 | S | | [(R)-2-(N-iso-Butylamino)ethylthio-Sar]-3-[N-methylvaline]-4-cyclosporin |
| 281 | S | | [(R)-2-(N-iso-Butyl-N-methylamino)ethylthio-Sar]-3-[N-methylvaline]-4-cyclosporin |
| 282 | S | | [(R)-2-(N-iso-Butyl-N-ethylamino)ethylthio-Sar]-3-[N-methylvaline]-4-cyclosporin |
| 283 | S | | [(R)-2-(N-(2',2'-dimethyl)propylamino)ethylthio-Sar]-3-[N-methylvaline]-4-cyclosporin |
| 284 | S | | [(R)-2-(N-(2',2'-dimethyl)propyl-N-methylamino)ethylthio-Sar]-3-[N-methylvaline]-4-cyclosporin |
| 285 | S | | [(R)-2-(N-(2',2'-dimethyl)propyl-N-ethylamino)ethylthio-Sar]-3-[N-methylvaline]-4-cyclosporin |
| 286 | O | | [(R)-2-(N,N-Diethylamino)ethoxy-Sar]-3-[N-methylvaline]-4-cyclosporin |
| 287 | O | | [(R)-2-(N,N-Di-n-proylamino)ethoxy-Sar]-3-[N-methylvaline]-4-cyclosporin |
| 288 | O | | [(R)-2-(N-n-Propylamino)ethoxy-Sar]-3-[N-methylvaline]-4-cyclosporin |
| 289 | O | | [(R)-2-(N-n-Propyl-N-methylamino)ethoxy-Sar]-3-[N-methylvaline]-4-cyclosporin |
| 290 | O | | [(R)-2-(N-n-Propyl-N-ethylamino)ethoxy-Sar]-3-[N-methylvaline]-4-cyclosporin |

TABLE II-continued

| Ex. | W | R_a | Name |
|---|---|---|---|
| 291 | O | 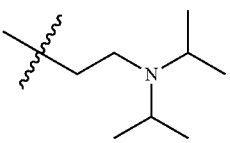 [SMILES: *CCN(C(C)C)C(C)C] | [(R)-2-(N,N-Di-iso-propylamino)-Sar]-3-[N-methylvaline]-4-cyclosporin |
| 292 | O | 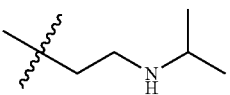 [SMILES: *CCNC(C)C] | [(R)-2-(N-iso-Propylamino)ethoxy-Sar]-3-[N-methylvaline]-4-cyclosporin |
| 293 | O | 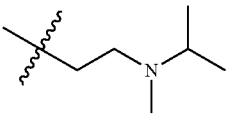 [SMILES: *CCN(C)C(C)C] | [(R)-2-(N-iso-Propyl-N-methylamino)ethoxy-Sar]-3-[N-methylvaline]-4-cyclosporin |
| 294 | O | 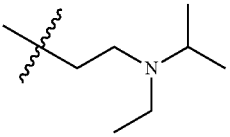 [SMILES: *CCN(CC)C(C)C] | [(R)-2-(N-iso-Propyl-N-ethylamino)ethoxy-Sar]-3-[N-methylvaline]-4-cyclosporin |
| 295 | O | 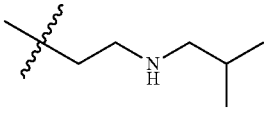 [SMILES: *CCNCC(C)C] | [(R)-2-(N-iso-Butylamino)ethoxy-Sar]-3-[N-methylvaline]-4-cyclosporin |
| 296 | O | 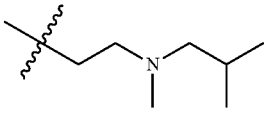 [SMILES: *CCN(C)CC(C)C] | [(R)-2-(N-iso-Butyl-N-methylamino)ethoxy-Sar]-3-[N-methylvaline]-4-cyclosporin |
| 297 | O | 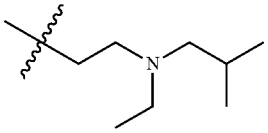 [SMILES: *CCN(CC)CC(C)C] | [(R)-2-(N-iso-Butyl-N-ethylamino)ethoxy-Sar]-3-[N-methylvaline]-4-cyclosporin |
| 298 | O | 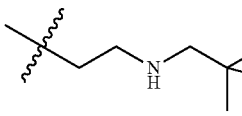 | [(R)-2-(N-(2',2'-dimethyl)propylamino)ethoxy-Sar]-3-[N-methylvaline]-4-cyclosporin |
| 299 | O | 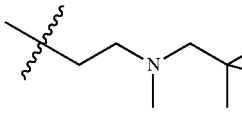 | [(R)-2-(N-(2',2'-dimethyl)propyl-N-methylamino)ethoxy-Sar]-3-[N-methylvaline]-4-cyclosporin |
| 300 | O | 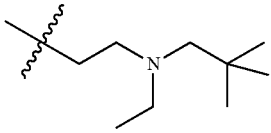 [SMILES: *CCN(CC)CC(C)(C)C] | [(R)-2-(N-(2',2'-dimethyl)propyl-N-ethylamino)ethoxy-Sar]-3-[N-methylvaline]-4-cyclosporin |
| | | 3 Carbon Chain | |
| 301 | S | 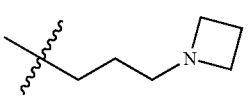 [SMILES: *CCCN1CCC1] | [(R)-3-(N-Azetidinyl)propylthio-Sar]-3-[N-methylvaline]-4-cyclosporin |
| 302 | S | 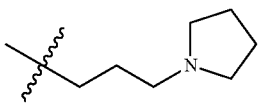 [SMILES: *CCCN1CCCC1] | [(R)-3-(N-Pyrrolidinyl)propylthio-Sar]-3-[N-methylvaline]-4-cyclosporin |

TABLE II-continued

| Ex. | W | $R_a$ | Name |
|---|---|---|---|
| 303 | S | 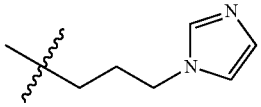 [SMILES: *CCCn1ccnc1] | [(R)-3-(N-1H-Imidazolyl)propylthio-Sar]-3-[N-methylvaline]-4-cyclosporin |
| 304 | S | 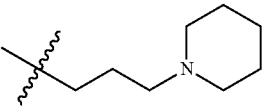 [SMILES: *CCCN1CCCCC1] | [(R)-3-(N-Piperidinyl)propylthio-Sar]-3-[N-methylvaline]-4-cyclosporin |
| 305 | S | 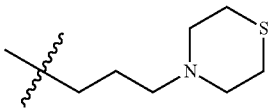 [SMILES: *CCCN1CCSCC1] | [(R)-3-(N-Thiomorpholino)propylthio-Sar]-3-[N-methylvaline]-4-cyclosporin |
| 306 | S | 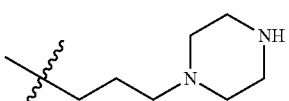 | [(R)-3-(Piperazinyl)propylthio-Sar]-3-[N-methylvaline]-4-cyclosporin |
| 307 | S | 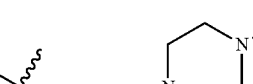 | [(R)-3-(N-4-Methylpiperazinyl)propylthio-Sar]-3-[N-methylvaline]-4-cyclosporin |
| 308 | S | 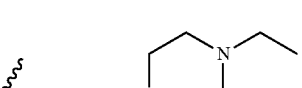 | [(R)3-(N-4-Ethylpiperazinyl)propylthio-Sar]-3-[N-methylvaline]-4-cyclosporin |
| 309 | S | 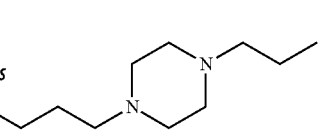 | [(R)-3-(N-4-n-Propylpiperazinyl)propylthio-Sar]-3-[N-methylvaline]-4-cyclosporin |
| 310 | S | 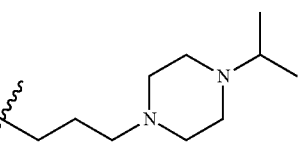 | [(R)-3-(N-4-iso-Propylpiperazinyl)propylthio-Sar]-3-[N-methylvaline]-4-cyclosporin |
| 311 | O | 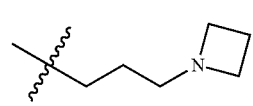 [SMILES: *CCCN1CCC1] | [(R)-3-(N-Azetidinyl)propoxy-Sar]-3-[N-methylvaline]-4-cyclosporin |
| 312 | O | 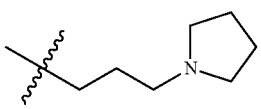 [SMILES: *CCCN1CCCC1] | [(R)-3-(N-Pyrrolidinyl)propoxy-Sar]-3-[N-methylvaline]-4-cyclosporin |
| 313 | O | 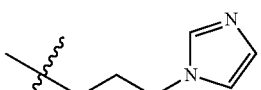 | [(R)-3-(N-1H-Imidazolyl)propoxy-Sar]-3-[N-methylvaline]-4-cyclosporin |
| 314 | O |  | [(R)-3-(N-Piperidinyl)propoxy-Sar]-3-[N-methylvaline]-4-cyclosporin |

TABLE II-continued

| Ex. | W | R$_a$ | Name |
|---|---|---|---|
| 315 | O | | [(R)-3-(N-Morpholino)propoxy-Sar]-3-[N-methylvaline]-4-cyclosporin |
| 316 | O | | [(R)-3-(N-Thiomorpholino)propoxy-Sar]-3-[N-methylvaline]-4-cyclosporin |
| 317 | O | | [(R)-3-(Piperazinyl)propoxy-Sar]-3-[N-methylvaline]-4-cyclosporin |
| 318 | O | | [(R)-3-(N-4-Methylpiperazinyl)propoxy-Sar]-3-[N-methylvaline]-4-cyclosporin |
| 319 | O | | [(R)-3-(N-4-Ethylpiperazinyl)propoxy-Sar]-3-[N-methylvaline]-4-cyclosporin |
| 320 | O | | [(R)-3-(N-4-n-Propylpiperazinyl)propoxy-Sar]-3-[N-methylvaline]-4-cyclosporin |
| 321 | O | | [(R)-3-(N-4-iso-Propylpiperazinyl)propoxy-Sar]-3-[N-methylvaline]-4-cyclosporin |
| 322 | S | | [(R)-3-(N,N-Dimethylamino)propylthio-Sar]-3-[N-methylvaline]-4-cyclosporin |
| 323 | S | | [(R)-3-(N,N-Di-n-proylamino)propylthio-Sar]-3-[N-methylvaline]-4-cyclosporin |
| 324 | S | | [(R)-3-(N-n-Propylamino)propylthio-Sar]-3-[N-methylvaline]-4-cyclosporin |
| 325 | S | | [(R)-3-(N-n-Propyl-N-methylamino)propylthio-Sar]-3-[N-methylvaline]-4-cyclosporin |
| 326 | S | | [(R)-3-(N-n-Propyl-N-ethylamino)propylthio-Sar]-3-[N-methylvaline]-4-cyclosporin |

TABLE II-continued

| Ex. | W | R$_a$ | Name |
|---|---|---|---|
| 327 | S | | [(R)-3-(N,N-Di-iso-propylamino)propylthio-Sar]-3-[N-methylvaline]-4-cyclosporin |
| 328 | S | | [(R)-3-(N-iso-Propylamino)propylthio-Sar]-3-[N-methylvaline]-4-cyclosporin |
| 329 | S | | [(R)-3-(N-iso-Propyl-N-methylamino)propylthio-Sar]-3-[N-methylvaline]-4-cyclosporin |
| 330 | S | | [(R)-3-(N-iso-Propyl-N-ethylamino)propylthio-Sar]-3-[N-methylvaline]-4-cyclosporin |
| 331 | S | | [(R)-3-(N-iso-Butylamino)propylthio-Sar]-3-[N-methylvaline]-4-cyclosporin |
| 332 | S | | [(R)-3-(N-iso-Butyl-N-methylamino)propylthio-Sar]-3-[N-methylvaline]-4-cyclosporin |
| 333 | S | | [(R)-3-(N-iso-Butyl-N-ethylamino)propylthio-Sar]-3-[N-methylvaline]-4-cyclosporin |
| 334 | S | | [(R)-3-(N-(2',2'-dimethyl)propylamino)propylthio-Sar]-3-[N-methylvaline]-4-cyclosporin |
| 335 | S | | [(R)-3-(N-(2',2'-dimethyl)propyl-N-methylamino)propylthio-Sar]-3-[N-methylvaline]-4-cyclosporin |
| 336 | S | | [(R)-3-(N-(2',2'-dimethyl)propyl-N-ethylamino)propylthio-Sar]-3-[N-methylvaline]-4-cyclosporin |
| 337 | O | | [(R)-3-(N,N-Dimethylamino)propoxy-Sar]-3-[N-methylvaline]-4-cyclosporin |
| 338 | O | | [(R)-3-(N,N-Diethylamino)propoxy-Sar]-3-[N-methylvaline]-4-cyclosporin |
| 339 | O | | [(R)-3-(N,N-Di-n-proylamino)propoxy-Sar]-3-[N-methylvaline]-4-cyclosporin | ns
TABLE II-continued

| Ex. | W | Name |
|-----|---|------|
| 340 | O | [(R)-3-(N-n-Propylamino)propoxy-Sar]-3-[N-methylvaline]-4-cyclosporin |
| 341 | O | [(R)-3-(N-n-Propyl-N-methylamino)propoxy-Sar]-3-[N-methylvaline]-4-cyclosporin |
| 342 | O | [(R)-3-(N-n-Propyl-N-ethylamino)propoxy-Sar]-3-[N-methylvaline]-4-cyclosporin |
| 343 | O | [(R)-3-(N,N-Di-iso-propylamino)propoxy-Sar]-3-[N-methylvaline]-4-cyclosporin |
| 344 | O | [(R)-3-(N-iso-Propylamino)propoxy-Sar]-3-[N-methylvaline]-4-cyclosporin |
| 345 | O | [(R)-3-(N-iso-Propyl-N-methylamino)propoxy-Sar]-3-[N-methylvaline]-4-cyclosporin |
| 346 | O | [(R)-3-(N-iso-Propyl-N-ethylamino)propoxy-Sar]-3-[N-methylvaline]-4-cyclosporin |
| 347 | O | [(R)-3-(N-iso-Butylamino)propoxy-Sar]-3-[N-methylvaline]-4-cyclosporin |
| 348 | O | [(R)-3-(N-iso-Butyl-N-methylamino)propoxy-Sar]-3-[N-methylvaline]-4-cyclosporin |
| 349 | O | [(R)-3-(N-iso-Butyl-N-ethylamino)propoxy-Sar]-3-[N-methylvaline]-4-cyclosporin |
| 350 | O | [(R)-3-(N-(2',2'-dimethyl)propylamino(propoxy-Sar]-3-[N-methylvaline]-4-cyclosporin |
| 351 | O | [(R)-3-(N-(2',2'-dimethyl)propyl-N-methylamino)propoxy-Sar]-3-[N-methylvaline]-4-cyclosporin |
| 352 | O | [(R)-3-(N-(2',2'-dimethyl)propyl-N-ethylamino)propoxy-Sar]-3-[N-methylvaline]-4-cyclosporin |

TABLE II-continued

| Ex. | W | R_a | Name |
|---|---|---|---|
| | | 4 Carbon Chain | |
| 353 | S | (azetidine, 4-carbon chain) | [(R)-4-(N-Azetidinyl)Butylthio-Sar]-3-[N-methylvaline]-4-cyclosporin |
| 354 | S | (pyrrolidine, 4-carbon chain) | [(R)-4-(N-Pyrrolidinyl)Butylthio-Sar]-3-[N-methylvaline]-4-cyclosporin |
| 355 | S | (imidazole, 4-carbon chain) | [(R)-4-(N-1H-Imidazolyl)Butylthio-Sar]-3-[N-methylvaline]-4-cyclosporin |
| 356 | S | (piperidine, 4-carbon chain) | [(R)-4-(N-Piperidinyl)Butylthio-Sar]-3-[N-methylvaline]-4-cyclosporin |
| 357 | S | (morpholine, 4-carbon chain) | [(R)-4-(N-Morpholino)Butylthio-Sar]-3-[N-methylvaline]-4-cyclosporin |
| 358 | S | (thiomorpholine, 4-carbon chain) | [(R)-4-(N-Thiomorpholino)Butylthio-Sar]-3-[N-methylvaline]-4-cyclosporin |
| 359 | S | (piperazine, 4-carbon chain) | [(R)-4-(Piperazinyl)Butylthio-Sar]-3-[N-methylvaline]-4-cyclosporin |
| 360 | S | (N-methylpiperazine, 4-carbon chain) | [(R)-4-(N-4-Methylpiperazinyl)Butylthio-Sar]-3-[N-methylvaline]-4-cyclosporin |
| 361 | S | (N-ethylpiperazine, 4-carbon chain) | [(R)-4-(N-4-Ethylpiperazinyl)Butylthio-Sar]-3-[N-methylvaline]-4-cyclosporin |
| 362 | S | (N-propylpiperazine, 4-carbon chain) | [(R)-4-(N-4-n-Propylpiperazinyl)Butylthio-Sar]-3-[N-methylvaline]-4-cyclosporin |

TABLE II-continued

| Ex. | W | $R_a$ | Name |
|---|---|---|---|
| 363 | S | 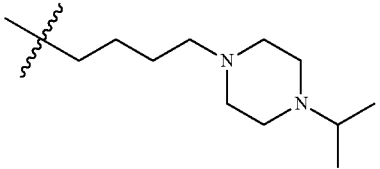 [SMILES: *CCCCN1CCN(C(C)C)CC1] | [(R)-4-(N-4-iso-Propylpiperazinyl)Butylthio-Sar]-3-[N-methylvaline]-4-cyclosporin |
| 364 | O | 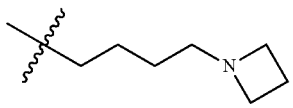 [SMILES: *CCCCN1CCC1] | [(R)-4-(N-Azetidinyl)Butoxy-Sar]-3-[N-methylvaline]-4-cyclosporin |
| 365 | O | 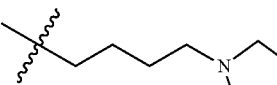 | [(R)-4-(N-Pyrrolidinyl)Butoxy-Sar]-3-[N-methylvaline]-4-cyclosporin |
| 366 | O | 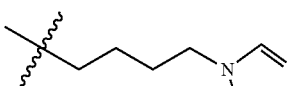 | [(R)-4-(N-1H-Imidazolyl)Butoxy-Sar]-3-[N-methylvaline]-4-cyclosporin |
| 367 | O | 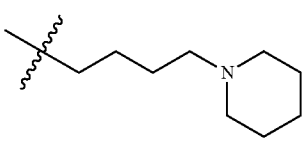 [SMILES: *CCCCN1CCCCC1] | [(R)-4-(N-Piperidinyl)Butoxy-Sar]-3-[N-methylvaline]-4-cyclosporin |
| 368 | O | 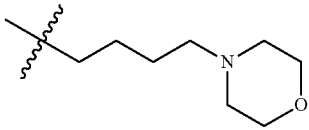 [SMILES: *CCCCN1CCOCC1] | [(R)-4-(N-Morpholino)Butoxy-Sar]-3-[N-methylvaline]-4-cyclosporin |
| 369 | O | 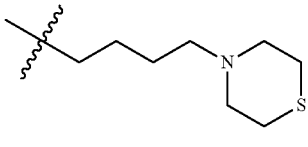 [SMILES: *CCCCN1CCSCC1] | [(R)-4-(N-Thiomorpholino)Butoxy-Sar]-3-[N-methylvaline]-4-cyclosporin |
| 370 | O | 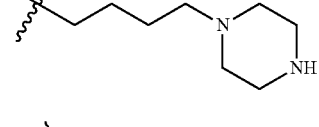 | [(R)-4-(Piperazinyl)Butoxy-Sar]-3-[N-methylvaline]-4-cyclosporin |
| 371 | O | 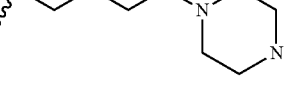 | [(R)-4-(N-4-Methylpiperazinyl)Butoxy-Sar]-3-[N-methylvaline-4-cyclosporin |
| 372 | O | 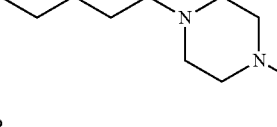 | [(R)-4-(N-4-Ethylpiperazinyl)Butoxy-Sar]-3-[N-methylvaline]-4-cyclosporin |
| 373 | O | 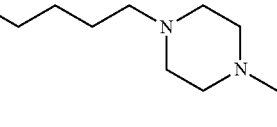 | [(R)-4-(N-4-n-Propylpiperazinyl)Butoxy-Sar]-3-[N-methylvaline]-4-cyclosporin |

TABLE II-continued

| Ex. | W | R$_a$ | Name |
|---|---|---|---|
| 374 | O | | [(R)-4-(N-4-iso-Propylpiperazinyl)Butoxy-Sar]-3-[N-methylvaline]-4-cyclosporin |
| 375 | S | | [(R)-4-(N,N-Dimethylamino)butylthio-Sar]-3-[N-methylvaline]-4-cyclosporin |
| 376 | S | | [(R)-4-(N,N-Diethylamino)butylthio-Sar]-3-[N-methylvaline]-4-cyclosporin |
| 377 | S | | [(R)-4-(N,N-Di-n-proylamino)butylthio-Sar]-3-[N-methylvaline]-4-cyclosporin |
| 378 | S | | [(R)-4-(N-n-Propylamino)butylthio-Sar]-3-[N-methylvaline]-4-cyclosporin |
| 379 | S | | [(R)-4-(N-n-Propyl-N-methylamino)butylthio-Sar]-3-[N-methylvaline]-4-cyclosporin |
| 380 | S | | [(R)-4-(N-n-Propyl-N-ethylamino)butylthio-Sar]-3-[N-methylvaline]-4-cyclosporin |
| 381 | S | | [(R)-4-(N,N-Di-iso-propylamino)butylthio-Sar]-3-[N-methylvaline]-4-cyclosporin |
| 382 | S | | [(R)-4-(N-iso-Propylamino)butylthio-Sar]-3-[N-methylvaline]-4-cyclosporin |
| 383 | S | | [(R)-4-(N-iso-Propyl-N-methylamino)butylthio-Sar]-3-[N-methylvaline]-4-cyclosporin |
| 384 | S | | [(R)-4-(N-iso-Propyl-N-ethylamino)butylthio-Sar]-3-[N-methylvaline]-4-cyclosporin |

TABLE II-continued

| Ex. | W | R_a | Name |
|---|---|---|---|
| 385 | S | | [(R)-4-(N-iso-Butylamino)butylthio-Sar]-3-[N-methylvaline]-4-cyclosporin |
| 386 | S | | [(R)-4-(N-iso-Butyl-N-methylamino)butylthio-Sar]-3-[N-methylvaline]-4-cyclosporin |
| 387 | S | | [(R)-4-(N-iso-Butyl-N-ethylamino)butylthio-Sar]-3-[N-methylvaline]-4-cyclosporin |
| 388 | S | | [(R)-4-(N-(2',2'-dimethyl)propylamino)butylthio-Sar]-3-[N-methylvaline]-4-cyclosporin |
| 389 | S | | [(R)-4-(N-(2',2'-dimethyl)propyl-N-methylamino)butylthio-Sar]-3-[N-methylvaline]-4-cyclosporin |
| 390 | S | | [(R)-4-(N-(2',2'-dimethyl)propyl-N-ethylamino)butylthio-Sar]-3-[N-methylvaline]-4-cyclosporin |
| 391 | O | | [(R)-4-(N,N-Dimethylamino)butoxy-Sar]-3-[N-methylvaline]-4-cyclosporin |
| 392 | O | | [(R)-4-(N,N-Diethylamino)butoxy-Sar]-3-[N-methylvaline]-4-cyclosporin |
| 393 | O | | [(R)-4-(N,N-Di-n-proylamino)butoxy-Sar]-3-[N-methylvaline]-4-cyclosporin |
| 394 | O | | [(R)-4-(N-n-Propylamino)butoxy-Sar]-3-[N-methylvaline]-4-cyclosporin |
| 395 | O | | [(R)-4-(N-n-Propyl-N-methylamino)butoxy-Sar]-3-[N-methylvaline]-4-cyclosporin |
| 396 | O | | [(R)-4-(N-n-Propyl-N-ethylamino)butoxy-Sar]-3-[N-methylvaline]-4-cyclosporin |

TABLE II-continued

| Ex. | W | R$_a$ | Name |
|---|---|---|---|
| 397 | O | | [(R)-4-(N,N-Di-iso-propylamino)butoxy-Sar]-3-[N-methylvaline]-4-cyclosporin |
| 398 | O | | [(R)-4-(N-iso-Propylamino)butoxy-Sar]-3-[N-methylvaline]-4-cyclosporin |
| 399 | O | | [(R)-4-(N-iso-Propyl-N-methylamino)butoxy-Sar]-3-[N-methylvaline]-4-cyclosporin |
| 400 | O | | [(R)-4-(N-iso-Propyl-N-ethylamino)butoxy-Sar]-3-[N-methylvaline]-4-cyclosporin |
| 401 | O | | [(R)-4-(N-iso-Butylamino)butoxy-Sar]-3-[N-methylvaline]-4-cyclosporin |
| 402 | O | | [(R)-4-(N-iso-Butyl-N-methylamino)butoxy-Sar]-3-[N-methylvaline]-4-cyclosporin |
| 403 | O | | [(R)-4-(N-iso-Butyl-N-ethylamino)butoxy-Sar]-3-[N-methylvaline]-4-cyclosporin |
| 404 | O | | [(R)-4-(N-(2',2'-dimethyl)propylamino)butoxy-Sar]-3-[N-methylvaline]-4-cyclosporin |
| 405 | O | | [(R)-4-(N-(2',2'-dimethyl)propyl-N-methylamino)butoxy-Sar]-3-[N-methylvaline]-4-cyclosporin |
| 406 | O | | [(R)-4-(N-(2',2'-dimethyl)propyl-N-ethylamino)butoxy-Sar]-3-[N-methylvaline]-4-cyclosporin |
| 5 Carbon Chain | | | |
| 407 | S | | [(R)-5-(N-Azetidinyl)pentylthio-Sar]-3-[N-methylvaline]-4-cyclosporin |
| 408 | S | | [(R)-5-(N-Pyrrolidinyl)pentylthio-Sar]-3-[N-methylvaline]-4-cyclosporin |

TABLE II-continued

| Ex. | W | R$_a$ | Name |
|---|---|---|---|
| 409 | S |  | [(R)-5-(N-1H-Imidazolyl)pentylthio-Sar]-3-[N-methylvaline]-4-cyclosporin |
| 410 | S |  | [(R)-5-(N-Piperidinyl)pentylthio-Sar]-3-[N-methylvaline]-4-cyclosporin |
| 411 | S |  | [(R)-5-(N-Morpholino)pentylthio-Sar]-3-[N-methylvaline]-4-cyclosporin |
| 412 | S |  | [(R)-5-(N-Thiomorpholino)pentylthio-Sar]-3-[N-methylvaline]-4-cyclosporin |
| 413 | S |  | [(R)-5-(Piperazinyl)pentylthio-Sar]-3-[N-methylvaline]-4-cyclosporin |
| 414 | S |  | [(R)-5-(N-4-Methylpiperazinyl)pentylthio-Sar]-3-[N-methylvaline]-4-cyclosporin |
| 415 | S |  | [(R)-5-(N-4-Ethylpiperazinyl)pentylthio-Sar]-3-[N-methylvaline]-4-cyclosporin |
| 416 | S |  | [(R)-5-(N-4-n-Propylpiperazinyl)pentylthio-Sar]-3-[N-methylvaline]-4-cyclosporin |
| 417 | S |  | [(R)-5-(N-4-iso-Propylpiperazinyl)pentylthio-Sar]-3-[N-methylvaline]-4-cyclosporin |
| 418 | O |  | [(R)-5-(N-Azetidinyl)pentyloxy-Sar]-3-[N-methylvaline]-4-cyclosporin |
| 419 | O |  | [(R)-5-(N-Pyrrolidinyl)pentyloxy-Sar]-3-[N-methylvaline]-4-cyclosporin |
| 420 | O |  | [(R)-5-(N-1H-Imidazolyl)pentyloxy-Sar]-3-[N-methylvaline]-4-cyclosporin |

TABLE II-continued

| Ex. | W | R$_a$ | Name |
|---|---|---|---|
| 421 | O | (5-pentyl chain to N-piperidinyl) | [(R)-5-(N-Piperidinyl)pentyloxy-Sar]-3-[N-methylvaline]-4-cyclosporin |
| 422 | O | (5-pentyl chain to N-morpholino) | [(R)-5-(N-Morpholino)pentyloxy-Sar]-3-[N-methylvaline]-4-cyclosporin |
| 423 | O | (5-pentyl chain to N-thiomorpholino) | [(R)-5-(N-Thiomorpholino)pentyloxy-Sar]-3-[N-methylvaline]-4-cyclosporin |
| 424 | O | (5-pentyl chain to piperazinyl-NH) | [(R)-5-(Piperazinyl)pentyloxy-Sar]-3-[N-methylvaline]-4-cyclosporin |
| 425 | O | (5-pentyl chain to N-4-methylpiperazinyl) | [(R)-5-(N-4-Methylpiperazinyl)pentyloxy-Sar]-3-[N-methylvaline]-4-cyclosporin |
| 426 | O | (5-pentyl chain to N-4-ethylpiperazinyl) | [(R)-5-(N-4-Ethylpiperazinyl)pentyloxy-Sar]-3-[N-methylvaline]-4-cyclosporin |
| 427 | O | (5-pentyl chain to N-4-n-propylpiperazinyl) | [(R)-5-(N-4-n-Propylpiperazinyl)pentyloxy-Sar]-3-[N-methylvaline]-4-cyclosporin |
| 428 | O | (5-pentyl chain to N-4-iso-propylpiperazinyl) | [(R)-5-(N-4-iso-Propylpiperazinyl)pentyloxy-Sar]-3-[N-methylvaline]-4-cyclosporin |
| 429 | S | (5-pentyl chain to N,N-dimethylamino) | [(R)-5-(N,N-Dimethylamino)pentylthio-Sar]-3-[N-methylvaline]-4-cyclosporin |
| 430 | S | (5-pentyl chain to N,N-diethylamino) | [(R)-5-(N,N-Diethylamino)pentylthio-Sar]-3-[N-methylvaline]-4-cyclosporin |
| 431 | S | (5-pentyl chain to N,N-di-n-propylamino) | [(R)-5-(N,N-Di-n-proylamino)pentylthio-Sar]-3-[N-methylvaline]-4-cyclosporin |
| 432 | S | (5-pentyl chain to N-n-propylamino) | [(R)-5-(N-n-Propylamino)pentylthio-Sar]-3-[N-methylvaline]-4-cyclosporin |

TABLE II-continued

| Ex. | W | $R_a$ | Name |
|---|---|---|---|
| 433 | S | | [(R)-5-(N-n-Propyl-N-methylamino)pentylthio-Sar]-3-[N-methylvaline]-4-cyclosporin |
| 434 | S | | [(R)-5-(N-n-Propyl-N-ethylamino)pentylthio-Sar]-3-[N-methylvaline]-4-cyclosporin |
| 435 | S | | [(R)-5-(N,N-Di-iso-propylamino)pentylthio-Sar]-3-[N-methylvaline]-4-cyclosporin |
| 436 | S | | [(R)-5-(N-iso-Propylamino)pentylthio-Sar]-3-[N-methylvaline]-4-cyclosporin |
| 437 | S | | [(R)-5-(N-iso-Propyl-N-methylamino)pentylthio-Sar]-3-[N-methylvaline]-4-cyclosporin |
| 438 | S | | [(R)-5-(N-iso-Propyl-N-ethylamino)pentylthio-Sar]-3-[N-methylvaline]-4-cyclosporin |
| 439 | S | | [(R)-5-(N-iso-Butylamino)pentylthio-Sar]-3-[N-methylvaline]-4-cyclosporin |
| 440 | S | | [(R)-5-(N-iso-Butyl-N-methylamino)pentylthio-Sar]-3-[N-methylvaline]-4-cyclosporin |
| 441 | S | | [(R)-5-(N-iso-Butyl-N-ethylamino)pentylthio-Sar]-3-[N-methylvaline]-4-cyclosporin |
| 442 | S | | [(R)-5-(N-(2',2'-dimethyl)propylamino)pentylthio-Sar]-3-[N-methylvaline]-4-cyclosporin |
| 443 | S | | [(R)-5-(N-(2',2'-dimethyl)propyl-N-methylamino)pentylthio-Sar]-3-[N-methylvaline]-4-cyclosporin |
| 444 | S | | [(R)-5-(N-(2',2'-dimethyl)propyl-N-ethylamino)pentylthio-Sar]-3-[N-methylvaline]-4-cyclosporin |
| 445 | O | | [(R)-5-(N,N-Dimethylamino)pentyloxy-Sar]-3-[N-methylvaline]-4-cyclosporin |

TABLE II-continued

| Ex. | W | Ra | Name |
|---|---|---|---|
| 446 | O | 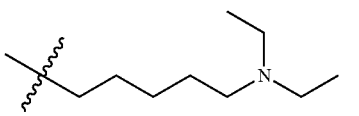 [SMILES: *CCCCCN(CC)CC] | [(R)-5-(N,N-Diethylamino)pentyloxy-Sar]-3-[N-methylvaline]-4-cyclosporin |
| 447 | O | 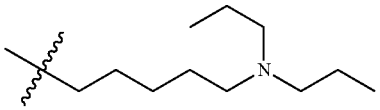 [SMILES: *CCCCCN(CCC)CCC] | [(R)-5-(N,N-Di-n-proylamino)pentyloxy-Sar]-3-[N-methylvaline]-4-cyclosporin |
| 448 | O | 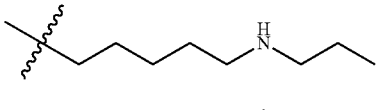 | [(R)-5-(N-n-Propylamino)pentyloxy-Sar]-3-[N-methylvaline]-4-cyclosporin |
| 449 | O | 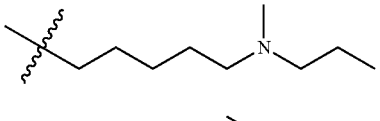 | [(R)-5-(N-n-Propyl-N-methylamino)pentyloxy-Sar]-3-[N-methylvaline]-4-cyclosporin |
| 450 | O | 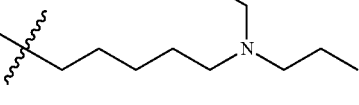 | [(R)-5-(N-n-Propyl-N-ethylamino)pentyloxy-Sar]-3-[N-methylvaline]-4-cyclosporin |
| 451 | O | 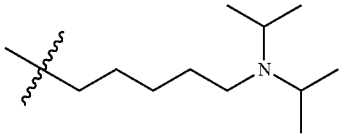 [SMILES: *CCCCCN(C(C)C)C(C)C] | [(R)-5-(N,N-Di-iso-propylamino)pentyloxy-Sar]-3-[N-methylvaline]-4-cyclosporin |
| 452 | O | 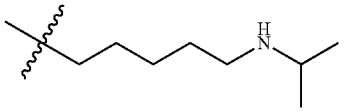 [SMILES: *CCCCCNC(C)C] | [(R)-5-(N-iso-Propylamino)pentyloxy-Sar]-3-[N-methylvaline]-4-cyclosporin |
| 453 | O | 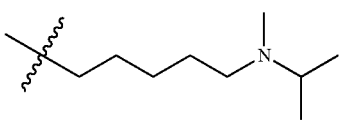 [SMILES: *CCCCCN(C)C(C)C] | [(R)-5-(N-iso-Propyl-N-methylamino)pentyloxy-Sar]-3-[N-methylvaline]-4-cyclosporin |
| 454 | O | 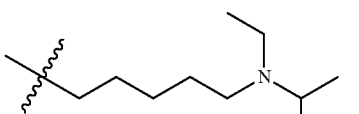 [SMILES: *CCCCCN(CC)CC] | [(R)-5-(N-iso-Propyl-N-ethylamino)pentyloxy-Sar]-3-[N-methylvaline]-4-cyclosporin |
| 455 | O |  | [(R)-5-(N-iso-Butylamino)pentyloxy-Sar]-3-[N-methylvaline]-4-cyclosporin |
| 456 | O | 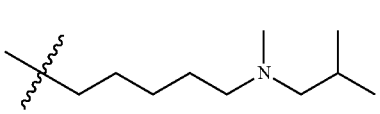 | [(R)-5-(N-iso-Butyl-N-methylamino)pentyloxy-Sar]-3-[N-methylvaline]-4-cyclosporin |
| 457 | O | 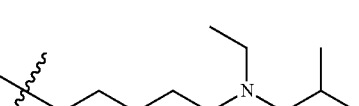 | [(R)-5-(N-iso-Butyl-N-ethylamino)pentyloxy-Sar]-3-[N-methylvaline]-4-cyclosporin |
| 458 | O | 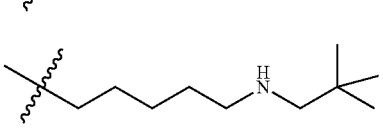 | [(R)-5-(N-(2',2'-dimethyl)propylamino)pentyloxy-Sar]-3-[N-methylvaline]-4-cyclosporin |

TABLE II-continued

| Ex. | W | R_a | Name |
|---|---|---|---|
| 459 | O | | [(R)-5-(N-(2',2'-dimethyl)propyl-N-methylamino)pentyloxy-Sar]-3-[N-methylvaline]-4-cyclosporin |
| 460 | O | | [(R)-5-(N-(2',2'-dimethyl)propyl-N-ethylamino)pentyloxy-Sar]-3-[N-methylvaline]-4-cyclosporin |
| 461 | S | | [(R)-Methylthio-Sar]-3-[N-methylvaline]-4-cyclosporin |
| 462 | S | | [(R)-Ethylthio-Sar]-3-[N-methylvaline]-4-cyclosporin |
| 463 | S | | [(R)-n-Propylthio-Sar]-3-[N-methylvaline]-4-cyclosporin |
| 464 | S | | [(R)-iso-Butylthio-Sar]-3-[N-methylvaline]-4-cyclosporin |
| 465 | S | | [(R)-iso-Pentylthio-Sar]-3-[N-methylvaline]-4-cyclosporin |
| 466 | S | | [(R)-(4-Methyl)-Pentylthio-Sar]-3-[N-methylvaline]-4-cyclosporin |
| 467 | S | | [(R)-2-Hydroxyethylthio-Sar]-3-[N-methylvaline]-4-cyclosporin |
| 468 | S | | [(R)-2-Methoxyethylthio-Sar]-3-[N-methylvaline]-4-cyclosporin |
| 469 | S | | [(R)-2-Ethoxyethylthio-Sar]-3-[N-methylvaline]-4-cyclosporin |
| 470 | S | | [(R)-2-iso-Butoxyethylthio-Sar]-3-[N-methylvaline]-4-cyclosporin |
| 471 | S | | [(R)-2-(2-Hydroxyethoxy)ethylthio-Sar]-3-[N-methylvaline]-4-cyclosporin |

TABLE II-continued

| Ex. | W | R$_a$ | Name |
|---|---|---|---|
| 472 | S | (structure) | [(R)-2-(2-Methoxyethoxy)ethylthio-Sar]-3-[N-methylvaline]-4-cyclosporin |
| 473 | S | (structure) | [(R)-2-(2-Ethoxyethoxy)ethylthio-Sar]-3-[N-methylvaline]-4-cyclosporin |
| 474 | S | (structure) | [(R)-2-(2-iso-Butoxyethoxy)ethylthio-Sar]-3-[N-methylvaline]-4-cyclosporin |
| 475 | S | (structure) | [(R)-2-[2-(2-Hydroxyethoxy)ethoxy]ethylthio-Sar]-3-[N-methylvaline]-4-cyclosporin |
| 476 | S | (structure) | [(R)-2-[2-(2-Methoxyethoxy)ethoxy]ethylthio-Sar]-3-[N-methylvaline]-4-cyclosporin |
| 477 | S | (structure) | [(R)-2-[2-(2-Ethoxyethoxy)ethoxy]ethylthio-Sar]-3-[N-methylvaline]-4-cyclosporin |
| 478 | S | (structure) | [(R)-2-[2-(2-iso-Butoxyethoxy)ethoxy]ethylthio-Sar]-3-[N-methylvaline]-4-cyclosporin |
| 479 | O | (structure) | [(R)-Methoxy-Sar]-3-[N-methylvaline]-4-cyclosporin |
| 480 | O | (structure) | [(R)-Ethoxy-Sar]-3-[N-methylvaline]-4-cyclosporin |
| 481 | O | (structure) | [(R)-n-Propoxy-Sar]-3-[N-methylvaline]-4-cyclosporin |
| 482 | O | (structure) | [(R)-iso-Butoxy-Sar]-3-[N-methylvaline]-4-cyclosporin |
| 483 | O | (structure) | [(R)-iso-Pentyloxy-Sar]-3-[N-methylvaline]-4-cyclosporin |
| 484 | O | (structure) | [(R)-(4-Methyl)-Pentyloxy-Sar]-3-[N-methylvaline]-4-cyclosporin |
| 485 | O | (structure) | [(R)-2-Hydroxyethoxy-Sar]-3-[N-methylvaline]-4-cyclosporin |

TABLE II-continued

| Ex. | W | R_a | Name |
|---|---|---|---|
| 486 | O | 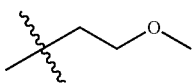 [SMILES: *CCOC] | [(R)-2-Methoxyethoxy-Sar]-3-[N-methylvaline]-4-cyclosporin |
| 487 | O | 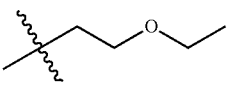 [SMILES: *CCOCC] | [(R)-2-Ethoxyethoxy-Sar]-3-[N-methylvaline]-4-cyclosporin |
| 488 | O | 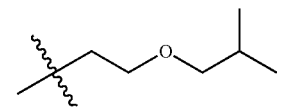 [SMILES: *CCOCC(C)C] | [(R)-2-iso-Butoxyethoxy-Sar]-3-[N-methylvaline]-4-cyclosporin |
| 489 | O | 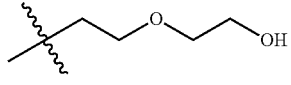 [SMILES: *CCOCCO] | [(R)-2-(2-Hydroxyethoxy)ethoxy-Sar]-3-[N-methylvaline]-4-cyclosporin |
| 490 | O | 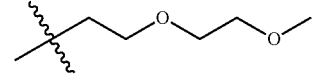 [SMILES: *CCOCCOC] | [(R)-2-(2-Methoxyethoxy)ethoxy-Sar]-3-[N-methylvaline]-4-cyclosporin |
| 491 | O | 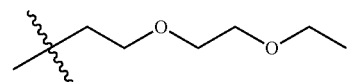 [SMILES: *CCOCCOCC] | [(R)-2-(2-Ethoxyethoxy)ethoxy-Sar]-3-[N-methylvaline]-4-cyclosporin |
| 492 | O | 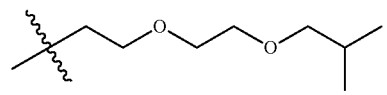 [SMILES: *CCOCCOCC(C)C] | [(R)-2-(2-iso-Butoxyethoxy)ethoxy-Sar]-3-[N-methylvaline]-4-cyclosporin |
| 493 | O | 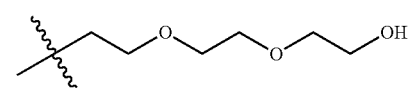 [SMILES: *CCOCCOCCO] | [(R)-2-[2-(2-Hydroxyethoxy)ethoxy]ethoxy-Sar]-3-[N-methylvaline]-4-cyclosporin |
| 494 | O | 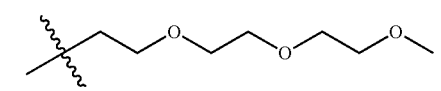 [SMILES: *CCOCCOCCOC] | [(R)-2-[2-(2-Methoxyethoxy)ethoxy]ethoxy-Sar]-3-[N-methylvaline]-4-cyclosporin |
| 495 | O | 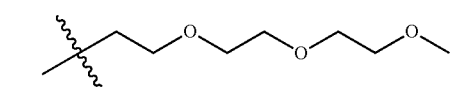 [SMILES: *CCOCCOCCOC] | [(R)-2-[2-(2-Ethoxyethoxy)ethoxy]ethoxy-Sar]-3-[N-methylvaline]-4-cyclosporin |
| 496 | O | 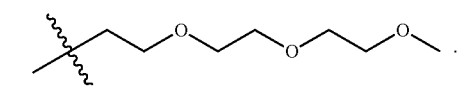 [SMILES: *CCOCCOCCOC] | [(R)-2-[2-(2-iso-Butoxyethoxy)ethoxy]ethoxy-Sar]-3-[N-methylvaline]-4-cyclosporin |

Example 497

Testing HCV Activity of Cyclosporin Derivatives

The anti-HCV activity of cyclosporine derivatives were evaluated in the HCV subgenomic replicon assay. The assay use the cell line ET (luc-ubi-neo/ET), which is a Huh7 human hepatoma cell line harboring an HCV replicon with a stable luciferase (Luc) reporter. HCV RNA replication was assessed by quantifying HCV replicon-derived luciferase activity. The antiviral activity of cyclosporine analogs were evaluated after drug treatment, the EC 50 and EC 90 were determined in subsequent assessments by using the luciferase end point (Krieger, N. et al., 2001, *J. Virol.* 75:4614-4624; Pietschmann, T. et al., 2002, *J. Virol.* 76:4008-4021; each of which is incorporated herein by reference).

The results of certain compounds are as follows:

| Compound | Antiviral activity IC50 (µM) |
|---|---|
| Cyclosporin A | 0.41 |
| [N-Methylvaline]-4-cyclosporin (SDZ-220-384) | 0.17 |
| [N-Methylisoleucine]-4-cyclosporin (SDZ-NIM-811) | 0.15 |
| [(R)-2-(N,N-Diethylamino)ethylthio-Sar]-3-[N-methylvaline]-4-cyclosporin (Example 1) | 0.05 |
| [(S)-2-(N,N-Diethylamino)ethylthio-Sar]-3-[N-methylvaline]-4-cyclosporin | 3.66 |
| [(R)-2-(N,N-Diethylamino)ethylthio-Sar]-3-[N-methylisoleucine]-4-cyclosporin (Example 4) | 0.04 |

| Compound | Antiviral activity IC50 (μM) |
|---|---|
| [(S)-2-(N,N-Diethylamino)ethylthio-Sar]-3-[N-methylisoleucine]-4-cyclosporin | 1.87 |
| [(R)-3-(N-Morpholino)propylthio-Sar]-3-[N-methylisoleucine]-4-cyclosporin (Example 6) | 0.05 |

The invention claimed is:

1. A compound of formula (Ia):

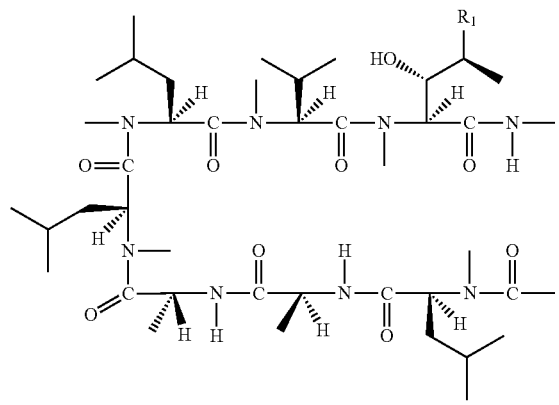

(Ia)

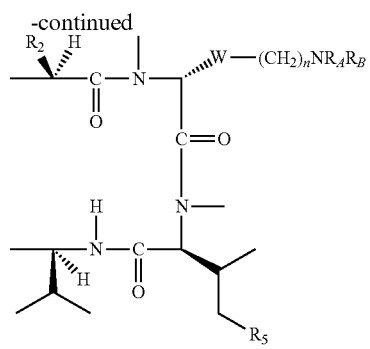

or pharmaceutically acceptable salt thereof, wherein the symbols have the following meanings and are, for each occurrence, independently selected:

$R_1$ is n-butyl or (E)-but-2-enyl;
$R_2$ is ethyl, 1-hydroxyethyl, isobutyl or n-butyl;
W is O or S;
n is an integer of 3, 4, 5 or 6;
$R_5$ is H or methyl;
each occurrence of $R_A$ and $R_B$ is independently hydrogen or $(C_1-C_4)$alkyl, optionally substituted by one or more groups $R_D$ which may be the same or different, in which each occurrence of $R_D$ is independently halogen, hydroxy, $O(C_1-C_4)$alkyl, $C(=O)(C_1-C_4)$alkyl, $C(=O)O(C_1-C_4)$alkyl; or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from $(C_1-C_4)$alkyl, phenyl and benzyl.

2. The compound of claim 1, having the following chemical structure:

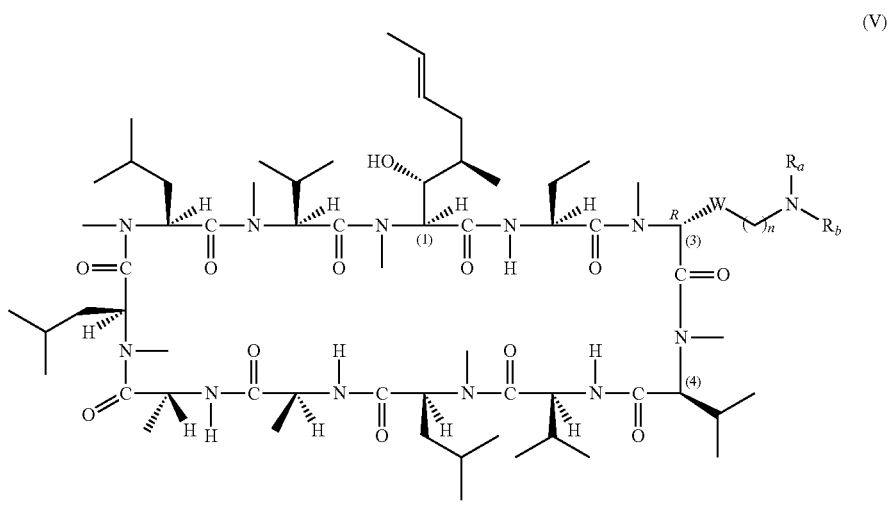

(V)

wherein W is S or O;
n is 3, 4, 5, or 6;
R$_a$ is H, methyl, ethyl, n-propyl, i-propyl, n-butyl, i-butyl, t-butyl, CH$_2$CMe$_3$, phenyl, or CH$_2$-phenyl; and
R$_b$ is H, n-propyl, n-butyl, i-butyl, t-butyl, CH$_2$CMe$_3$, phenyl, or CH$_2$-phenyl;

or is in which R$_c$ is H, methyl, ethyl, n-propyl, i-propyl, n-butyl, i-butyl, t-butyl, CH$_2$CMe$_3$, phenyl, or CH$_2$-phenyl.

3. The compound of claim 1, having the following chemical structure:

or is in which R$_c$ is H, methyl, ethyl, n-propyl, i-propyl, n-butyl, i-butyl, t-butyl, CH$_2$CMe$_3$, phenyl, or CH$_2$-phenyl.

4. The compound of claim 1, selected from the group consisting of:
[(R)-2-(N,N-Diethylamino)ethylthio-Sar]-3-[N-methylvaline]-4-cyclosporine;
[(R)-3-(N,N-Diethylamino)propylthio-Sar]-3-[N-methylvaline]-4-cyclosporine;
[(R)-3-(N-Morpholino)propylthio-Sar]-3-[N-methylvaline]-4-cyclosporin;
[(R)-2-(N,N-Diethylamino)ethylthio-Sar]-3-[N-methylisoleucine]-4-cyclosporin;
[(R)-3-(N,N-Diethylamino)propylthio-Sar]-3-[N-methylisoleucine]-4-cyclosporin;

(VII)

wherein W is S or O;
n is 3, 4, 5, or 6;
R$_a$ is H, methyl, ethyl, n-propyl, i-propyl, n-butyl, i-butyl, t-butyl, CH$_2$CMe$_3$, phenyl, or CH$_2$-phenyl; and
R$_b$ is H, n-propyl, i-propyl, n-butyl, i-butyl, t-butyl, CH$_2$CMe$_3$, phenyl, or CH$_2$-phenyl;

[(R)-3-(N-Morpholino)propylthio-Sar]-3-[N-methylisoleucine]-4-cyclosporin;
[(R)-2-(N-Pyrrolidinyl)ethylthio-Sar]-3-[N-methylisoleucine]-4-cyclosporin;
[(R)-2-(N-1H-Imidazolyl)ethylthio-Sar]-3-[N-methylisoleucine]-4-cyclosporin;

[(R)-2-(N-Piperidinyl)ethylthio-Sar]-3-[N-methylisoleucine]-4-cyclosporin;
[(R)-2-(N-Morpholino)ethylthio-Sar]-3-[N-methylisoleucine]-4-cyclosporin;
[(R)-2-(N-Thiomorpholino)ethylthio-Sar]-3-[N-methylisoleucine]-4-cyclosporin;
[(R)-2-(Piperazinyl)ethylthio-Sar]-3-[N-methylisoleucine]-4-cyclosporin;
[(R)-2-(N-4-Methylpiperazinyl)ethylthio-Sar]-3-[N-methylisoleucine]-4-cyclosporin;
[(R)-2-(N-4-Ethylpiperazinyl)ethylthio-Sar]-3-[N-methylisoleucine]-4-cyclosporin;
[(R)-2-(N-4-n-Propylpiperazinyl)ethylthio-Sar]-3-[N-methylisoleucine]-4-cyclosporin;
[(R)-2-(N-4-iso-Propylpiperazinyl)ethylthio-Sar]-3-[N-methylisoleucine]-4-cyclosporin;
[(R)-2-(N-Pyrrolidinyl)ethoxy-Sar]-3-[N-methylisoleucine]-4-cyclosporin;
[(R)-2-(N-1H-Imidazolyl)ethoxy-Sar]-3-[N-methylisoleucine]-4-cyclosporin;
[(R)-2-(N-Piperidinyl)ethoxy-Sar]-3-[N-methylisoleucine]-4-cyclosporin;
[(R)-2-(N-Morpholino)ethoxy-Sar]-3-[N-methylisoleucine]-4-cyclosporin;
[(R)-2-(N-Thiomorpholino)ethoxy-Sar]-3-[N-methylisoleucine]-4-cyclosporin;
[(R)-2-(Piperazinyl)ethoxy-Sar]-3-[N-methylisoleucine]-4-cyclosporin;
[(R)-2-(N-4-Methylpiperazinyl)ethoxy-Sar]-3-[N-methylisoleucine]-4-cyclosporin;
[(R)-2-(N-4-Ethylpiperazinyl)ethoxy-Sar]-3-[N-methylisoleucine]-4-cyclosporin;
[(R)-2-(N-4-n-Propylpiperazinyl)ethoxy-Sar]-3-[N-methylisoleucine]-4-cyclosporin;
[(R)-2-(N-4-iso-Propylpiperazinyl)ethoxy-Sar]-3-[N-methylisoleucine]-4-cyclosporin;
[(R)-2-(N,N-Di-n-propylamino)ethylthio-Sar]-3-[N-methylisoleucine]-4-cyclosporin;
[(R)-2-(N-n-Propylamino)ethylthio-Sar]-3-[N-methylisoleucine]-4-cyclosporin;
[(R)-2-(N-n-Propyl-N-methylamino)ethylthio-Sar]-3-[N-methylisoleucine]-4-cyclosporin;
[(R)-2-(N-n-Propyl-N-ethylamino)ethylthio-Sar]-3-[N-methylisoleucine]-4-cyclosporin;
[(R)-2-(N,N-Di-iso-propylamino)ethylthio-Sar]-3-[N-methylisoleucine]-4-cyclosporin;
[(R)-2-(N-iso-Propylamino)ethylthio-Sar]-3-[N-methylisoleucine]-4-cyclosporin;
[(R)-2-(N-iso-Propyl-N-methylamino)ethylthio-Sar]-3-[N-methylisoleucine]-4-cyclosporin;
[(R)-2-(N-iso-Propyl-N-ethylamino)ethylthio-Sar]-3-[N-methylisoleucine]-4-cyclosporin;
[(R)-2-(N-iso-Butylamino)ethylthio-Sar]-3-[N-methylisoleucine]-4-cyclosporin;
[(R)-2-(N-iso-Butyl-N-methylamino)ethylthio-Sar]-3-[N-methylisoleucine]-4-cyclosporin;
[(R)-2-(N-iso-Butyl-N-ethylamino)ethylthio-Sar]-3-[N-methylisoleucine]-4-cyclosporin;
[(R)-2-(N-(2',2'-dimethyl)propylamino)ethylthio-Sar]-3-[N-methylisoleucine]-4-cyclosporin;
[(R)-2-(N-(2',2'-dimethyl)propyl-N-methylamino)ethylthio-Sar]-3-[N-methylisoleucine]-4-cyclosporin;
[(R)-2-(N-(2',2'-dimethyl)propyl-N-ethylamino)ethylthio-Sar]-3-[N-methylisoleucine]-4-cyclosporin;
[(R)-2-(N,N-Diethylamino)ethoxy-Sar]-3-[N-methylisoleucine]-4-cyclosporin;
[(R)-2-(N,N-Di-n-proylamino)ethoxy-Sar]-3-[N-methylisoleucine]-4-cyclosporin;
[(R)-2-(N-n-Propylamino)ethoxy-Sar]-3-[N-methylisoleucine]-4-cyclosporin;
[(R)-2-(N-n-Propyl-N-methylamino)ethoxy-Sar]-3-[N-methylisoleucine]-4-cyclosporin;
[(R)-2-(N-n-Propyl-N-ethylamino)ethoxy-Sar]-3-[N-methylisoleucine]-4-cyclosporin;
[(R)-2-(N,N-Di-iso-propylamino)ethoxy-Sar]-3-[N-methylisoleucine]-4-cyclosporin;
[(R)-2-(N-iso-Propylamino)ethoxy-Sar]-3-[N-methylisoleucine]-4-cyclosporin;
[(R)-2-(N-iso-Propyl-N-methylamino)ethoxy-Sar]-3-[N-methylisoleucine]-4-cyclosporin;
[(R)-2-(N-iso-Propyl-N-ethylamino)ethoxy-Sar]-3-[N-methylisoleucine]-4-cyclosporin;
[(R)-2-(N-iso-Butylamino)ethoxy-Sar]-3-[N-methylisoleucine]-4-cyclosporin;
[(R)-2-(N-iso-Butyl-N-methylamino)ethoxy-Sar]-3-[N-methylisoleucine]-4-cyclosporin;
[(R)-2-(N-iso-Butyl-N-ethylamino)ethoxy-Sar]-3-[N-methylisoleucine]-4-cyclosporin;
[(R)-2-(N-(2',2'-dimethyl)propylamino)ethoxy-Sar]-3-[N-methylisoleucine]-4-cyclosporin;
[(R)-2-(N-(2',2'-dimethyl)propyl-N-methylamino)ethoxy-Sar]-3-[N-methylisoleucine]-4-cyclosporin;
[(R)-2-(N-(2',2'-dimethyl)propyl-N-ethylamino)ethoxy-Sar]-3-[N-methylisoleucine]-4-cyclosporin;
[(R)-3-(N-Azetidinyl)propylthio-Sar]-3-[N-methylisoleucine]-4-cyclosporin;
[(R)-3-(N-Pyrrolidinyl)propylthio-Sar]-3-[N-methylisoleucine]-4-cyclosporin;
[(R)-3-(N-1H-Imidazolyl)propylthio-Sar]-3-[N-methylisoleucine]-4-cyclosporin;
[(R)-3-(N-Piperidinyl)propylthio-Sar]-3-[N-methylisoleucine]-4-cyclosporin;
[(R)-3-(N-Thiomorpholino)propylthio-Sar]-3-[N-methylisoleucine]-4-cyclosporin;
[(R)-3-(Piperazinyl)propylthio-Sar]-3-[N-methylisoleucine]-4-cyclosporin;
[(R)-3-(N-4-Methylpiperazinyl)propylthio-Sar]-3-[N-methylisoleucine]-4-cyclosporin;
[(R)-3-(N-4-Ethylpiperazinyl)propylthio-Sar]-3-[N-methylisoleucine]-4-cyclosporin;
[(R)-3-(N-4-n-Propylpiperazinyl)propylthio-Sar]-3-[N-methylisoleucine]-4-cyclosporin;
[(R)-3-(N-4-iso-Propylpiperazinyl)propylthio-Sar]-3-[N-methylisoleucine]-4-cyclosporin;
[(R)-3-(N-Azetidinyl)propoxy-Sar]-3-[N-methylisoleucine]-4-cyclosporin;
[(R)-3-(N-Pyrrolidinyl)propoxy-Sar]-3-[N-methylisoleucine]-4-cyclosporin;
[(R)-3-(N-1H-Imidazolyl)propoxy-Sar]-3-[N-methylisoleucine]-4-cyclosporin;
[(R)-3-(N-Piperidinyl)propoxy-Sar]-3-[N-methylisoleucine]-4-cyclosporin;
[(R)-3-(N-Morpholino)propoxy-Sar]-3-[N-methylisoleucine]-4-cyclosporin;
[(R)-3-(N-Thiomorpholino)propoxy-Sar]-3-[N-methylisoleucine]-4-cyclosporin;
[(R)-3-(Piperazinyl)propoxy-Sar]-3-[N-methylisoleucine]-4-cyclosporin;
[(R)-3-(N-4-Methylpiperazinyl)propoxy-Sar]-3-[N-methylisoleucine]-4-cyclosporin;
[(R)-3-(N-4-Ethylpiperazinyl)propoxy-Sar]-3-[N-methylisoleucine]-4-cyclosporin;

[(R)-3-(N-4-n-Propylpiperazinyl)propoxy-Sar]-3-[N-methylisoleucine]-4-cyclosporin;
[(R)-3-(N-4-iso-Propylpiperazinyl)propoxy-Sar]-3-[N-methylisoleucine]-4-cyclosporin;
[(R)-3-(N,N-Dimethylamino)propylthio-Sar]-3-[N-methylisoleucine]-4-cyclosporin;
[(R)-3-(N,N-Di-n-proylamino)propylthio-Sar]-3-[N-methylisoleucine]-4-cyclosporin;
[(R)-3-(N-n-Propylamino)propylthio-Sar]-3-[N-methylisoleucine]-4-cyclosporin;
[(R)-3-(N-n-Propyl-N-methylamino)propylthio-Sar]-3-[N-methylisoleucine]-4-cyclosporin;
[(R)-3-(N-n-Propyl-N-ethylamino)propylthio-Sar]-3-[N-methylisoleucine]-4-cyclosporin;
[(R)-3-(N,N-Di-iso-propylamino)propylthio-Sar]-3-[N-methylisoleucine]-4-cyclosporin;
[(R)-3-(N-iso-Propylamino)propylthio-Sar]-3-[N-methylisoleucine]-4-cyclosporin;
[(R)-3-(N-iso-Propyl-N-methylamino)propylthio-Sar]-3-[N-methylisoleucine]-4-cyclosporin;
[(R)-3-(N-iso-Propyl-N-ethylamino)propylthio-Sar]-3-[N-methylisoleucine]-4-cyclosporin;
[(R)-3-(N-iso-Butylamino)propylthio-Sar]-3-[N-methylisoleucine]-4-cyclosporin;
[(R)-3-(N-iso-Butyl-N-methylamino)propylthio-Sar]-3-[N-methylisoleucine]-4-cyclosporin;
[(R)-3-(N-iso-Butyl-N-ethylamino)propylthio-Sar]-3-[N-methylisoleucine]-4-cyclosporin;
[(R)-3-(N-(2',2'-dimethyl)propylamino)propylthio-Sar]-3-[N-methylisoleucine]-4-cyclosporin;
[(R)-3-(N-(2',2'-dimethyl)propyl-N-methylamino)propylthio-Sar]-3-[N-methylisoleucine]-4-cyclosporin;
[(R)-3-(N-(2',2'-dimethyl)propyl-N-ethylamino)propylthio-Sar]-3-[N-methylisoleucine]-4-cyclosporin;
[(R)-3-(N,N-Dimethylamino)propoxy-Sar]-3-[N-methylisoleucine]-4-cyclosporin;
[(R)-3-(N,N-Diethylamino)propoxy-Sar]-3-[N-methylisoleucine]-4-cyclosporin;
[(R)-3-(N,N-Di-n-proylamino)propoxy-Sar]-3-[N-methylisoleucine]-4-cyclosporin;
[(R)-3-(N-n-Propylamino)propoxy-Sar]-3-[N-methylisoleucine]-4-cyclosporin;
[(R)-3-(N-n-Propyl-N-methylamino)propoxy-Sar]-3-[N-methylisoleucine]-4-cyclosporin;
[(R)-3-(N-n-Propyl-N-ethylamino)propoxy-Sar]-3-[N-methylisoleucine]-4-cyclosporin;
[(R)-3-(N,N-Di-iso-propylamino)propoxy-Sar]-3-[N-methylisoleucine]-4-cyclosporin;
[(R)-3-(N-iso-Propylamino)propoxy-Sar]-3-[N-methylisoleucine]-4-cyclosporin;
[(R)-3-(N-iso-Propyl-N-methylamino)propoxy-Sar]-3-[N-methylisoleucine]-4-cyclosporin;
[(R)-3-(N-iso-Propyl-N-ethylamino)propoxy-Sar]-3-[N-methylisoleucine]-4-cyclosporin;
[(R)-3-(N-iso-Butylamino)propoxy-Sar]-3-[N-methylisoleucine]-4-cyclosporin;
[(R)-3-(N-iso-Butyl-N-methylamino)propoxy-Sar]-3-[N-methylisoleucine]-4-cyclosporin;
[(R)-3-(N-iso-Butyl-N-ethylamino)propoxy-Sar]-3-[N-methylisoleucine]-4-cyclosporin;
[(R)-3-(N-(2',2'-dimethyl)propylamino)propoxy-Sar]-3-[N-methylisoleucine]-4-cyclosporin;
[(R)-3-(N-(2',2'-dimethyl)propyl-N-methylamino)propoxy-Sar]-3-[N-methylisoleucine]-4-cyclosporin;
[(R)-3-(N-(2',2'-dimethyl)propyl-N-ethylamino)propoxy-Sar]-3-[N-methylisoleucine]-4-cyclosporin;
[(R)-4-(N-Azetidinyl)Butylthio-Sar]-3-[N-methylisoleucine]-4-cyclosporin;
[(R)-4-(N-Pyrrolidinyl)Butylthio-Sar]-3-[N-methylisoleucine]-4-cyclosporin;
[(R)-4-(N-1H-Imidazolyl)Butylthio-Sar]-3-[N-methylisoleucine]-4-cyclosporin;
[(R)-4-(N-Piperidinyl)Butylthio-Sar]-3-[N-methylisoleucine]-4-cyclosporin;
[(R)-4-(N-Morpholino)Butylthio-Sar]-3-[N-methylisoleucine]-4-cyclosporin;
[(R)-4-(N-Thiomorpholino)Butylthio-Sar]-3-[N-methylisoleucine]-4-cyclosporin;
[(R)-4-(Piperazinyl)Butylthio-Sar]-3-[N-methylisoleucine]-4-cyclosporin;
[(R)-4-(N-4-Methylpiperazinyl)Butylthio-Sar]-3-[N-methylisoleucine]-4-cyclosporin;
[(R)-4-(N-4-Ethylpiperazinyl)Butylthio-Sar]-3-[N-methylisoleucine]-4-cyclosporin;
[(R)-4-(N-4-n-Propylpiperazinyl)Butylthio-Sar]-3-[N-methylisoleucine]-4-cyclosporin;
[(R)-4-(N-4-iso-Propylpiperazinyl)Butylthio-Sar]-3-[N-methylisoleucine]-4-cyclosporin;
[(R)-4-(N-Azetidinyl)Butoxy-Sar]-3-[N-methylisoleucine]-4-cyclosporin;
[(R)-4-(N-Pyrrolidinyl)Butoxy-Sar]-3-[N-methylisoleucine]-4-cyclosporin;
[(R)-4-(N-1H-Imidazolyl)Butoxy-Sar]-3-[N-methylisoleucine]-4-cyclosporin;
[(R)-4-(N-Piperidinyl)Butoxy-Sar]-3-[N-methylisoleucine]-4-cyclosporin;
[(R)-4-(N-Morpholino)Butoxy-Sar]-3-[N-methylisoleucine]-4-cyclosporin;
[(R)-4-(N-Thiomorpholino)Butoxy-Sar]-3-[N-methylisoleucine]-4-cyclosporin;
[(R)-4-(Piperazinyl)Butoxy-Sar]-3-[N-methylisoleucine]-4-cyclosporin;
[(R)-4-(N-4-Methylpiperazinyl)Butoxy-Sar]-3-[N-methylisoleucine]-4-cyclosporin;
[(R)-4-(N-4-Ethylpiperazinyl)Butoxy-Sar]-3-[N-methylisoleucine]-4-cyclosporin;
[(R)-4-(N-4-n-Propylpiperazinyl)Butoxy-Sar]-3-[N-methylisoleucine]-4-cyclosporin;
[(R)-4-(N-4-iso-Propylpiperazinyl)Butoxy-Sar]-3-[N-methylisoleucine]-4-cyclosporin;
[(R)-4-(N,N-Dimethylamino)butylthio-Sar]-3-[N-methylisoleucine]-4-cyclosporin;
[(R)-4-(N,N-Diethylamino)butylthio-Sar]-3-[N-methylisoleucine]-4-cyclosporin;
[(R)-4-(N,N-Di-n-proylamino)butylthio-Sar]-3-[N-methylisoleucine]-4-cyclosporin;
[(R)-4-(N-n-Propylamino)butylthio-Sar]-3-[N-methylisoleucine]-4-cyclosporin;
[(R)-4-(N-n-Propyl-N-methylamino)butylthio-Sar]-3-[N-methylisoleucine]-4-cyclosporin;
[(R)-4-(N-n-Propyl-N-ethylamino)butylthio-Sar]-3-[N-methylisoleucine]-4-cyclosporin;
[(R)-4-(N,N-Di-iso-propylamino)butylthio-Sar]-3-[N-methylisoleucine]-4-cyclosporin;
[(R)-4-(N-iso-Propylamino)butylthio-Sar]-3-[N-methylisoleucine]-4-cyclosporin;
[(R)-4-(N-iso-Propyl-N-methylamino)butylthio-Sar]-3-[N-methylisoleucine]-4-cyclosporin;
[(R)-4-(N-iso-Propyl-N-ethylamino)butylthio-Sar]-3-[N-methylisoleucine]-4-cyclosporin;
[(R)-4-(N-iso-Butylamino)butylthio-Sar]-3-[N-methylisoleucine]-4-cyclosporin;

[(R)-4-(N-iso-Butyl-N-methylamino)butylthio-Sar]-3-[N-methylisoleucine]-4-cyclosporin;
[(R)-4-(N-iso-Butyl-N-ethylamino)butylthio-Sar]-3-[N-methylisoleucine]-4-cyclosporin;
[(R)-4-(N-(2',2'-dimethyl)propylamino)butylthio-Sar]-3-[N-methylisoleucine]-4-cyclosporin;
[(R)-4-(N-(2',2'-dimethyl)propyl-N-methylamino)butylthio-Sar]-3-[N-methylisoleucine]-4-cyclosporin;
[(R)-4-(N-(2',2'-dimethyl)propyl-N-ethylamino)butylthio-Sar]-3-[N-methylisoleucine]-4-cyclosporin;
[(R)-4-(N,N-Dimethylamino)butoxy-Sar]-3-[N-methylisoleucine]-4-cyclosporin;
[(R)-4-(N,N-Diethylamino)butoxy-Sar]-3-[N-methylisoleucine]-4-cyclosporin;
[(R)-4-(N,N-Di-n-proylamino)butoxy-Sar]-3-[N-methylisoleucine]-4-cyclosporin;
[(R)-4-(N-n-Propylamino)butoxy-Sar]-3-[N-methylisoleucine]-4-cyclosporin;
[(R)-4-(N-n-Propyl-N-methylamino)butoxy-Sar]-3-[N-methylisoleucine]-4-cyclosporin;
[(R)-4-(N-n-Propyl-N-ethylamino)butoxy-Sar]-3-[N-methylisoleucine]-4-cyclosporin;
[(R)-4-(N,N-Di-iso-propylamino)butoxy-Sar]-3-[N-methylisoleucine]-4-cyclosporin;
[(R)-4-(N-iso-Propylamino)butoxy-Sar]-3-[N-methylisoleucine]-4-cyclosporin;
[(R)-4-(N-iso-Propyl-N-methylamino)butoxy-Sar]-3-[N-methylisoleucine]-4-cyclosporin;
[(R)-4-(N-iso-Propyl-N-ethylamino)butoxy-Sar]-3-[N-methylisoleucine]-4-cyclosporin;
[(R)-4-(N-iso-Butylamino)butoxy-Sar]-3-[N-methylisoleucine]-4-cyclosporin;
[(R)-4-(N-iso-Butyl-N-methylamino)butoxy-Sar]-3-[N-methylisoleucine]-4-cyclosporin;
[(R)-4-(N-iso-Butyl-N-ethylamino)butoxy-Sar]-3-[N-methylisoleucine]-4-cyclosporin;
[(R)-4-(N-(2',2'-dimethyl)propylamino)butoxy-Sar]-3-[N-methylisoleucine]-4-cyclosporin;
[(R)-4-(N-(2',2'-dimethyl)propyl-N-methylamino)butoxy-Sar]-3-[N-methylisoleucine]-4-cyclosporin;
[(R)-4-(N-(2',2'-dimethyl)propyl-N-ethylamino)butoxy-Sar]-3-[N-methylisoleucine]-4-cyclosporin;
[(R)-5-(N-Azetidinyl)pentylthio-Sar]-3-[N-methylisoleucine]-4-cyclosporin;
[(R)-5-(N-Pyrrolidinyl)pentylthio-Sar]-3-[N-methylisoleucine]-4-cyclosporin;
[(R)-5-(N-1H-Imidazolyl)pentylthio-Sar]-3-[N-methylisoleucine]-4-cyclosporin;
[(R)-5-(N-Piperidinyl)pentylthio-Sar]-3-[N-methylisoleucine]-4-cyclosporin;
[(R)-5-(N-Morpholino)pentylthio-Sar]-3-[N-methylisoleucine]-4-cyclosporin;
[(R)-5-(N-Thiomorpholino)pentylthio-Sar]-3-[N-methylisoleucine]-4-cyclosporin;
[(R)-5-(Piperazinyl)pentylthio-Sar]-3-[N-methylisoleucine]-4-cyclosporin;
[(R)-5-(N-4-Methylpiperazinyl)pentylthio-Sar]-3-[N-methylisoleucine]-4-cyclosporin;
[(R)-5-(N-4-Ethylpiperazinyl)pentylthio-Sar]-3-[N-methylisoleucine]-4-cyclosporin;
[(R)-5-(N-4-n-Propylpiperazinyl)pentylthio-Sar]-3-[N-methylisoleucine]-4-cyclosporin;
[(R)-5-(N-4-iso-Propylpiperazinyl)pentylthio-Sar]-3-[N-methylisoleucine]-4-cyclosporin;
[(R)-5-(N-Azetidinyl)pentyloxy-Sar]-3-[N-methylisoleucine]-4-cyclosporin;
[(R)-5-(N-Pyrrolidinyl)pentyloxy-Sar]-3-[N-methylisoleucine]-4-cyclosporin;
[(R)-5-(N-1H-Imidazolyl)pentyloxy-Sar]-3-[N-methylisoleucine]-4-cyclosporin;
[(R)-5-(N-Piperidinyl)pentyloxy-Sar]-3-[N-methylisoleucine]-4-cyclosporin;
[(R)-5-(N-Morpholino)pentyloxy-Sar]-3-[N-methylisoleucine]-4-cyclosporin;
[(R)-5-(N-Thiomorpholino)pentyloxy-Sar]-3-[N-methylisoleucine]-4-cyclosporin;
[(R)-5-(Piperazinyl)pentyloxy-Sar]-3-[N-methylisoleucine]-4-cyclosporin;
[(R)-5-(N-4-Methylpiperazinyl)pentyloxy-Sar]-3-[N-methylisoleucine]-4-cyclosporin;
[(R)-5-(N-4-Ethylpiperazinyl)pentyloxy-Sar]-3-[N-methylisoleucine]-4-cyclosporin;
[(R)-5-(N-4-n-Propylpiperazinyl)pentyloxy-Sar]-3-[N-methylisoleucine]-4-cyclosporin;
[(R)-5-(N-4-iso-Propylpiperazinyl)pentyloxy-Sar]-3-[N-methylisoleucine]-4-cyclosporin;
[(R)-5-(N,N-Dimethylamino)pentylthio-Sar]-3-[N-methylisoleucine]-4-cyclosporin;
[(R)-5-(N,N-Diethylamino)pentylthio-Sar]-3-[N-methylisoleucine]-4-cyclosporin;
[(R)-5-(N,N-Di-n-proylamino)pentylthio-Sar]-3-[N-methylisoleucine]-4-cyclosporin;
[(R)-5-(N-n-Propylamino)pentylthio-Sar]-3-[N-methylisoleucine]-4-cyclosporin;
[(R)-5-(N-n-Propyl-N-methylamino)pentylthio-Sar]-3-[N-methylisoleucine]-4-cyclosporin;
[(R)-5-(N-n-Propyl-N-ethylamino)pentylthio-Sar]-3-[N-methylisoleucine]-4-cyclosporin;
[(R)-5-(N,N-Di-iso-propylamino)pentylthio-Sar]-3-[N-methylisoleucine]-4-cyclosporin;
[(R)-5-(N-iso-Propylamino)pentylthio-Sar]-3-[N-methylisoleucine]-4-cyclosporin;
[(R)-5-(N-iso-Propyl-N-methylamino)pentylthio-Sar]-3-[N-methylisoleucine]-4-cyclosporin;
[(R)-5-(N-iso-Propyl-N-ethylamino)pentylthio-Sar]-3-[N-methylisoleucine]-4-cyclosporin;
[(R)-5-(N-iso-Butylamino)pentylthio-Sar]-3-[N-methylisoleucine]-4-cyclosporin;
[(R)-5-(N-iso-Butyl-N-methylamino)pentylthio-Sar]-3-[N-methylisoleucine]-4-cyclosporin;
[(R)-5-(N-iso-Butyl-N-ethylamino)pentylthio-Sar]-3-[N-methylisoleucine]-4-cyclosporin;
[(R)-5-(N-(2',2'-dimethyl)propylamino)pentylthio-Sar]-3-[N-methylisoleucine]-4-cyclosporin;
[(R)-5-(N-(2',2'-dimethyl)propyl-N-methylamino)pentylthio-Sar]-3-[N-methylisoleucine]-4-cyclosporin;
[(R)-5-(N-(2',2'-dimethyl)propyl-N-ethylamino)pentylthio-Sar]-3-[N-methylisoleucine]-4-cyclosporin;
[(R)-5-(N,N-Dimethylamino)pentyloxy-Sar]-3-[N-methylisoleucine]-4-cyclosporin;
[(R)-5-(N,N-Diethylamino)pentyloxy-Sar]-3-[N-methylisoleucine]-4-cyclosporin;
[(R)-5-(N,N-Di-n-proylamino)pentyloxy-Sar]-3-[N-methylisoleucine]-4-cyclosporin;
[(R)-5-(N-n-Propylamino)pentyloxy-Sar]-3-[N-methylisoleucine]-4-cyclosporin;
[(R)-5-(N-n-Propyl-N-methylamino)pentyloxy-Sar]-3-[N-methylisoleucine]-4-cyclosporin;
[(R)-5-(N-n-Propyl-N-ethylamino)pentyloxy-Sar]-3-[N-methylisoleucine]-4-cyclosporin;
[(R)-5-(N,N-Di-iso-propylamino)pentyloxy-Sar]-3-[N-methylisoleucine]-4-cyclosporin;

[(R)-5-(N-iso-Propylamino)pentyloxy-Sar]-3-[N-methylisoleucine]-4-cyclosporin;
[(R)-5-(N-iso-Propyl-N-methylamino)pentyloxy-Sar]-3-[N-methylisoleucine]-4-cyclosporin;
[(R)-5-(N-iso-Propyl-N-ethylamino)pentyloxy-Sar]-3-[N-methylisoleucine]-4-cyclosporin;
[(R)-5-(N-iso-Butylamino)pentyloxy-Sar]-3-[N-methylisoleucine]-4-cyclosporin;
[(R)-5-(N-iso-Butyl-N-methylamino)pentyloxy-Sar]-3-[N-methylisoleucine]-4-cyclosporin;
[(R)-5-(N-iso-Butyl-N-ethylamino)pentyloxy-Sar]-3-[N-methylisoleucine]-4-cyclosporin;
[(R)-5-(N-(2',2'-dimethyl)propylamino)pentyloxy-Sar]-3-[N-methylisoleucine]-4-cyclosporin;
[(R)-5-(N-(2',2'-dimethyl)propyl-N-methylamino)pentyloxy-Sar]-3-[N-methylisoleucine]-4-cyclosporin;
[(R)-5-(N-(2',2'-dimethyl)propyl-N-ethylamino)pentyloxy-Sar]-3-[N-methylisoleucine]-4-cyclosporin;
[(R)-2-(N-Pyrrolidinyl)ethylthio-Sar]-3-[N-methylvaline]-4-cyclosporin;
[(R)-2-(N-1H-Imidazolyl)ethylthio-Sar]-3-[N-methylvaline]-4-cyclosporin;
[(R)-2-(N-Piperidinyl)ethylthio-Sar]-3-[N-methylvaline]-4-cyclosporin;
[(R)-2-(N-Morpholino)ethylthio-Sar]-3-[N-methylvaline]-4-cyclosporin;
[(R)-2-(N-Thiomorpholino)ethylthio-Sar]-3-[N-methylvaline]-4-cyclosporin;
[(R)-2-(Piperazinyl)ethylthio-Sar]-3-[N-methylvaline]-4-cyclosporin;
[(R)-2-(N-4-Methylpiperazinyl)ethylthio-Sar]-3-[N-methylvaline]-4-cyclosporin;
[(R)-2-(N-4-Ethylpiperazinyl)ethylthio-Sar]-3-[N-methylvaline]-4-cyclosporin;
[(R)-2-(N-4-n-Propylpiperazinyl)ethylthio-Sar]-3-[N-methylvaline]-4-cyclosporin;
[(R)-2-(N-4-iso-Propylpiperazinyl)ethylthio-Sar]-3-[N-methylvaline]-4-cyclosporin;
[(R)-2-(N-Pyrrolidinyl)ethoxy-Sar]-3-[N-methylvaline]-4-cyclosporin;
[(R)-2-(N-1H-Imidazolyl)ethoxy-Sar]-3-[N-methylvaline]-4-cyclosporin;
[(R)-2-(N-Piperidinyl)ethoxy-Sar]-3-[N-methylvaline]-4-cyclosporin;
[(R)-2-(N-Morpholino)ethoxy-Sar]-3-[N-methylvaline]-4-cyclosporin;
[(R)-2-(N-Thiomorpholino)ethoxy-Sar]-3-[N-methylvaline]-4-cyclosporin;
[(R)-2-(Piperazinyl)ethoxy-Sar]-3-[N-methylvaline]-4-cyclosporin;
[(R)-2-(N-4-Methylpiperazinyl)ethoxy-Sar]-3-[N-methylvaline]-4-cyclosporin;
[(R)-2-(N-4-Ethylpiperazinyl)ethoxy-Sar]-3-[N-methylvaline]-4-cyclosporin;
[(R)-2-(N-4-n-Propylpiperazinyl)ethoxy-Sar]-3-[N-methylvaline]-4-cyclosporin;
[(R)-2-(N-4-iso-Propylpiperazinyl)ethoxy-Sar]-3-[N-methylvaline]-4-cyclosporin;
[(R)-2-(N,N-Di-n-proylamino)ethylthio-Sar]-3-[N-methylvaline]-4-cyclosporin;
[(R)-2-(N-n-Propylamino)ethylthio-Sar]-3-[N-methylvaline]-4-cyclosporin;
[(R)-2-(N-n-Propyl-N-methylamino)ethylthio-Sar]-3-[N-methylvaline]-4-cyclosporin;
[(R)-2-(N-n-Propyl-N-ethylamino)ethylthio-Sar]-3-[N-methylvaline]-4-cyclosporin;
[(R)-2-(N,N-Di-iso-propylamino)ethylthio-Sar]-3-[N-methylvaline]-4-cyclosporin;
[(R)-2-(N-iso-Propylamino)ethylthio-Sar]-3-[N-methylvaline]-4-cyclosporin;
[(R)-2-(N-iso-Propyl-N-methylamino)ethylthio-Sar]-3-[N-methylvaline]-4-cyclosporin;
[(R)-2-(N-iso-Propyl-N-ethylamino)ethylthio-Sar]-3-[N-methylvaline]-4-cyclosporin;
[(R)-2-(N-iso-Butylamino)ethylthio-Sar]-3-[N-methylvaline]-4-cyclosporin;
[(R)-2-(N-iso-Butyl-N-methylamino)ethylthio-Sar]-3-[N-methylvaline]-4-cyclosporin;
[(R)-2-(N-iso-Butyl-N-ethylamino)ethylthio-Sar]-3-[N-methylvaline]-4-cyclosporin;
[(R)-2-(N-(2',2'-dimethyl)propylamino)ethylthio-Sar]-3-[N-methylvaline]-4-cyclosporin;
[(R)-2-(N-(2',2'-dimethyl)propyl-N-methylamino)ethylthio-Sar]-3-[N-methylvaline]-4-cyclosporin;
[(R)-2-(N-(2',2'-dimethyl)propyl-N-ethylamino)ethylthio-Sar]-3-[N-methylvaline]-4-cyclosporin;
[(R)-2-(N,N-Diethylamino)ethoxy-Sar]-3-[N-methylvaline]-4-cyclosporin;
[(R)-2-(N,N-Di-n-proylamino)ethoxy-Sar]-3-[N-methylvaline]-4-cyclosporin;
[(R)-2-(N-n-Propylamino)ethoxy-Sar]-3-[N-methylvaline]-4-cyclosporin;
[(R)-2-(N-n-Propyl-N-methylamino)ethoxy-Sar]-3-[N-methylvaline]-4-cyclosporin;
[(R)-2-(N-n-Propyl-N-ethylamino)ethoxy-Sar]-3-[N-methylvaline]-4-cyclosporin;
[(R)-2-(N,N-Di-iso-propylamino)ethoxy-Sar]-3-[N-methylvaline]-4-cyclosporin;
[(R)-2-(N-iso-Propylamino)ethoxy-Sar]-3-[N-methylvaline]-4-cyclosporin;
[(R)-2-(N-iso-Propyl-N-methylamino)ethoxy-Sar]-3-[N-methylvaline]-4-cyclosporin;
[(R)-2-(N-iso-Propyl-N-ethylamino)ethoxy-Sar]-3-[N-methylvaline]-4-cyclosporin;
[(R)-2-(N-iso-Butylamino)ethoxy-Sar]-3-[N-methylvaline]-4-cyclosporin;
[(R)-2-(N-iso-Butyl-N-methylamino)ethoxy-Sar]-3-[N-methylvaline]-4-cyclosporin;
[(R)-2-(N-iso-Butyl-N-ethylamino)ethoxy-Sar]-3-[N-methylvaline]-4-cyclosporin;
[(R)-2-(N-(2',2'-dimethyl)propylamino)ethoxy-Sar]-3-[N-methylvaline]-4-cyclosporin;
[(R)-2-(N-(2',2'-dimethyl)propyl-N-methylamino)ethoxy-Sar]-3-[N-methylvaline]-4-cyclosporin;
[(R)-2-(N-(2',2'-dimethyl)propyl-N-ethylamino)ethoxy-Sar]-3-[N-methylvaline]-4-cyclosporin;
[(R)-3-(N-Azetidinyl)propylthio-Sar]-3-[N-methylvaline]-4-cyclosporin;
[(R)-3-(N-Pyrrolidinyl)propylthio-Sar]-3-[N-methylvaline]-4-cyclosporin;
[(R)-3-(N-1H-Imidazolyl)propylthio-Sar]-3-[N-methylvaline]-4-cyclosporin;
[(R)-3-(N-Piperidinyl)propylthio-Sar]-3-[N-methylvaline]-4-cyclosporin;
[(R)-3-(N-Thiomorpholino)propylthio-Sar]-3-[N-methylvaline]-4-cyclosporin;
[(R)-3-(Piperazinyl)propylthio-Sar]-3-[N-methylvaline]-4-cyclosporin;
[(R)-3-(N-4-Methylpiperazinyl)propylthio-Sar]-3-[N-methylvaline]-4-cyclosporin;
[(R)-3-(N-4-Ethylpiperazinyl)propylthio-Sar]-3-[N-methylvaline]-4-cyclosporin;

[(R)-3-(N-4-n-Propylpiperazinyl)propylthio-Sar]-3-[N-methylvaline]-4-cyclosporin;
[(R)-3-(N-4-iso-Propylpiperazinyl)propylthio-Sar]-3-[N-methylvaline]-4-cyclosporin;
[(R)-3-(N-Azetidinyl)propoxy-Sar]-3-[N-methylvaline]-4-cyclosporin;
[(R)-3-(N-Pyrrolidinyl)propoxy-Sar]-3-[N-methylvaline]-4-cyclosporin;
[(R)-3-(N-1H-Imidazolyl)propoxy-Sar]-3-[N-methylvaline]-4-cyclosporin;
[(R)-3-(N-Piperidinyl)propoxy-Sar]-3-[N-methylvaline]-4-cyclosporin;
[(R)-3-(N-Morpholino)propoxy-Sar]-3-[N-methylvaline]-4-cyclosporin;
[(R)-3-(N-Thiomorpholino)propoxy-Sar]-3-[N-methylvaline]-4-cyclosporin;
[(R)-3-(Piperazinyl)propoxy-Sar]-3-[N-methylvaline]-4-cyclosporin;
[(R)-3-(N-4-Methylpiperazinyl)propoxy-Sar]-3-[N-methylvaline]-4-cyclosporin;
[(R)-3-(N-4-Ethylpiperazinyl)propoxy-Sar]-3-[N-methylvaline]-4-cyclosporin;
[(R)-3-(N-4-n-Propylpiperazinyl)propoxy-Sar]-3-[N-methylvaline]-4-cyclosporin;
[(R)-3-(N-4-iso-Propylpiperazinyl)propoxy-Sar]-3-[N-methylvaline]-4-cyclosporin;
[(R)-3-(N,N-Dimethylamino)propylthio-Sar]-3-[N-methylvaline]-4-cyclosporin;
[(R)-3-(N,N-Di-n-proylamino)propylthio-Sar]-3-[N-methylvaline]-4-cyclosporin;
[(R)-3-(N-n-Propylamino)propylthio-Sar]-3-[N-methylvaline]-4-cyclosporin;
[(R)-3-(N-n-Propyl-N-methylamino)propylthio-Sar]-3-[N-methylvaline]-4-cyclosporin;
[(R)-3-(N-n-Propyl-N-ethylamino)propylthio-Sar]-3-[N-methylvaline]-4-cyclosporin;
[(R)-3-(N,N-Di-iso-propylamino)propylthio-Sar]-3-[N-methylvaline]-4-cyclosporin;
[(R)-3-(N-iso-Propylamino)propylthio-Sar]-3-[N-methylvaline]-4-cyclosporin;
[(R)-3-(N-iso-Propyl-N-methylamino)propylthio-Sar]-3-[N-methylvaline]-4-cyclosporin;
[(R)-3-(N-iso-Propyl-N-ethylamino)propylthio-Sar]-3-[N-methylvaline]-4-cyclosporin;
[(R)-3-(N-iso-Butylamino)propylthio-Sar]-3-[N-methylvaline]-4-cyclosporin;
[(R)-3-(N-iso-Butyl-N-methylamino)propylthio-Sar]-3-[N-methylvaline]-4-cyclosporin;
[(R)-3-(N-iso-Butyl-N-ethylamino)propylthio-Sar]-3-[N-methylvaline]-4-cyclosporin;
[(R)-3-(N-(2',2'-dimethyl)propylamino)propylthio-Sar]-3-[N-methylvaline]-4-cyclosporin;
[(R)-3-(N-(2',2'-dimethyl)propyl-N-methylamino)propylthio-Sar]-3-[N-methylvaline]-4-cyclosporin;
[(R)-3-(N-(2',2'-dimethyl)propyl-N-ethylamino)propylthio-Sar]-3-[N-methylvaline]-4-cyclosporin;
[(R)-3-(N,N-Dimethylamino)propoxy-Sar]-3-[N-methylvaline]-4-cyclosporin;
[(R)-3-(N,N-Diethylamino)propoxy-Sar]-3-[N-methylvaline]-4-cyclosporin;
[(R)-3-(N,N-Di-n-proylamino)propoxy-Sar]-3-[N-methylvaline]-4-cyclosporin;
[(R)-3-(N-n-Propylamino)propoxy-Sar]-3-[N-methylvaline]-4-cyclosporin;
[(R)-3-(N-n-Propyl-N-methylamino)propoxy-Sar]-3-[N-methylvaline]-4-cyclosporin;
[(R)-3-(N-n-Propyl-N-ethylamino)propoxy-Sar]-3-[N-methylvaline]-4-cyclosporin;
[(R)-3-(N,N-Di-iso-propylamino)propoxy-Sar]-3-[N-methylvaline]-4-cyclosporin;
[(R)-3-(N-iso-Propylamino)propoxy-Sar]-3-[N-methylvaline]-4-cyclosporin;
[(R)-3-(N-iso-Propyl-N-methylamino)propoxy-Sar]-3-[N-methylvaline]-4-cyclosporin;
[(R)-3-(N-iso-Propyl-N-ethylamino)propoxy-Sar]-3-[N-methylvaline]-4-cyclosporin;
[(R)-3-(N-iso-Butylamino)propoxy-Sar]-3-[N-methylvaline]-4-cyclosporin;
[(R)-3-(N-iso-Butyl-N-methylamino)propoxy-Sar]-3-[N-methylvaline]-4-cyclosporin;
[(R)-3-(N-iso-Butyl-N-ethylamino)propoxy-Sar]-3-[N-methylvaline]-4-cyclosporin;
[(R)-3-(N-(2',2'-dimethyl)propylamino)propoxy-Sar]-3-[N-methylvaline]-4-cyclosporin;
[(R)-3-(N-(2',2'-dimethyl)propyl-N-methylamino)propoxy-Sar]-3-[N-methylvaline]-4-yclosporin;
[(R)-3-(N-(2',2'-dimethyl)propyl-N-ethylamino)propoxy-Sar]-3-[N-methylvaline]-4-cyclosporin;
[(R)-4-(N-Azetidinyl)Butylthio-Sar]-3-[N-methylvaline]-4-cyclosporin;
[(R)-4-(N-Pyrrolidinyl)Butylthio-Sar]-3-[N-methylvaline]-4-cyclosporin;
[(R)-4-(N-1H-Imidazolyl)Butylthio-Sar]-3-[N-methylvaline]-4-cyclosporin;
[(R)-4-(N-Piperidinyl)Butylthio-Sar]-3-[N-methylvaline]-4-cyclosporin;
[(R)-4-(N-Morpholino)Butylthio-Sar]-3-[N-methylvaline]-4-cyclosporin;
[(R)-4-(N-Thiomorpholino)Butylthio-Sar]-3-[N-methylvaline]-4-cyclosporin;
[(R)-4-(Piperazinyl)Butylthio-Sar]-3-[N-methylvaline]-4-cyclosporin;
[(R)-4-(N-4-Methylpiperazinyl)Butylthio-Sar]-3-[N-methylvaline]-4-cyclosporin;
[(R)-4-(N-4-Ethylpiperazinyl)Butylthio-Sar]-3-[N-methylvaline]-4-cyclosporin;
[(R)-4-(N-4-n-Propylpiperazinyl)Butylthio-Sar]-3-[N-methylvaline]-4-cyclosporin;
[(R)-4-(N-4-iso-Propylpiperazinyl)Butylthio-Sar]-3-[N-methylvaline]-4-cyclosporin;
[(R)-4-(N-Azetidinyl)Butoxy-Sar]-3-[N-methylvaline]-4-cyclosporin;
[(R)-4-(N-Pyrrolidinyl)Butoxy-Sar]-3-[N-methylvaline]-4-cyclosporin;
[(R)-4-(N-1H-Imidazolyl)Butoxy-Sar]-3-[N-methylvaline]-4-cyclosporin;
[(R)-4-(N-Piperidinyl)Butoxy-Sar]-3-[N-methylvaline]-4-cyclosporin;
[(R)-4-(N-Morpholino)Butoxy-Sar]-3-[N-methylvaline]-4-cyclosporin;
[(R)-4-(N-Thiomorpholino)Butoxy-Sar]-3-[N-methylvaline]-4-cyclosporin;
[(R)-4-(Piperazinyl)Butoxy-Sar]-3-[N-methylvaline]-4-cyclosporin;
[(R)-4-(N-4-Methylpiperazinyl)Butoxy-Sar]-3-[N-methylvaline]-4-cyclosporin;
[(R)-4-(N-4-Ethylpiperazinyl)Butoxy-Sar]-3-[N-methylvaline]-4-cyclosporin;
[(R)-4-(N-4-n-Propylpiperazinyl)Butoxy-Sar]-3-[N-methylvaline]-4-cyclosporin;
[(R)-4-(N-4-iso-Propylpiperazinyl)Butoxy-Sar]-3-[N-methylvaline]-4-cyclosporin;

[(R)-4-(N,N-Dimethylamino)butylthio-Sar]-3-[N-methylvaline]-4-cyclosporin;
[(R)-4-(N,N-Diethylamino)butylthio-Sar]-3-[N-methylvaline]-4-cyclosporin;
[(R)-4-(N,N-Di-n-proylamino)butylthio-Sar]-3-[N-methylvaline]-4-cyclosporin;
[(R)-4-(N-n-Propylamino)butylthio-Sar]-3-[N-methylvaline]-4-cyclosporin;
[(R)-4-(N-n-Propyl-N-methylamino)butylthio-Sar]-3-[N-methylvaline]-4-cyclosporin;
[(R)-4-(N-n-Propyl-N-ethylamino)butylthio-Sar]-3-[N-methylvaline]-4-cyclosporin;
[(R)-4-(N,N-Di-iso-propylamino)butylthio-Sar]-3-[N-methylvaline]-4-cyclosporin;
[(R)-4-(N-iso-Propylamino)butylthio-Sar]-3-[N-methylvaline]-4-cyclosporin;
[(R)-4-(N-iso-Propyl-N-methylamino)butylthio-Sar]-3-[N-methylvaline]-4-cyclosporin;
[(R)-4-(N-iso-Propyl-N-ethylamino)butylthio-Sar]-3-[N-methylvaline]-4-cyclosporin;
[(R)-4-(N-iso-Butylamino)butylthio-Sar]-3-[N-methylvaline]-4-cyclosporin;
[(R)-4-(N-iso-Butyl-N-methylamino)butylthio-Sar]-3-[N-methylvaline]-4-cyclosporin;
[(R)-4-(N-iso-Butyl-N-ethylamino)butylthio-Sar]-3-[N-methylvaline]-4-cyclosporin;
[(R)-4-(N-(2',2'-dimethyl)propylamino)butylthio-Sar]-3-[N-methylvaline]-4-cyclosporin;
[(R)-4-(N-(2',2'-dimethyl)propyl-N-methylamino)butylthio-Sar]-3-[N-methylvaline]-4-cyclosporin;
[(R)-4-(N-(2',2'-dimethyl)propyl-N-ethylamino)butylthio-Sar]-3-[N-methylvaline]-4-cyclosporin;
[(R)-4-(N,N-Dimethylamino)butoxy-Sar]-3-[N-methylvaline]-4-cyclosporin;
[(R)-4-(N,N-Diethylamino)butoxy-Sar]-3-[N-methylvaline]-4-cyclosporin;
[(R)-4-(N,N-Di-n-proylamino)butoxy-Sar]-3-[N-methylvaline]-4-cyclosporin;
[(R)-4-(N-n-Propylamino)butoxy-Sar]-3-[N-methylvaline]-4-cyclosporin;
[(R)-4-(N-n-Propyl-N-methylamino)butoxy-Sar]-3-[N-methylvaline]-4-cyclosporin;
[(R)-4-(N-n-Propyl-N-ethylamino)butoxy-Sar]-3-[N-methylvaline]-4-cyclosporin;
[(R)-4-(N,N-Di-iso-propylamino)butoxy-Sar]-3-[N-methylvaline]-4-cyclosporin;
[(R)-4-(N-iso-Propylamino)butoxy-Sar]-3-[N-methylvaline]-4-cyclosporin;
[(R)-4-(N-iso-Propyl-N-methylamino)butoxy-Sar]-3-[N-methylvaline]-4-cyclosporin;
[(R)-4-(N-iso-Propyl-N-ethylamino)butoxy-Sar]-3-[N-methylvaline]-4-cyclosporin;
[(R)-4-(N-iso-Butylamino)butoxy-Sar]-3-[N-methylvaline]-4-cyclosporin;
[(R)-4-(N-iso-Butyl-N-methylamino)butoxy-Sar]-3-[N-methylvaline]-4-cyclosporin;
[(R)-4-(N-iso-Butyl-N-ethylamino)butoxy-Sar]-3-[N-methylvaline]-4-cyclosporin;
[(R)-4-(N-(2',2'-dimethyl)propylamino)butoxy-Sar]-3-[N-methylvaline]-4-cyclosporin;
[(R)-4-(N-(2',2'-dimethyl)propyl-N-methylamino)butoxy-Sar]-3-[N-methylvaline]-4-cyclosporin;
[(R)-4-(N-(2',2'-dimethyl)propyl-N-ethylamino)butoxy-Sar]-3-[N-methylvaline]-4-cyclosporin;
[(R)-5-(N-Azetidinyl)pentylthio-Sar]-3-[N-methylvaline]-4-cyclosporin;
[(R)-5-(N-Pyrrolidinyl)pentylthio-Sar]-3-[N-methylvaline]-4-cyclosporin;
[(R)-5-(N-1H-Imidazolyl)pentylthio-Sar]-3-[N-methylvaline]-4-cyclosporin;
[(R)-5-(N-Piperidinyl)pentylthio-Sar]-3-[N-methylvaline]-4-cyclosporin;
[(R)-5-(N-Morpholino)pentylthio-Sar]-3-[N-methylvaline]-4-cyclosporin;
[(R)-5-(N-Thiomorpholino)pentylthio-Sar]-3-[N-methylvaline]-4-cyclosporin;
[(R)-5-(Piperazinyl)pentylthio-Sar]-3-[N-methylvaline]-4-cyclosporin;
[(R)-5-(N-4-Methylpiperazinyl)pentylthio-Sar]-3-[N-methylvaline]-4-cyclosporin;
[(R)-5-(N-4-Ethylpiperazinyl)pentylthio-Sar]-3-[N-methylvaline]-4-cyclosporin;
[(R)-5-(N-4-n-Propylpiperazinyl)pentylthio-Sar]-3-[N-methylvaline]-4-cyclosporin;
[(R)-5-(N-4-iso-Propylpiperazinyl)pentylthio-Sar]-3-[N-methylvaline]-4-cyclosporin;
[(R)-5-(N-Azetidinyl)pentyloxy-Sar]-3-[N-methylvaline]-4-cyclosporin;
[(R)-5-(N-Pyrrolidinyl)pentyloxy-Sar]-3-[N-methylvaline]-4-cyclosporin;
[(R)-5-(N-1H-Imidazolyl)pentyloxy-Sar]-3-[N-methylvaline]-4-cyclosporin;
[(R)-5-(N-Piperidinyl)pentyloxy-Sar]-3-[N-methylvaline]-4-cyclosporin;
[(R)-5-(N-Morpholino)pentyloxy-Sar]-3-[N-methylvaline]-4-cyclosporin;
[(R)-5-(N-Thiomorpholino)pentyloxy-Sar]-3-[N-methylvaline]-4-cyclosporin;
[(R)-5-(Piperazinyl)pentyloxy-Sar]-3-[N-methylvaline]-4-cyclosporin;
[(R)-5-(N-4-Methylpiperazinyl)pentyloxy-Sar]-3-[N-methylvaline]-4-cyclosporin;
[(R)-5-(N-4-Ethylpiperazinyl)pentyloxy-Sar]-3-[N-methylvaline]-4-cyclosporin;
[(R)-5-(N-4-n-Propylpiperazinyl)pentyloxy-Sar]-3-[N-methylvaline]-4-cyclosporin;
[(R)-5-(N-4-iso-Propylpiperazinyl)pentyloxy-Sar]-3-[N-methylvaline]-4-cyclosporin;
[(R)-5-(N,N-Dimethylamino)pentylthio-Sar]-3-[N-methylvaline]-4-cyclosporin;
[(R)-5-(N,N-Diethylamino)pentylthio-Sar]-3-[N-methylvaline]-4-cyclosporin;
[(R)-5-(N,N-Di-n-proylamino)pentylthio-Sar]-3-[N-methylvaline]-4-cyclosporin;
[(R)-5-(N-n-Propylamino)pentylthio-Sar]-3-[N-methylvaline]-4-cyclosporin;
[(R)-5-(N-n-Propyl-N-methylamino)pentylthio-Sar]-3-[N-methylvaline]-4-cyclosporin;
[(R)-5-(N-n-Propyl-N-ethylamino)pentylthio-Sar]-3-[N-methylvaline]-4-cyclosporin;
[(R)-5-(N,N-Di-iso-propylamino)pentylthio-Sar]-3-[N-methylvaline]-4-cyclosporin;
[(R)-5-(N-iso-Propylamino)pentylthio-Sar]-3-[N-methylvaline]-4-cyclosporin;
[(R)-5-(N-iso-Propyl-N-methylamino)pentylthio-Sar]-3-[N-methylvaline]-4-cyclosporin;
[(R)-5-(N-iso-Propyl-N-ethylamino)pentylthio-Sar]-3-[N-methylvaline]-4-cyclosporin;
[(R)-5-(N-iso-Butylamino)pentylthio-Sar]-3-[N-methylvaline]-4-cyclosporin;
[(R)-5-(N-iso-Butyl-N-methylamino)pentylthio-Sar]-3-[N-methylvaline]-4-cyclosporin;

[(R)-5-(N-iso-Butyl-N-ethylamino)pentylthio-Sar]-3-[N-methylvaline]-4-cyclosporin;
[(R)-5-(N-(2',2'-dimethyl)propylamino)pentylthio-Sar]-3-[N-methylvaline]-4-cyclosporin;
[(R)-5-(N-(2',2'-dimethyl)propyl-N-methylamino)pentylthio-Sar]-3-[N-methylvaline]-4-cyclosporin;
[(R)-5-(N-(2',2'-dimethyl)propyl-N-ethylamino)pentylthio-Sar]-3-[N-methylvaline]-4-cyclosporin;
[(R)-5-(N,N-Dimethylamino)pentyloxy-Sar]-3-[N-methylvaline]-4-cyclosporin;
[(R)-5-(N,N-Diethylamino)pentyloxy-Sar]-3-[N-methylvaline]-4-cyclosporin;
[(R)-5-(N,N-Di-n-proylamino)pentyloxy-Sar]-3-[N-methylvaline]-4-cyclosporin;
[(R)-5-(N-n-Propylamino)pentyloxy-Sar]-3-[N-methylvaline]-4-cyclosporin;
[(R)-5-(N-n-Propyl-N-methylamino)pentyloxy-Sar]-3-[N-methylvaline]-4-cyclosporin;
[(R)-5-(N-n-Propyl-N-ethylamino)pentyloxy-Sar]-3-[N-methylvaline]-4-cyclosporin;
[(R)-5-(N,N-Di-iso-propylamino)pentyloxy-Sar]-3-[N-methylvaline]-4-cyclosporin;
[(R)-5-(N-iso-Propylamino)pentyloxy-Sar]-3-[N-methylvaline]-4-cyclosporin;
[(R)-5-(N-iso-Propyl-N-methylamino)pentyloxy-Sar]-3-[N-methylvaline]-4-cyclosporin;
[(R)-5-(N-iso-Propyl-N-ethylamino)pentyloxy-Sar]-3-[N-methylvaline]-4-cyclosporin;
[(R)-5-(N-iso-Butylamino)pentyloxy-Sar]-3-[N-methylvaline]-4-cyclosporin;
[(R)-5-(N-iso-Butyl-N-methylamino)pentyloxy-Sar]-3-[N-methylvaline]-4-cyclosporin;
[(R)-5-(N-iso-Butyl-N-ethylamino)pentyloxy-Sar]-3-[N-methylvaline]-4-cyclosporin;
[(R)-5-(N-(2',2'-dimethyl)propylamino)pentyloxy-Sar]-3-[N-methylvaline]-4-cyclosporin;
[(R)-5-(N-(2',2'-dimethyl)propyl-N-methylamino)pentyloxy-Sar]-3-[N-methylvaline]-4-cyclosporin; and
[(R)-5-(N-(2',2'-dimethyl)propyl-N-ethylamino)pentyloxy-Sar]-3-[N-methylvaline]-4-cyclosporin;
or pharmaceutically acceptable salt thereof.

5. The compound of claim 4 selected from the group consisting of:
[(R)-2-(N,N-Diethylamino)ethylthio-Sar]-3-[N-MeIle]-4-cyclosporin;
[(R)-3-(N,N-Diethylamino)propylthio-Sar]-3-[N-MeIle]-4-cyclosporin;
[(R)-3-(N-Morpholino)propyl-Sar]-3-[N-MeIle]-4-cyclosporin;
[(R)-3-(N-Pyrrolidinyl)propylthio-Sar]-3-[N-MeIle]-4-cyclosporin;
[(R)-3-(N-Piperidinyl)propylthio-Sar]-3-[N-MeIle]-4-cyclosporin;
[(R)-3-(N-4-Methylpiperazinyl)propylthio-Sar]-3-[N-MeIle]-4-cyclosporin;
[(R)-3-(N,N-Diethylamino)propylthio-Sar]-3-[N-MeVal]-4-cyclosporin;
[(R)-3-(N-Morpholino)propyl-Sar]-3-[N-MeVal]-4-cyclosporin;
[(R)-3-(N-Pyrrolidinyl)propylthio-Sar]-3-[N-MeVal]-4-cyclosporin;
[(R)-3-(N-Piperidinyl)propylthio-Sar]-3-[N-MeVal]-4-cyclosporin; and
[(R)-3-(N-4-Methylpiperazinyl)propylthio-Sar]-3-[N-MeVal]-4-cyclosporin, or pharmaceutically acceptable salt thereof.

6. A pharmaceutical composition comprising at least one compound according to claim 1 and a pharmaceutically-acceptable carrier or diluent.

7. A method for treating HIV infection, hepatitis C virus infection or hepatitis B virus infection in a mammalian species in need thereof, the method comprising administering to the mammalian species a therapeutically effective amount of at least one compound according to claim 1.

* * * * *